US012171768B2

(12) United States Patent
Gollob et al.

(10) Patent No.: US 12,171,768 B2
(45) Date of Patent: Dec. 24, 2024

(54) IRAK4 DEGRADERS AND USES THEREOF

(71) Applicant: Kymera Therapeutics, Inc., Watertown, MA (US)

(72) Inventors: Jared Gollob, Watertown, MA (US); Jeffrey Davis, Watertown, MA (US); Alice Mcdonald, Watertown, MA (US); Haojing Rong, Watertown, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 94 days.

(21) Appl. No.: 17/651,201

(22) Filed: Feb. 15, 2022

(65) Prior Publication Data

US 2022/0273668 A1    Sep. 1, 2022

Related U.S. Application Data

(60) Provisional application No. 63/265,466, filed on Dec. 15, 2021, provisional application No. 63/263,055, filed on Oct. 26, 2021, provisional application No. 63/149,621, filed on Feb. 15, 2021.

(51) Int. Cl.
| | |
|---|---|
| *A61K 31/5386* | (2006.01) |
| *A61K 9/00* | (2006.01) |
| *A61K 9/20* | (2006.01) |
| *A61K 9/28* | (2006.01) |
| *A61P 31/00* | (2006.01) |

(52) U.S. Cl.
CPC ........ *A61K 31/5386* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/205* (2013.01); *A61K 9/2054* (2013.01); *A61K 9/2853* (2013.01); *A61P 31/00* (2018.01)

(58) Field of Classification Search
None
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,217,866 A | 6/1993 | Summerton et al. | |
| 5,360,811 A | 11/1994 | Tegeler et al. | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 5,721,246 A | 2/1998 | Yoshino et al. | |
| 6,306,663 B1 | 10/2001 | Kenten et al. | |
| 6,552,065 B2 | 4/2003 | Remiszewski et al. | |
| 6,559,280 B2 | 5/2003 | Kenten et al. | |
| 6,627,754 B2 | 9/2003 | Blumenkopf et al. | |
| 6,949,537 B2 | 9/2005 | Garlich et al. | |
| 7,041,298 B2 | 5/2006 | Deshaies et al. | |
| 7,071,189 B2 | 7/2006 | Kawashima et al. | |
| 7,074,620 B2 | 7/2006 | Kenten et al. | |
| 7,173,015 B2 | 2/2007 | Schreiber et al. | |
| 7,208,157 B2 | 4/2007 | Dashaies et al. | |
| 7,273,920 B2 | 9/2007 | Kenten et al. | |
| 7,307,077 B2 | 12/2007 | Kawashima et al. | |
| 7,390,799 B2 | 6/2008 | Bruncko et al. | |
| 7,402,325 B2 | 7/2008 | Addington | |
| 7,449,458 B2 | 11/2008 | Bhamidipati et al. | |
| 7,501,496 B1 | 3/2009 | Endl et al. | |
| 7,514,444 B2 | 4/2009 | Honigberg et al. | |
| 7,528,143 B2 | 5/2009 | Noronha et al. | |
| 7,557,210 B2 | 7/2009 | Singh et al. | |
| 7,598,257 B2 | 10/2009 | Rodgers et al. | |
| 7,622,496 B2 | 11/2009 | Larsen et al. | |
| 7,667,039 B2 | 2/2010 | Garcia-Echeverria et al. | |
| 7,713,943 B2 | 5/2010 | Klippel-Giese et al. | |
| 7,781,433 B2 | 8/2010 | Chuckowree et al. | |
| 7,932,260 B2 | 4/2011 | Fowler et al. | |
| 7,989,622 B2 | 8/2011 | Bajjalieh et al. | |
| 8,138,347 B2 | 3/2012 | Knight et al. | |
| 8,185,616 B2 | 5/2012 | Nagata et al. | |
| 8,217,035 B2 | 7/2012 | Burger et al. | |
| 8,338,439 B2 | 12/2012 | Singh et al. | |
| 8,486,941 B2 | 7/2013 | Burns et al. | |
| 8,906,682 B2 | 12/2014 | June et al. | |
| 9,500,653 B2 | 11/2016 | Crews et al. | |
| 9,632,089 B2 | 4/2017 | Crews et al. | |
| 9,694,084 B2 | 7/2017 | Bradner et al. | |
| 9,750,816 B2 | 9/2017 | Bradner et al. | |
| 9,770,512 B2 | 9/2017 | Bradner et al. | |
| 9,821,068 B2 | 11/2017 | Bradner et al. | |
| 9,969,710 B2 | 5/2018 | Jorand-Lebrun et al. | |
| 10,125,114 B2 | 11/2018 | Bradner et al. | |
| 10,336,744 B2 | 7/2019 | Harling et al. | |
| 10,874,743 B2 | 12/2020 | Mainolfi et al. | |
| 11,117,889 B1 | 9/2021 | Mainolfi et al. | |
| 11,352,350 B2 | 6/2022 | Mainolfi et al. | |
| 2001/0053782 A1 | 12/2001 | Blumenkopf et al. | |
| 2002/0042427 A1 | 4/2002 | Tang et al. | |
| 2002/0068063 A1 | 6/2002 | Deshaies et al. | |
| 2002/0183360 A1 | 12/2002 | Muller et al. | |
| 2004/0029902 A1 | 2/2004 | Singh et al. | |

(Continued)

FOREIGN PATENT DOCUMENTS

| | | |
|---|---|---|
| CN | 105085620 B | 5/2018 |
| WO | WO1996007655 A1 | 3/1996 |

(Continued)

OTHER PUBLICATIONS

Mullard, Nature Biotechnology, 38, 2020 (Year: 2020).*

(Continued)

*Primary Examiner* — Susan T Tran
*Assistant Examiner* — William Craigo
(74) *Attorney, Agent, or Firm* — Andrea L. C. Reid; John P. Rearick; Todd K. Macklin

(57) ABSTRACT

The present invention provides IRAK4 degraders, formulations and unit dosage forms thereof, and methods of use thereof.

4 Claims, 17 Drawing Sheets

(56) References Cited

U.S. PATENT DOCUMENTS

| | | |
|---|---|---|
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0196150 A1 | 8/2011 | Man et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0025093 A1 | 1/2015 | Romero et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225410 A1 | 8/2015 | Castro et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Kelley et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008896 A1 | 1/2017 | Dahmann et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 3/2018 | Harling et al. |
| 2018/0134684 A1 | 5/2018 | Bradner et al. |
| 2018/0147202 A1 | 5/2018 | Crew et al. |
| 2018/0169097 A1 | 6/2018 | Hammerman et al. |
| 2018/0186799 A1 | 7/2018 | Gardner et al. |
| 2018/0194724 A1 | 7/2018 | Kemp et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2018/0327419 A1 | 11/2018 | Bradner et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151295 A1 | 5/2019 | Crew et al. |
| 2019/0151457 A1 | 5/2019 | Bradner et al. |
| 2019/0192532 A1 | 6/2019 | Bradner et al. |
| 2019/0192668 A1 | 6/2019 | Mainolfi et al. |
| 2019/0276474 A1 | 9/2019 | Chan et al. |
| 2019/0374528 A1 | 12/2019 | Gray et al. |
| 2020/0010468 A1 | 1/2020 | Ji et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |
| 2021/0147382 A1 | 5/2021 | Bellenie et al. |
| 2021/0228562 A1 | 7/2021 | Weiss |
| 2021/0323952 A1 | 10/2021 | Mainolfi et al. |

FOREIGN PATENT DOCUMENTS

| | | |
|---|---|---|
| WO | WO2001042246 A2 | 6/2001 |
| WO | WO2002020740 A2 | 3/2002 |
| WO | WO2002088112 A1 | 11/2002 |
| WO | WO2003063794 A2 | 8/2003 |
| WO | WO2004019973 A1 | 3/2004 |
| WO | WO2004089925 A1 | 10/2004 |

(56) References Cited

FOREIGN PATENT DOCUMENTS

| | | |
|---|---|---|
| WO | WO2004106328 A1 | 12/2004 |
| WO | WO2005007623 A2 | 1/2005 |
| WO | WO2005113554 A2 | 12/2005 |
| WO | WO2006029879 A2 | 3/2006 |
| WO | WO2006078846 A1 | 7/2006 |
| WO | WO2006105021 A2 | 10/2006 |
| WO | WO2006122806 A2 | 11/2006 |
| WO | WO2007005874 A2 | 1/2007 |
| WO | WO2007016176 A2 | 2/2007 |
| WO | WO2007044729 A2 | 4/2007 |
| WO | WO2007053452 A1 | 5/2007 |
| WO | WO2007070514 A1 | 6/2007 |
| WO | WO2007084786 A1 | 7/2007 |
| WO | WO2007129161 A2 | 11/2007 |
| WO | WO2008039218 A2 | 4/2008 |
| WO | WO2008109943 A1 | 9/2008 |
| WO | WO2008118802 A1 | 10/2008 |
| WO | WO2008132601 A1 | 11/2008 |
| WO | WO2009009116 A2 | 1/2009 |
| WO | WO2009044273 A2 | 4/2009 |
| WO | WO2009073620 A2 | 6/2009 |
| WO | WO2009114512 A1 | 9/2009 |
| WO | WO2009132238 A2 | 10/2009 |
| WO | WO2010019570 A2 | 2/2010 |
| WO | WO2010077634 A1 | 7/2010 |
| WO | WO2011028683 A1 | 3/2011 |
| WO | WO2011043371 A1 | 4/2011 |
| WO | WO2011056652 A1 | 5/2011 |
| WO | WO2011070024 A1 | 6/2011 |
| WO | WO2011090760 A1 | 7/2011 |
| WO | WO2011107553 A1 | 9/2011 |
| WO | WO2011109400 A2 | 9/2011 |
| WO | WO2011131407 A1 | 10/2011 |
| WO | WO2011140249 A2 | 11/2011 |
| WO | WO2012003281 A2 | 1/2012 |
| WO | WO2012007375 A1 | 1/2012 |
| WO | WO2012032433 A1 | 3/2012 |
| WO | WO2012068546 A1 | 5/2012 |
| WO | WO2012078559 A2 | 6/2012 |
| WO | WO2012084704 A1 | 6/2012 |
| WO | WO2012097013 A1 | 7/2012 |
| WO | WO2012129258 A1 | 9/2012 |
| WO | WO2012142237 A1 | 10/2012 |
| WO | WO2012145493 A1 | 10/2012 |
| WO | WO2013042137 A1 | 3/2013 |
| WO | WO2013066729 A1 | 5/2013 |
| WO | WO2013079174 A1 | 6/2013 |
| WO | WO2013087699 A1 | 6/2013 |
| WO | WO2013106535 A1 | 7/2013 |
| WO | WO2013106612 A1 | 7/2013 |
| WO | WO2013106614 A1 | 7/2013 |
| WO | WO2013106641 A1 | 7/2013 |
| WO | WO2013106643 A2 | 7/2013 |
| WO | WO2013106646 A2 | 7/2013 |
| WO | WO2013119716 A1 | 8/2013 |
| WO | WO2013132044 A1 | 9/2013 |
| WO | WO2013169264 A1 | 11/2013 |
| WO | WO2014008218 A1 | 1/2014 |
| WO | WO2014008992 A1 | 1/2014 |
| WO | WO2014011902 A1 | 1/2014 |
| WO | WO2014011906 A2 | 1/2014 |
| WO | WO2014011911 A2 | 1/2014 |
| WO | WO2014036357 A1 | 3/2014 |
| WO | WO2014044622 A1 | 3/2014 |
| WO | WO2014058685 A1 | 4/2014 |
| WO | WO2014058691 A1 | 4/2014 |
| WO | WO2014063061 A1 | 4/2014 |
| WO | WO2014074660 A1 | 5/2014 |
| WO | WO2014074675 A1 | 5/2014 |
| WO | WO2014108452 A1 | 7/2014 |
| WO | WO2014121931 A1 | 8/2014 |
| WO | WO2014121942 A1 | 8/2014 |
| WO | WO2014142237 A1 | 9/2014 |
| WO | WO2014143672 A1 | 9/2014 |
| WO | WO2015048281 A1 | 4/2015 |
| WO | WO2015068856 A1 | 5/2015 |
| WO | WO2015071393 A1 | 5/2015 |
| WO | WO2015091426 A1 | 6/2015 |
| WO | WO2015103453 A1 | 7/2015 |
| WO | WO2015104662 A1 | 7/2015 |
| WO | WO2015104688 A1 | 7/2015 |
| WO | WO2015150995 A1 | 10/2015 |
| WO | WO2015160845 A2 | 10/2015 |
| WO | WO2015164374 A1 | 10/2015 |
| WO | WO2015193846 A1 | 12/2015 |
| WO | WO2016011390 A1 | 1/2016 |
| WO | WO2016053769 A1 | 4/2016 |
| WO | WO2016053770 A1 | 4/2016 |
| WO | WO2016053771 A1 | 4/2016 |
| WO | WO2016053772 A1 | 4/2016 |
| WO | WO2016081679 A1 | 5/2016 |
| WO | WO2016105518 A1 | 6/2016 |
| WO | WO2016118666 A1 | 7/2016 |
| WO | WO2016144844 A1 | 9/2016 |
| WO | WO2016144846 A1 | 9/2016 |
| WO | WO2016144847 A1 | 9/2016 |
| WO | WO2016144848 A1 | 9/2016 |
| WO | WO2016144849 A1 | 9/2016 |
| WO | WO2016149668 A1 | 9/2016 |
| WO | WO2016169989 A1 | 10/2016 |
| WO | WO2016172560 A1 | 10/2016 |
| WO | WO2016174183 A1 | 11/2016 |
| WO | WO2016197032 A1 | 12/2016 |
| WO | WO2016197114 A1 | 12/2016 |
| WO | WO2016210034 A1 | 12/2016 |
| WO | WO2017004133 A1 | 1/2017 |
| WO | WO2017004134 A1 | 1/2017 |
| WO | WO2017007612 A1 | 1/2017 |
| WO | WO2017009798 A1 | 1/2017 |
| WO | WO2017009806 A1 | 1/2017 |
| WO | WO2017011371 A1 | 1/2017 |
| WO | WO2017011590 A1 | 1/2017 |
| WO | WO2017030814 A1 | 2/2017 |
| WO | WO2017033093 A1 | 3/2017 |
| WO | WO2017049068 A1 | 3/2017 |
| WO | WO2017059280 A1 | 4/2017 |
| WO | WO2017079267 A1 | 5/2017 |
| WO | WO2017108723 A2 | 6/2017 |
| WO | WO2017117473 A1 | 7/2017 |
| WO | WO2017117474 A1 | 7/2017 |
| WO | WO2017127430 A1 | 7/2017 |
| WO | WO2017161119 A1 | 9/2017 |
| WO | WO2017176708 A1 | 10/2017 |
| WO | WO2017176957 A1 | 10/2017 |
| WO | WO2017176958 A1 | 10/2017 |
| WO | WO2017197036 A1 | 11/2017 |
| WO | WO2017197046 A1 | 11/2017 |
| WO | WO2017197051 A1 | 11/2017 |
| WO | WO2017197055 A1 | 11/2017 |
| WO | WO2017197056 A1 | 11/2017 |
| WO | WO2017201449 A1 | 11/2017 |
| WO | WO2017205762 A1 | 11/2017 |
| WO | WO2017205766 A1 | 11/2017 |
| WO | WO2017207385 A1 | 12/2017 |
| WO | WO2017211924 A1 | 12/2017 |
| WO | WO2018052058 A1 | 3/2018 |
| WO | 2018071606 | 4/2018 |
| WO | WO2018089736 A1 | 5/2018 |
| WO | WO2018098367 A1 | 5/2018 |
| WO | WO2018119441 A1 | 6/2018 |
| WO | WO2018144649 A1 | 8/2018 |
| WO | WO2018209012 A1 | 11/2018 |
| WO | WO2018237026 A1 | 12/2018 |
| WO | WO2019043214 A1 | 3/2019 |
| WO | WO2019060693 A1 | 3/2019 |
| WO | WO2019060742 A1 | 3/2019 |
| WO | 2019094772 | 5/2019 |
| WO | WO2019084026 A1 | 5/2019 |
| WO | WO2019084030 A1 | 5/2019 |
| WO | WO2019099868 A2 | 5/2019 |
| WO | WO2019099926 A1 | 5/2019 |
| WO | WO2019133531 A1 | 7/2019 |
| WO | WO2019140380 A1 | 7/2019 |
| WO | WO2019140387 A1 | 7/2019 |

(56) References Cited

FOREIGN PATENT DOCUMENTS

| | | |
|---|---|---|
| WO | WO2019160915 A1 | 8/2019 |
| WO | WO2019165229 A1 | 8/2019 |
| WO | WO2019236483 A1 | 12/2019 |
| WO | WO2020010177 A1 | 1/2020 |
| WO | WO2020010210 A1 | 1/2020 |
| WO | WO2020010227 A1 | 1/2020 |
| WO | WO2020018788 A1 | 1/2020 |
| WO | 2020038415 A1 | 2/2020 |
| WO | 2020041331 A1 | 2/2020 |
| WO | WO-2020028258 A1 * 2/2020 ........... A61K 31/415 |
| WO | WO2020113233 A1 | 6/2020 |
| WO | WO2020251969 A1 | 12/2020 |
| WO | WO2020251971 A1 | 12/2020 |
| WO | WO2020251972 A1 | 12/2020 |
| WO | WO2020251974 A1 | 12/2020 |
| WO | WO2020264490 A1 | 12/2020 |
| WO | WO2020264499 A1 | 12/2020 |
| WO | WO2021011631 A1 | 1/2021 |
| WO | WO2021011634 A1 | 1/2021 |
| WO | WO2021011868 A1 | 1/2021 |
| WO | WO2021011871 A1 | 1/2021 |
| WO | WO2021053555 A1 | 3/2021 |
| WO | WO2021119159 A1 | 6/2021 |
| WO | WO2021127190 A1 | 6/2021 |
| WO | WO2021127278 A1 | 6/2021 |
| WO | WO2021127283 A2 | 6/2021 |
| WO | 2021158634 A1 | 8/2021 |
| WO | 2021247897 A1 | 12/2021 |
| WO | 2022174268 A1 | 8/2022 |

OTHER PUBLICATIONS

KT474, IUPHAR, 2024 (Year: 2024).*
Friesen, molecular pharmaceutics, 2008 (Year: 2008).*
Brewster, Advanced Drug Delivery Reviews, 59, 2007 (Year: 2007).*
Adams et al., "Big opportunities for small molecules in immuno-oncology," Nat Rev Drug Discov., 2015, 14(9):603-622.
Aruri et al., "Metal-free Cross-Dehydrogenative Coupling of HN-azoles with a-C(sp3)-H Amides via C—H Activation and Its Mechanistic and Application Studies," J Org Chem., 2017, 82(2):1000-1012.
Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.
Berge et al., "Pharmaceutical salts," J Pharm Sci., 1977, 66(1):1-19.
Berndsen et al., "New insights into ubiquitin E3 ligase mechanism," Nat Struct Mol Biol., 2014, 21(4):301-307.
Blake et al., "Studies with deuterated drugs," J Pharm Sci. 1975;64(3):367-391.
Boichenko et al., "A FRET-Based Assay for the Identification and Characterization of Cereblon Ligands," J Med Chem. 2016, 59(2):770-774.
Buckley et al., "IRAK-4 inhibitors. Part 1: a series of amides," Bioorg Med Chem Lett. 2008, 18(11):3211-3214.
Buckley et al., "IRAK-4 inhibitors. Part II: a structure-based assessment of imidazo[1,2-a]pyridine binding," Bioorg Med Chem Lett., 2008, 18(11):3291-3295.
Buckley et al., "IRAK-4 inhibitors. Part III: A series of imidazo[1,2-a]pyridines," Bioorg Med Chem Lett., 2008, 18(12):3656-3660.
Cameron et al., "Loss of Interleukin Receptor-Associated Kinase 4 Signaling Suppresses Amyloid Pathology and Alters Microglial Phenotype in a Mouse Model of Alzheimer's Disease," J Neurosci., 2012, 32(43):15112-23.
Cario, "Therapeutic Impact of Toll-like Receptors on Inflammatory Bowel Diseases: A Multiple-edged Sword," Inflamm Bowel Dis., 2008, 14(3):411-421.
CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Chang et al., "What is the functional role of the thalidomide binding protein cereblon?" Int J Biochem Mol Biol. 2011;2(3):287-94.
Charrier et al., "Desulfonylative Radical Ring Closure onto Aromatics. A Modular Route to Benzazepin-2-ones and 5-Arylpiperidin-2-ones," Org. Lett., 2012, 14(8): 2018-2021.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem., 2015, 58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol., 2011, 186(2):1279-1288.
Chou and Talalay, "Quantitative analysis of dose-effect relationships: the combined effects of multiple drugs or enzyme inhibitors," Adv Enzyme Regul. 1984, 22:27-55.
Cohen, "Targeting protein kinases for the development of anti-inflammatory drugs," Curr Opin Cell Biol., 2009, 21(2):17-24.
Connolly et al., "Complexities of TGF-beta Targeted Cancer Therapy," Int J Biol Sci., 2012, 8(7):964-978.
Contino-Pepin et al., "Preliminary biological evaluations of new thalidomide analogues for multiple sclerosis application," Bioorg Med Chem Lett., 2009, 19(3):878-881.
Crews, "Targeting the Undruggable Proteome: The Small Molecules of My Dreams," Chem Biol., 2010, 17(6):551-555.
Cushing et al., "Interleukin 1/Toll-like receptor-induced autophosphorylation activates interleukin 1 receptor-associated kinase 4 and controls cytokine induction in a cell type-specific manner," J Biol Chem. 2014, 289(15):10865-10875.
Cushing et al., "IRAK4 kinase controls Toll-like receptor induced inflammation through the transcription factor IRF5 in primary human monocytes," J Biol Chem. 2017, 292(45):18689-18698.
Dalbeth et al., "Hyperuricaemia and gout: state of the art and future perspectives," Ann Rheum Dis. 2014, 73(9):1598-600.
De Nardo et al. "Interleukin-1 receptor-associated kinase 4 (IRAK4) plays a dual role in myddosome formation and Toll-like receptor signaling," J Biol Chem. 2018, 293(39):15195-15207.
Degorce et al., "Optimization of permeability in a series of pyrrolotriazine inhibitors of IRAK4," Bioorg Med Chem., 2018, 26(4):913-924.
Deshaies and Joazeiro, "RING domain E3 ubiquitin ligases," Annu Rev Biochem., 2009, 78:399-434.
Devi et al., "Medicinal Attributes of Imidazo[1,2-a]pyridine Derivatives: An Update," Curr Top Med Chem, 2016, 16(26):2963-2994.
Dinarello, "IL-1: Discoveries, controversies and future directions," Eur J Immunol. 2010, 40(3):599-606.
Dinarello, "Interleukin 1 and interleukin 18 as mediators of inflammation and the aging process," Am J Clin Nutr., 2006, 83(suppl):447S-455S.
Dinarello, "Interleukin-18 and the Pathogenesis of Inflammatory Diseases," Semin Nephrol., 2007, 27(1):98-114.
Dudhgaonkar et al., "Selective IRAK4 Inhibition Attenuates Disease in Murine Lupus Models and Demonstrates Steroid Sparing Activity," J Immunol., 2017, 198(3):1308-1319.
Dunne et al., "IRAK1 and IRAK4 Promote Phosphorylation, Ubiquitation, and Degradation of MyD88 Adaptor-like (Mal)," J Biol Chem., 2010, 285(24):18276-82.
El-Gamal et al., "Recent Advances of Colony-Stimulating Factor-1 Receptor (CSF-IR) Kinase and Its Inhibitors," J Med Chem., 2018, 61(13):5450-5466.
Fischer et al., "Structure of the DDB1-CRBN E3 ubiquitin ligase in complex with thalidomide," Nature, 2014, 512(7512):49-53.
Fisher et al., "The complexities inherent in attempts to decrease drug clearance by blocking sites of CYP-mediated metabolism," Curr Opin Drug Discov Devel., 2006, 9(1):101-109.
Flannery et al., "The interleukin-1 receptor-associated kinases: Critical regulators of innate immune signaling," Biochem Pharmacol. 2010, 80(12):1981-91.

(56) References Cited

OTHER PUBLICATIONS

Foster, "Deuterium isotope effects in the metabolism of drugs and xenobiotics: implications for drug design," Advances in Drug Research, 1985, 14:1-40.
Fukuto et al., "Determination of the mechanism of demethylenation of (methylenedioxy)phenyl compounds by cytochrome P450 using deuterium isotope effects," J Med Chem., 1991, 34(9):2871-2876.
Gearing, "Targeting toll-like receptors for drug development: a summary of commercial approaches," Immunol Cell Biol., 2007;85(6):490-494.
Geyer and Müller-Ladner, "Actual status of antiinterleukin-1 therapies in rheumatic diseases," Curr Opin Rheumatol. 2010;22(3):246-251.
Gottipati et al., "IRAK1: A critical signaling mediator of innate immunity," Cell Signal, 2008, 20(2):269-76.
Hagner et al., "CC-122, a pleiotropic pathway modifier, mimics an interferon response and has antitumor activity in DLBCL," Blood, 2015, 126(6):779-789.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAPI/NRF2) Protein-Protein Interaction," J. Med. Chem., 2019, 62(9): 4683-4702.
Hennessy et al., "Targeting Toll-like receptors: emerging therapeutics?" Nat Rev Drug Discov., 2010, 9(4):293-307.
Hines et al., "MDM2-Recruiting PROTAC Offers Superior, Synergistic Antiproliferative Activity via Simultaneous Degradation of BRD4 and Stabilization of p53," Cancer Res., 2019, 79(1):251-262.
Hoffman et al., "Efficacy and Safety of Rilonacept (Interleukin-1 Trap) in Patients with Cryopyrin-Associated Periodic Syndromes," Arthritis Rheum., 2008, 58(8):2443-2445.
Iannello et al., "Role of Interleukin-18 in the Development and Pathogenesis of Aids," Aids Rev., 2009, 11(3):115-125.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science, 2010, 327(5971):1345-1350.
Kargbo, "Protac Degradation of IRAK4 for the Treatment of Cancer," ACS Med. Chem. Lett., 2019, 10(10):1370-1371.
Kelly et al., "Selective interleukin-1 receptor-associated kinase 4 inhibitors for the treatment of autoimmune disorders and lymphoid malignancy," J Exp Med., 2015, 212(13):2189-2201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem., 2013, 56(20):7788-7803.
Kim et al., "A critical role for IRAK4 kinase activity in Toll-like receptor-mediated innate immunity," J Exp Med., 2007, 204(5):1025-1036.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol., 2014, 387(10):909-919.
Kou et al., "Effects of RuPeng15 Powder (RPP15) on Monosodium Urate Crystal-Induced Gouty Arthritis in Rats," Evid Based Complement Alternat Med., 2015, 2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem., 2007, 282(18):13552-13560.
Krönke et al., "Lenalidomide causes selective degradation of IKZF1 and IKZF3 in multiple myeloma cells" Science, 2014, 343(6168):301-305.

Ku et al., "Selective predisposition to bacterial infections in IRAK-4-deficient children: IRAK-4-dependent TLRs are otherwise redundant in protective immunity," J Exp Med., 2007, 204(10):2407-2422.
Kubo-Murai et al., "IRAK-4-dependent Degradation of IRAK-1 is a Negative Feedback Signal for TLR-mediated NF-κB Activation," J Biochem., 2008, 143(3):295-302.
Küppers, "IRAK inhibition to shut down TLR signaling in autoimmunity and MyD88-dependent lymphomas," J Exp Med., 2015, 212(13):2184.
Kushner et al., "Pharmacological uses and perspectives of heavy water and deuterated compounds," Can J Physiol Pharmacol., 1999, 77(2):79-88.
Lebakken et al., "A Fluorescence Lifetime Based Binding Assay to Characterize Kinase Inhibitors," J Biomol Screen. 2007, 12(6):828-841.
Lee et al., "Discovery of Clinical Candidate 1-{[2S,3S,4S)-3-ethyl-4-fluoro-5-oxopyrrolidin-2-yl]methoxy }-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.
Li et al., "Genome-wide and functional annotation of human E3 ubiquitin ligases identifies MULAN, a mitochondrial E3 that regulates the organelle's dynamics and signaling, " PLoS One. 2008;3(1):e1487.
Li et al., "IRAK-4: A novel member of the IRAK family with the properties of an IRAK-kinase," Proc Natl Acad Sci USA., 2002, 99(8):5567-5572.
Li et al., "Targeting interleukin-1 receptor-associated kinase for human hepatocellular carcinoma," J Exp Clin Cancer Res., 2016, 35(1):140.
Li, "IRAK4 in TLR/IL-IR signaling: Possible clinical applications," Eur J Immunol., 2008, 38(3):614-618.
Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015, 6(6):683-688.
Lin et al., "Helical assembly in the MyD88-IRAK4-IRAK2 complex in TLR/IL-1R signalling," Nature, 2010, 465(7300):885-890.
Lu et al., "Discovery of a Keap1-dependent peptide PROTAC to knockdown Tau by ubiquitination-proteasome degradation pathway," Euro J Med Chem., 2018, 46:251-259.
Lu et al., "Hijacking the E3 Ubiquitin Ligase Cereblon to Efficiently Target BRD4," Chem Biol, 2015, 2(6):755-763.
Lu et al., "The myeloma drug lenalidomide promotes the cereblon-dependent destruction of Ikaros proteins," Science, 2014, 343(6168):305-309.
Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clin Proc., 2009, 84(2):114-122.
Martinon et al., "Gout-associated uric acid crystals activate the NALP3 inflammasome," Nature, 2006, 440(7081):237-241.
Maschera et al., "Overexpression of an enzymatically inactive interleukin-1-receptor-associated kinase activates nuclear factor-kB," Biochem J., 1999, 339(Pt2):227-231.
Matyskiela et al., "A Cereblon Modulator (CC-220) with Improved Degradation of Ikaros and Aiolos," J Med Chem., 2018, 61(2):535-542.
McElroy et al., "Discovery and hit-to-lead optimization of 2,6-diaminopyrimidine Inhibitors of interleukin-1 receptor-associated kinase 4," Bioorg Med Chem Lett., 2015, 25(9):1836-1841.
McElroy et al., "Potent and Selective Amidopyrazole Inhibitors of IRAK4 That Are Efficacious in a Rodent Model of Inflammation," ACS Med Chem Lett., 2015, 6(6):677-682.
Moynagh, "The Pellino Family: IRAK E3 ligases with emerging roles in innate immune signalling," Trends Immunol., 2009, 30(1): 33-42.
Muller et al., "Amino-Substituted Thalidomide Analogs: Potent Inhibitors of TNF -? Production," Bioorg Med Chem Lett, 1999, 9(11):1625-1630.
Ngo et al., "Oncogenically active MYD88 mutations in human lymphoma," Nature, 2011, 470(7332):115-119.

(56) References Cited

OTHER PUBLICATIONS

Nunes et al., "Targeting IRAK4 for Degradation with PROTACSs," ACS Med Chem Lett., 2019, 10(7):1081-1085.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem., 2017, 292(11):4556-4570.
Ohoka et al., "Development of Small Molecule Chimeras That Recruit AhR E3 Ligase to Target Proteins," ACS Chem. Biol., 2019, 14(12):2822-2832.
Okazaki et al., "A rheostat for immune responses: the unique properties of PD-1 and their advantages for clinical application," Nat. Immunol. 2013, 14(12):1212-1218.
Patra and Choi, "Recent Progress in the Molecular Recognition and Therapeutic Importance of Interleukin-1 Receptor-Associated Kinase 4," Molecules. 2016, 21(11):1529.
PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/040101, dated Nov. 10, 2020.
PCT International Search Report and Written Opinion from PCT/US2020/040125, dated Nov. 13, 2020.
PCT International Search Report and Written Opinion from PCT/US2020/042105, dated Nov. 20, 2020.
PCT International Search Report and Written Opinion from PCT/US2020/042109, dated Dec. 10, 2020.
PCT International Search Report and Written Opinion from PCT/US2020/042530, dated Oct. 16, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065628, dated May 28, 2021.
PCT International Search Report and Written Opinion from PCT/US2020/065752, dated Mar. 25, 2021.
PCT International Search Report and Written Opinion from PCT/US2020/065757, dated May 28, 2021.
PCT International Search Report and Written Opinion from PCT/US2020/066859, dated Apr. 27, 2021.
PCT International Search Report and Written Opinion from PCT/US2021/062640, dated Feb. 25, 2022.
PCT International Search Report and Written Opinion from PCT/US2023/060645, dated Mar. 31, 2023.
PCT International Search Report and Written Opinion from PCT/US2021/035745, dated Sep. 27, 2021.
PCT International Search Report and Written Opinion from PCT/US2021/035747, dated Sep. 27, 2021.
PCT International Search Report and Written Opinion from PCT/US2022/070662, dated Apr. 18, 2022.
PCT International Search Report and Written Opinion from PCT/US2022/070664, dated May 3, 2022.
Picard et al., "Clinical features and outcome of patients with IRAK-4 and MyD88 deficiency," Medicine (Baltimore). 2010, 89(6):403-425.
Picard et al., "Inherited human IRAK-4 deficiency: an update," Immunol Res., 2007, 38(1-3):347-52.
Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood, 2016, 126(23): 675-676.
Powers et al., "Discovery and initial SAR of inhibitors of interleukin-1 receptor-associated kinase-4," Bioorg Med Chem Lett., 2006;16(11):2842-2845.
Priyadarshini et al., "Copper catalyzed oxidative cross-coupling of aromatic amines with 2-pyrrolidinone: a facile synthesis of N-aryl-r-amino-r-lactams," Tetrahedron. 2014, 70(36):6068-6074.
Pubmed Compound Summary for CID 101524675, "(2R)-3-Fluoro-2-(2- methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl)piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Feb. 25, 2020 (6 pages).
Pubmed Compound Summary for CID 5426, "Thalidomide," created Mar. 25, 2005.
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Feb. 25, 2020 (7 pages).

(56) References Cited

OTHER PUBLICATIONS

Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).

Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).

Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Feb. 25, 2020 (6 pages).

Pubmed Compound Summary for CID 84036945, 1-Piperidin-3-yl-3H-indol-2-one, U.S. Library of Medicine, created Oct. 20, 2014, https://pubchem.ncbi.nlm.nih.gov/compound/84036945. Date Accessed: Feb. 25, 2020 (7 pages).

Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.

Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.

Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.

Raina et al., "Chemical Inducers of Targeted Protein Degradation," J Biol Chem. 2010, 285(15):11057-110560.

Ramirez et al., "Defining causative factors contributing in the activation of hedgehog signaling in diffuse large B-cell lymphoma," Leuk. Res. 2012;36(10):1267-73.

Rokosz et al., "Kinase inhibitors as drugs for chronic inflammatory and immunological diseases: progress and challenges," Expert Opin Ther Targets. 2008; 12(7):883-903.

Ronnebaum et al., "Synthesis of 1, 2, 3-triazole 'click' analogues of thalidomide," Tetrahedron. 2016;72(40): 6136-6141.

Ross et al., "Bispecific T cell engager (BITE®) antibody constructs can mediate bystander tumor cell killing," PLoS ONE. 2017; 12(8): e0183390.

Rostovtsev et al., "A Stepwise Huisgen Cycloaddition Process: Copper(I)-Catalyzed Regioselective "Ligation" of Azides and Terminal Alkynes," Angew Chem Int Ed Engl. 2002, 41(14):2596-2599.

Rusnac et al., "Recognition of the Diglycine C-End Degron by CRL2 KLHDC2 Ubiquitin Ligase," Mol. Cell. 2018, 72(5):813-822.e4.

Schnekloth et al., "Chemical Approaches to Controlling Intracellular Protein Degradation," Chembiochem, 2005, 6(1):40-46.

Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017, 60(24): 10071-10091.

Seganish et al., "Discovery and Structure Enabled Synthesis of 2,6-diaminopyrimidine-4-one IRAK4 Inhibitors," ACS Med Chem Lett. 2015, 6(8):942-947.

Seganish et al., "Initial optimization and series evolution of diaminopyrimidine inhibitors of interleukin-1 receptor associated kinase 4," Bioorg Med Chem Lett. 2015, 25(16):3203-3207.

Seitz et al., "Sulfenylation and Halogenation of Di-and Trianions Derived from Substituted Glutarimides," Synthetic Communications, 1977, 7(6):367-374.

Sen et al., "Transcriptional signaling by double-stranded RNA: role of TLR3," Cytokine Growth Factor Rev., 2005, 16(1):1-14.

Shanmugasundaram et al., "A modular PROTAC design for target destruction using a degradation signal based on a single amino acid," J Biol Chem. 2019, 294(41):15172-15175.

Smith et al., "Identification of quinazoline based inhibitors of IRAK4 for the treatment of inflammation," Bioorg Med Chem Lett., 2017, 27(12):2721-2726.

So et al., "A pilot study of IL-1 inhibition by anakinra in acute gout," Arthritis Res Ther., 2007, 9(2):R28.

Song et al., "The kinase activities of interleukin-e receptor associated kinase (IRAK)-1 and 4 are redundant in the control of inflammatory cytokine expression in human cells," Mol Immunol. 2009, 46(7):1458-66.

Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.

Spratt et al., "RBR E3 ubiquitin ligases: new structures, new insights, new question," Biochem J., 2014, 458(3):421-437.

Stewart et al., "Efforts toward elucidating Thalidomide's molecular target: an expedient synthesis of the first Thalidomide biotin analogue," Organic & Biomolecular Chemistry, 2010, 8(18): 4059-4062.

Sun et al., "Carbohydrate and protein immobilization onto solid surfaces by sequential Diels-Alder and azide-alkyne cycloadditions," Bioconjug Chem., 2006, 17(1):52-57.

Suzuki et al., "IRAK-4 as the central TIR signaling mediator in innate immunity," Trends Immunol. 2002, 23(10):503-506.

Suzuki et al., "Severe impairment of interleukin-1 and Toll-like receptor signalling in mice lacking IRAK-4," Nature, 2002, 416(6882):750-756.

Swantek et al., "IL-1 Receptor-Associated Kinase Modulates Host Responsiveness to Endotoxin," Journal of Immunology, 2000, 164(8):4301-4316.

Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009, 68(10):1613-1617.

Terkeltaub, "Update on gout: new therapeutic strategies and options," Nat Rev Rheumatol. 2010, 6(1):30-38.

Tong et al., "Targeted Protein Degradation via a Covalent Reversible Degrader Based on Bardoxolone", ChemRxiv. First Posted Online: Apr. 2, 2020, 23 pages.

Toogood, "Small molecule immuno-oncology therapeutic agents," Bioorg. Med. Chem. Lett., 2018, 28(3):319-329.

Torres et al., "Hyperalgesia, synovitis and multiple biomarkers of inflammation are suppressed by interleukin 1 inhibition in a novel animal model of gouty arthritis," Ann Rheum Dis., 2009, 68(10):1602-1608.

Toure and Crews, "Small-Molecule PROTACS: New Approaches to Protein Degradation," Angew Chem Int Ed Engl., 2016, 55(6):1966-1973.

Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].

Trøseid et al., "The role of interleukin-18 in the metabolic syndrome," Cardiovasc Diabetol., 2010, 9:11.

Tumey et al., "Identification and optimization of indolo[2,3-c]quinoline inhibitors of IRAK4," Bioorg Med Chem Lett., 2014, 24(9):2066-2072.

Uehara et al., "Selective degradation of splicing factor CAPER? by anticancer sulfonamides," Nat Chem Biol., 2017, 13(6):675-680.

Varfolomeev et al., "IAP antagonists induce autoubiquitination of c-IAPs, NF-kappaB activation, and TNFalpha-dependent apoptosis," Cell, 2007, 131(4):669-681.

Vollmer et al., "The mechanism of activation of IRAKl and IRAK4 by interleukin-1 and Toll-like receptor agonists," Biochem J., 2017, 474(12):2027-2038.

Wang et al., "Crystal Structure of IRAK-4 Kinase in Complex with Inhibitors: Serine/Threonine Kinase with Tyrosine as a Gatekeeper," Structure, 2006, 14(12):1835-1844.

Wang et al., "Discovery of potent, selective, and orally bioavailable inhibitors of interleukin-1 receptor-associated kinase 4," Bioorg Med Chem Lett, 2015, 25(23):5546-5550.

Wang et al., "IRAK-4 Inhibitors for Inflammation," Curr Top Med Chem., 2009, 9(8):724-37.

(56) References Cited

OTHER PUBLICATIONS

Wang et al., "Roles of F-box proteins in cancer," Nat Rev Cancer., 2014, 14(4):233-47.
Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med., 2008, 75(Suppl 5):S9-12.
Winter et al., "Selective Target Protein Degradation via Phthalimide Conjugation," Science., 2015, 348(6241):1376-1381.
Xia and Chen, "Iron-catalyzed N-alkylation of azoles via cleavage of an sp3 C—H bond adjacent to a nitrogen atom," J Org Chem., 2012, 77(20):9366-9373.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-κB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell, 2012, 21(6):723-737.
Zhang et al., "Constitutive IRAK4 Activation Underlies Poor Prognosis and Chemoresistance in Pancreatic Ductal Adenocarcinoma," Clin Cancer Res., 2017, 23(7):1748-1759.
Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., "Targets of curcumin," Curr Drug Targets., 2011, 12(3):332-347.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockage for cancer therapy: Mechanisms, response biomarkers, and combinations," Sci Transl. Med. 2016;8(328):328rv4.
PCT International Search Report received from PCT/US2023/061673, dated Jul. 25, 2023, 4 pages.
PCT International Preliminary Report on Patentability received from PCT/US2022/070662, dated Augusy 24, 2023.
McElroy, "Interleukin-1 receptor-associated kinase 4 (IRAK4) inhibitors: an updated patent review (2016-2018)," Expert Opinion On Therapeutic Patents, 2019, 29(4):243-259.
International Search Report and Written Opinion from PCT/US2023/083863, dated Apr. 2, 2024.

* cited by examiner

| ng/mL (plasma) ng/g (skin) | 25 mg QD (n=9) | 50 mg QD (n=9) | 100 mg QD (n=9) | 200 mg QD (n=9) |
|---|---|---|---|---|
| Plasma Day 7 | 3.21 | 7.15 | 11.9 | 18.2 |
| Plasma Day 14 | 4.72 | 8.49 | 11.6 | 17.4 |
| Skin Day 7 | 21.5 | 40.2 | 53.5 | 80.9 |
| Skin Day 14 | 44.5 | 94.2 | 93.7 | pending |

IRAK4 DEGRADERS AND USES THEREOF

CROSS-REFERENCE TO RELATED APPLICATIONS

This application claims the benefit of U.S. Provisional Appl No. 63/149,621, filed Feb. 15, 2021, U.S. Provisional Appl. No. 63/263,055, filed Oct. 26, 2021, and U.S. Provisional Appl. No. 63/265,466, filed Dec. 15, 2021, the entirety of each of which is herein incorporated by reference.

TECHNICAL FIELD OF THE INVENTION

The present invention relates to formulation and dosage forms of IRAK4 degrader 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide (Compound A), and methods of use thereof.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

UPP plays a key role in the degradation of short-lived and regulatory proteins important in a variety of basic cellular processes, including regulation of the cell cycle, modulation of cell surface receptors and ion channels, and antigen presentation. Interleukin-1 receptor-associated kinase-4 (IRAK4) is a key component of the myddosome, a multi-protein complex involved in innate immunity that mediates signaling through toll-like receptors (TLRs) and interleukin (IL)-1 receptors (Patra and Choi, Molecule 2016, 21(11): 1529). The IRAK4 protein is ubiquitously expressed across multiple different tissue types, including skin, lymphoid tissue, bone marrow, gastrointestinal (GI) tract and lung. The function of IRAK4 is dependent both on its kinase activity and on its scaffolding properties, which is required for the assembly of the myddosome complex following TLR or IL-1R engagement and myeloid differentiation factor 88 (MyD88) activation (De Nardo et al., J. Bio. Chem. 2018, 293(39):15195; Cushing et al., J. Bio. Chem. 2014, 289(15): 10865). The NF-kB activation is particularly dependent on the scaffolding function of IRAK4 and is a key driver of cellular proliferation and proinflammatory cytokine and chemokine production mediated by myddosome activation.

There are numerous cutaneous, rheumatic, and GI autoinflammatory/autoimmune disease indications whose pathogenesis involves IL-1 family cytokines as well as TLR stimulation and where the pleiotropic effects of an IRAK4 degrader on these pathways can provide a significant advantage over current treatment options. Further there are multiple cutaneous indications where there is clinical proof of concept for targeting the IL-1R/TLR pathway but continued high unmet need for more effective therapeutics.

SUMMARY OF THE INVENTION

It has been found that IRAK4 degrader 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide (Compound A) formulations and unit dosage forms of the invention have certain advantages in treating autoimmune/autoinflammatory diseases.

In one embodiment of the present disclosure, there is provided a spray-dried formulation comprising Compound A or a pharmaceutically acceptable salt thereof, and a pharmaceutically acceptable polymer. In some aspects, the spray-dried formulation comprises Compound A free base. In other aspects, the spray-dried formulation comprises Compound A HCl. In some instances, the pharmaceutically acceptable polymer is selected from PVP-VA, HPMC, HPMCP-55, HPMCAS-M, TPGS, HPMCAS-L, and MCC, preferably HPMCAS-M. The spray-dried formulation may include about 20-40% wt/wt Compound A, or a pharmaceutically acceptable salt thereof and about 60-80% wt/wt of pharmaceutically acceptable polymer. In certain aspects, the spray-dried formulation comprises 25:75 (% wt/wt) Compound A free base: HPMCAS-M.

In one embodiment of the present disclosure, there is provided a unit dosage form comprising the spray-dried formulation disclosed herein. In some aspects, the spray-dried formulation is about 45-55% wt/wt of the unit dosage form. In other aspects, the unit dosage form further comprises a filler, wherein the filler is selected from mannitol, microcrystalline cellulose, or a mixture thereof. In certain aspects, the unit dosage form further comprises a glidant, wherein the glidant is colloidal silicon dioxide. In certain aspects, the unit dosage form further comprises a disintegrant, wherein the disintegrant is croscarmellose sodium. In certain aspects, the unit dosage form further comprises a solubility enhancer, wherein the solubility enhancer is hydroxypropyl-beta-cyclodextrin (HPβCD). In certain aspects, the unit dosage form further comprises a lubricant, wherein the lubricant is stearyl fumarate sodium.

In another embodiment of the present compositions and methods, the unit dosage form comprises 10-500 mg of Compound A or a pharmaceutically acceptable salt thereof, for example, the unit dosage form comprises 25 mg or 100 mg of Compound A or a pharmaceutically acceptable salt thereof.

In further embodiments of the present disclosure, there is provided a method for treating an autoimmune/autoinflammatory disease or a hematological malignancy in a patient, comprising administering (e.g., orally) to the patient a therapeutically effect amount of the spray-dried formulation or the unit dosage form described herein In some aspects, the autoimmune/autoinflammatory disease is selected from a cutaneous, rheumatic, and gastrointestinal autoimmune/autoinflammatory disease. In some aspects, the autoimmune/autoinflammatory disease is a cutaneous autoimmune/autoinflammatory disease selected from atopic dermatitis (AD) and hidradenitis suppurativa (HS).

In some embodiments, the method comprises administering (e.g., orally) up to about 1600 mg of Compound A or a pharmaceutically acceptable salt thereof to a patient, such as up to about 1400 mg (e.g., per day). In some aspects, the method comprises administering about 25-1400 mg (for example, about 25 mg, about 50 mg, about 75 mg, about 100 mg, about 150 mg, about 200 mg, about 300 mg, about 400 mg, about 500 mg, about 600 mg, about 800 mg, about 1000 mg, about 1200 mg, or about 1400 mg) of compound A or a pharmaceutically acceptable salt thereof to a patient (e.g., per day).

These and other aspects of this disclosure will be apparent upon reference to the following detailed description. To this end, various references are set forth herein which describe in more detail certain background information and procedures and are each hereby incorporated by reference in their entirety.

DETAILED DESCRIPTION OF THE INVENTION

Figure 1:
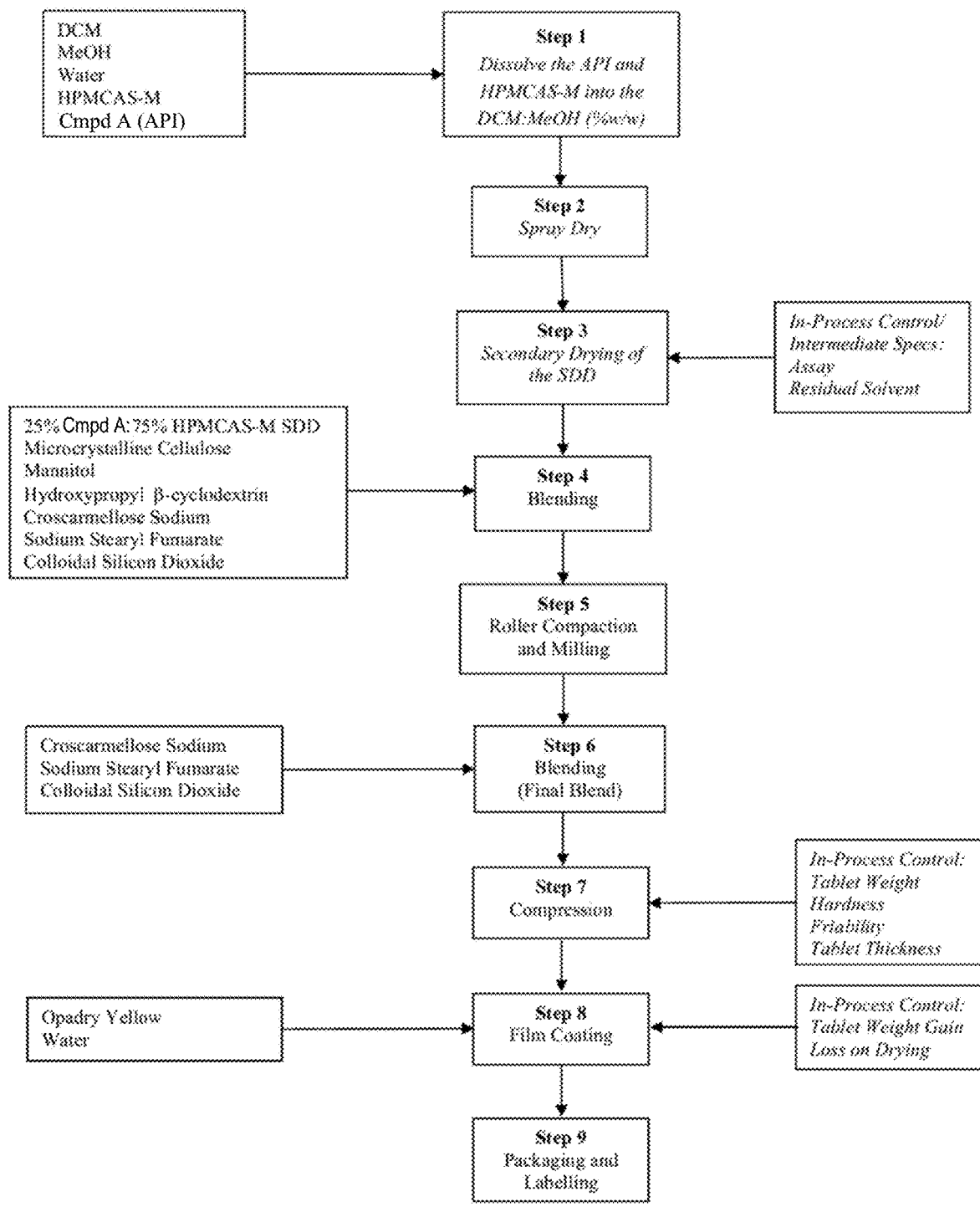
FIG. 1 depicts a manufacturing process flow diagram describing the operations involved in the manufacture of 25% Compound A:75% HPMCAS-M SDD and the Compound A 25 mg and 100 mg film coated tablets.
Figure 2:
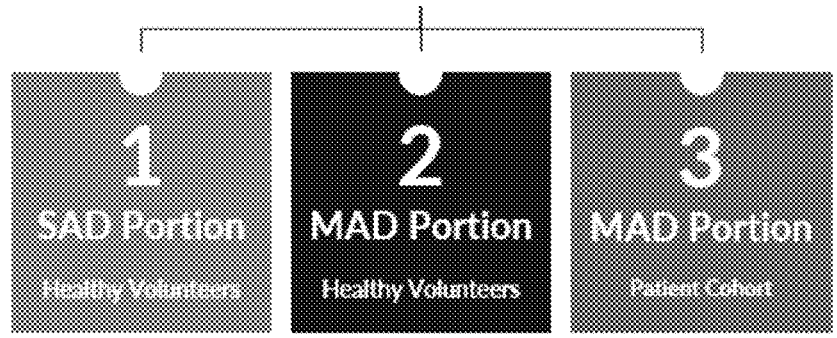
FIG. 2 depicts the Compound A Phase 1 trial design including double-blind, placebo-controlled, single ascending dose (SAD) and multiple ascending dose (MAD) trials.

1. General Description of Certain Embodiments of the Invention

Compound A is a potent, highly selective, orally administered heterobifunctional small molecule therapeutic targeting IRAK4 and the E3 ligase CRBN to mediate the selective degradation of IRAK4 via the ubiquitin-proteasome system.

Compound A is composed of a CRBN-targeting ligand and an IRAK4-targeting ligand joined by a chemical linker. Compound A forms a ternary complex through non-covalent binding to both CRBN and IRAK4, bringing the E3 ligase (CRBN) in close proximity to IRAK4, that now serves as its neosubstrate. This proximity leads to IRAK4 ubiquitination and proteasomal degradation and eventual release of Compound A, which is then free to mediate additional rounds of ternary complex formation and IRAK4 degradation.

In vitro and in vivo studies confirmed the ability of Compound A to selectively degrade its intended target, IRAK4, and to inhibit downstream production of disease relevant proinflammatory cytokines and chemokines. In vitro, Compound A's ability to degrade IRAK4 across species was confirmed in a study of mouse and rat splenocytes and dog, monkey, and human PBMCs, where similar $DC_{50}$ values were observed across all species (<10 nM). Across a series of in vitro studies in human peripheral blood mononuclear cells (PBMCs), whole blood, and OCI-LY10 cells, Compound A robustly reduced IRAK4 levels, with $DC_{50}$ values consistently in the low nM range. Multiple in vitro cytokine release assays confirmed Compound A's ability to inhibit TLR agonist (lipopolysaccharide and R848) and IL-1β-induced proinflammatory cytokine production (including IL-6, TNF-α, granulocyte-macrophage colony-stimulating factor, and IL-8) in PBMCs with IC50 values also in the low nM range. Lastly, mass spectrometry (MS) proteomic analysis of PBMCs treated with Compound A demonstrated the compound's selectivity for its target, with IRAK4 being the only protein degraded of more than 9,000 proteins sampled.

In vivo, murine models of inflammation demonstrated the ability of Compound A-induced IRAK4 degradation to impact TLR- and IL-1β-mediated Th1 and Th17 inflammation as well as neutrophil migration. In the mouse air pouch model of MSU-crystal induced (TLR 2/4-dependent) inflammation, 3 days twice daily administration of Compound A at doses ranging from 30 to 100 mg/kg not only significantly reduced IRAK4 levels in the spleen, but also significantly reduced the inflammatory exudate, including reduction of neutrophils and IL-1β. Similar findings were observed in the imiquimod psoriasis model (TLR 7/8-dependent), where administration of Compound A resulted in dose-dependent degradation of IRAK4 in the spleen and skin associated with reduction in skin thickness as well as significant reduction of IL-1β($p<0.0001$) and IL-6 ($p<0.05$; 300 mg/kg only) in the skin. Overall, efficacy was associated with achieving at least 80% or more IRAK4 knockdown in associated tissues in the model systems.

In vivo pharmacokinetics (PK)/pharmacodynamics (PD) studies in mice and dogs demonstrated potent IRAK4 degradation by Compound A. In wild-type mice, a single oral dose of Compound A at 300 mg/kg resulted in nearly 100% degradation of IRAK4 in the skin and approximately 66% degradation in the spleen, which was sustained for at least 48-hour post-dose. In both the skin and spleen, maximal PD effects were achieved after tmax at each dose level. In dogs, 7 days of oral administration at doses up to 10 mg/kg/day also led to marked reduction of IRAK4 in the skin and in PBMCs, with Compound A trough plasma concentration levels as low as 3 nM inducing >85% degradation of IRAK4 in the PBMCs and degradation below the limit of quantitation in the skin. Recovery of IRAK4 levels was noted by 96 to 168 hr following last dose in dogs, demonstrating the reversible nature of Compound A induced degradation. Together, these studies point to the potent, on-target, and reversible effects of Compound A against IRAK4.

In in vivo pharmacokinetic (PK) studies conducted in rats, dogs, and monkeys, Compound A PK was characterized by moderate to high clearance, high volume of distribution at steady state, a moderate terminal half-life, and low to moderate bioavailability. Compound A exhibited low solubility, moderate permeability, and was identified as a substrate of P-glycoprotein (P-gp) and breast cancer resistance protein (BCRP) in vitro. Compound A was highly bound to plasma proteins across nonclinical species and humans and did not significantly partition into red blood cells. In distribution studies in rats, Compound A extensively distributed into tissues, but had limited penetration into the central nervous system (CNS).

In vitro and in vivo metabolism studies showed that Compound A underwent oxidative metabolism via cytochrome P450 (CYP). An excretion study conducted in bile duct-cannulated (BDC) rats showed negligible renal clearance of Compound A, and minor to moderate biliary and intestinal excretion as parent drug. Metabolites generated in liver microsomes from humans were also detected in those from rat, dog, and monkey. In the in vitro drug-drug interaction studies, Compound A demonstrated potential time dependent inhibition (TDI) of CYP2C19 and CYP3A4 and inhibited BCRP efflux, and therefore has the potential to be a perpetrator to sensitive CYP2C19, CYP3A4, and BCRP substrates. Conversely, Compound A is primarily metabolized by CYP3A4 and is substrate of P-gp and BCRP and has the potential to be a victim when co-dosing with strong or moderate inhibitors or inducers of the enzymes.

Accordingly, in some embodiments, the present disclosure provides a method for treating a cutaneous autoimmune/autoinflammatory disease in a patient, such as atopic dermatitis (AD) and hidradenitis suppurativa (HS), comprising administering to the patient a therapeutically effective amount of Compound A, or a pharmaceutically acceptable salt thereof.

In some embodiments, the present disclosure provides a method for treating AD in a patient, comprising administering to the patient a therapeutically effective amount of Compound A, or a pharmaceutically acceptable salt thereof.

In some embodiments, the present disclosure provides a method for treating HS in a patient, comprising administering to the patient a therapeutically effective amount of Compound A, or a pharmaceutically acceptable salt thereof.

In some embodiments, the present disclosure provides a formulation and a unit dosage form as described herein, which comprise Compound A, or a pharmaceutically acceptable salt thereof.

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

2. Definitions

As used in the specification and appended claims, unless specified to the contrary, the following terms and abbreviations have the meaning indicated:

"Compound A" refers to IRAK4 degrader 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide, of formula:

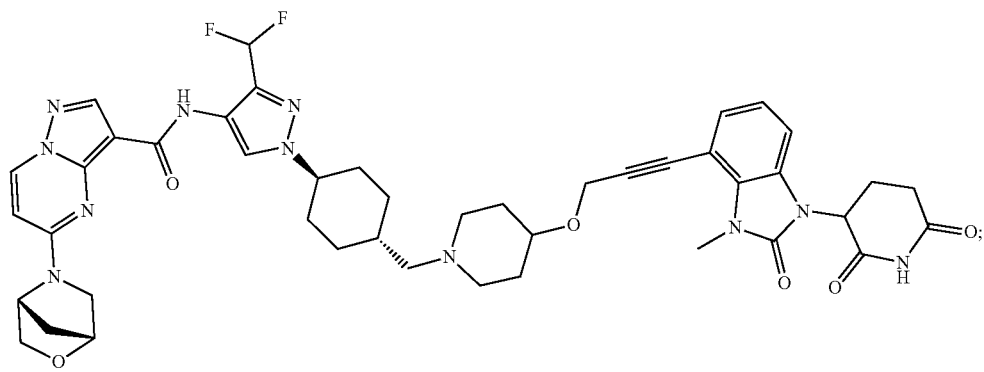 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

"Compound B" refers to IRAK4 degrader 5-((1R,4R)-2-oxa-5-azabicyclo[2.2.1]heptan-5-yl)-N-(3-(difluoromethyl)-1-((1r,4R)-4-((4-((3-(1-((S)-2,6-dioxopiperidin-3-yl)-3-methyl-2-oxo-2,3-dihydro-1H-benzo[d]imidazol-4-yl)

prop-2-yn-1-yl)oxy)piperidin-1-yl)methyl)cyclohexyl)-1H-pyrazol-4-yl)pyrazolo[1,5-a]pyrimidine-3-carboxamide, of formula:

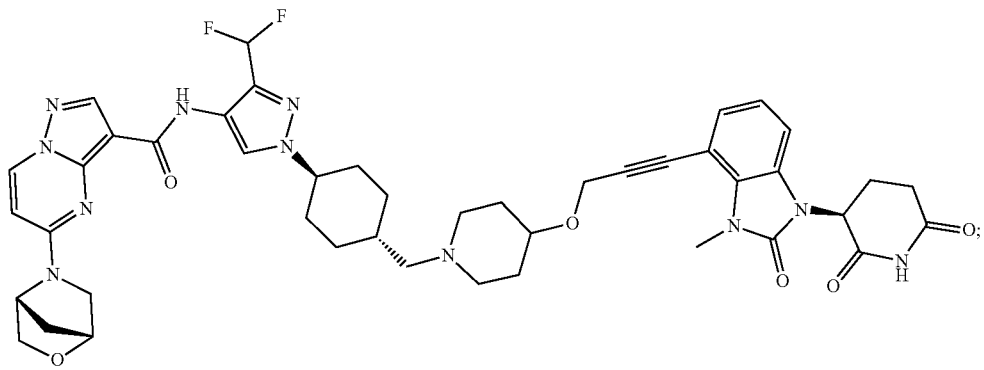 [SMILES: Cn1c(=O)n([C@H]2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

and "Compound C" refers the IRAK4 degrader 5-((1R,4R)-2-oxa-5-azabicyclo[2.2.1]heptan-5-yl)-N-(3-(difluoromethyl)-1-((1r,4R)-4-((4-((3-(1-((R)-2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide, of formula:

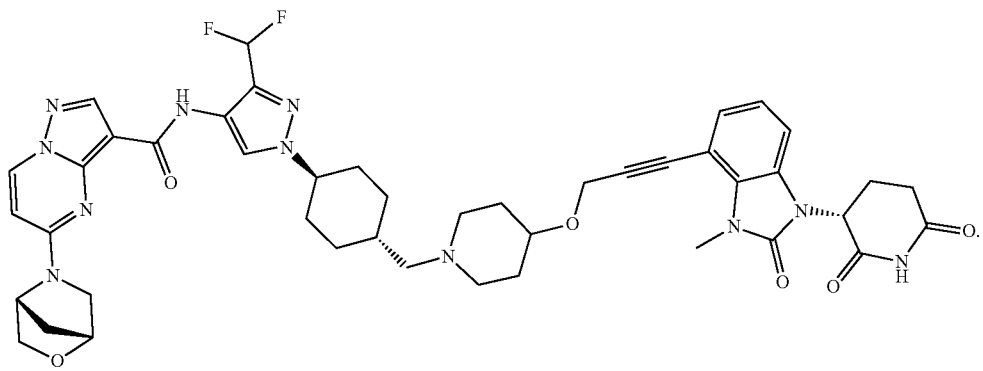 [SMILES: Cn1c(=O)n([C@@H]2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

The molecular structure of Compound A contains three chiral centers, including two fixed/stable centers around the morpholine ring (RR) and one epimerizable chiral center (R/S) resulting in the two diastereomers, (S,R,R)-Compound A and (R,R,R)-Compound A, which are designated as Compound B and Compound C, respectively. In some embodiments, Compound A is Compound B. In some embodiments, Compound A is Compound C. In some embodiments, Compound A is a mixture of Compound B and Compound C. In some embodiments, Compound A is an approximately 1:1 mixture of Compound B and Compound C. Both diastereomers interconvert rapidly in vitro and in vivo. In some embodiments, Compound A, Compound B, Compound C, or a pharmaceutically acceptable salt thereof, is amorphous. In some embodiments, Compound A, Compound B, Compound C, or a pharmaceutically acceptable salt thereof, is in crystal form.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^{+}(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the terms "about" or "approximately" have the meaning of within 20% of a given value or range. In some embodiments, the term "about" refers to within 20%, 19%, 18%, 17%, 16%, 15%, 14%, 13%, 12%, 11%, 10%, 9%, 8%, 7%, 6%, 5%, 4%, 3%, 2%, or 1% of a given value.

3. Description of Exemplary Methods and Uses

In some embodiments, the present invention provides a method for treating an autoimmune/autoinflammatory disease or a hematological malignancy in a patient, comprising administering to the patient a therapeutically effective amount of Compound A, or a pharmaceutically acceptable salt thereof. In some embodiments, the autoimmune/autoinflammatory disease is a cutaneous autoimmune/autoinflammatory disease.

In some embodiments, the present disclosure provides a method for treating a cutaneous autoimmune/autoinflammatory disease in a patient, such as atopic dermatitis (AD) and hidradenitis suppurativa (HS), comprising administering to the patient a therapeutically effective amount of Compound A, or a pharmaceutically acceptable salt thereof.

In some embodiments, the present disclosure provides a method for treating AD in a patient, comprising administering to the patient a therapeutically effective amount of Compound A, or a pharmaceutically acceptable salt thereof.

In some embodiments, the present disclosure provides a method for treating HS in a patient, comprising administering to the patient a therapeutically effective amount of Compound A, or a pharmaceutically acceptable salt thereof.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, a patient or subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment or therapy.

A "therapeutically effective amount" or "therapeutically effective dosage" of a drug or therapeutic agent, such as Compound A, is any amount of the drug that, when used alone or in combination with another therapeutic agent, protects a patient or subject against the onset of a disease, such as AD, or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

In preferred embodiments, a therapeutically effective amount of the drug, such as Compound A, promotes regression to the point of eliminating the disease. In addition, the terms "effective" and "effectiveness" with regard to a treatment includes both pharmacological effectiveness and physiological safety. Pharmacological effectiveness refers to the ability of the Compound A to treat the disease in the patient. Physiological safety refers to the level of toxicity, or other adverse physiological effects at the cellular, organ and/or organism level (adverse effects) resulting from administration of the drug.

As used herein, the terms "therapeutic benefit" or "benefit from therapy" refers to an improvement in one or more of overall survival, progression-free survival, partial response, complete response, and overall response rate and can also include a decrease in severity of disease symptoms, an increase in frequency and duration of disease symptom-free periods, or a prevention of impairment or disability due to the disease affliction.

The term "patient," as used herein, means an animal, preferably a mammal, and most preferably a human.

The term "subject," as used herein, has the same meaning as the term "patient".

In some embodiments, a patient is 18 years or older, such as from 18 to 55 years old (inclusive) at the time of screening, and generally good health, except for AD or HS. In some embodiments, "good health" is defined as no clinically relevant abnormalities identified by a detailed medical history, physical examination, including BP and PR measurement, 12-lead ECG, and clinical laboratory tests.

In some embodiments, a patient has a diagnosis of AD or HS for at least 6 months prior to Day 1. In some embodiments, the patient with AS has at least 25% treatable percentage body surface area at screening or on admission (excluding the scalp and designated venous access areas). In some embodiments, a patient has an Investigator's static global assessment score of moderate (3) or severe (4) at Screening or on Day −1. In some embodiments, a patient has a BMI of 17.5 to 35.0 kg/m$^2$; and a total body weight >50 kg (110 lb).

In some embodiments, a patient does not have any clinically significant medical disorder, condition, disease (including active or potentially recurrent dermatological conditions other than AD or HS), significant physical examination or laboratory findings that may interfere with study objectives, in the Investigator's opinion (e.g., conditions or findings that may expose a patient to unacceptable risk by study participation, confound the evaluation of treatment response or adverse events, or otherwise interfere with a patient's ability to complete the study).

In some embodiments, a patient does not have unstable AD or HS or a consistent requirement for strong to strongest potency topical corticosteroids to manage AD or HS signs and symptoms. In some embodiments, a patient does not have active systemic or localized infection, including known actively-infected AD or HS. In some embodiments, a patient does not have a history or evidence of clinically significant or severe allergies (eg, seasonal, pet-dander, environmental, food) requiring acute or chronic treatment (patients with allergic rhinitis who do not require treatment, or for whom an ongoing allergy treatment meets the definition of a stable regimen under Concomitant Treatment(s) section, may be eligible to participate in the study). In some embodiments, a patient does not have a history of recent (within 4-weeks of Day 1) sunbathing, tanning bed use, or ultraviolet (UV) light B therapy or psoralen plus UV A (sunbathing, tanning bed use, and UV light therapy are prohibited during the study). In some embodiments, a patient does not have any planned surgical or medical procedure that would overlap with study participation from Screening through the end of study. In some embodiments, a patient does not have any cancer or have a history of cancers within the last 5 years (except curatively treated with surgical excised squamous cell carcinoma, basal cell carcinoma, or carcinoma in situ of the skin or cervix). In some embodiments, a patient does not have a known sensitivity to any of the components of the investigational product. In some embodiments, a patient does not have a positive urine drug test. In some embodiments, a patient does not have a history of regular alcohol consumption exceeding 7 drinks/week for female patients or 14 drinks/week for male patients (1 drink=5 ounces [150 mL] of wine or 12 ounces [360 mL] of beer or 1.5 ounces [45 mL] of hard liquor) within 6 months before Screening. In some embodiments, a patient has not received treatment with an investigational product within 30 days or 5 half-lives preceding the first dose of investigational product (whichever is longer). In some embodiments, a patient has not received treatment with CYP3A4 and P-gp inhibitors within 30 days or 5 half-lives preceding the first dose of investigational product (whichever is longer). In some embodiments, a patient does not have screening supine BP ≥140 mm Hg (systolic) or ≥90 mm Hg (diastolic), following at least 5 minutes of supine rest. If BP is ≥140 mm Hg (systolic) or ≥90 mm Hg (diastolic), the BP should be repeated 2 more times and the average of the 3 BP values should be used to determine the patient's eligibility. In some embodiments, a patient does not have screening supine 12-lead ECG demonstrating a QTc interval >450 msec or a QRS interval >120 msec. If QTc exceeds 450 msec, or QRS exceeds 120 msec, the ECG should be repeated 2 more times and the average of the 3 QTc or QRS values should be used to determine the patient's eligibility. In some embodiments, a patient does not have any of the following abnormalities in clinical laboratory tests at Screening, as assessed by the study-specific laboratory and confirmed by a single repeat test, if deemed necessary: a) Aspartate aminotransferase or ALT level ≥1.5× ULN; b) Total bilirubin level ≥1.5×ULN; patients with a history of Gilbert's syndrome may have direct bilirubin measured and would be eligible for this study provided the direct bilirubin level is ≤ULN. In some embodiments, a patient does not use prescription or nonprescription drugs including topical corticosteroids, vitamin and dietary supplements within 14-days or 5 half-lives (whichever is longer) prior to the first dose of investigational product. As an exception, acetaminophen/paracetamol may be used (only if necessary) at doses of ≤1 g/day. Limited use of nonprescription medications that are not believed to affect patient safety or the overall results of the study may be permitted on a case-by-case basis following approval by the Sponsor. Herbal supplements (including St. John's Wort) must have been discontinued at least 28-days prior to the first dose of investigational product. In some embodiments, a patient has not donated blood (excluding plasma donations and platelet donations) of approximately ≥400 mL within 3 months or ≥200 mL within a month prior to dosing. In some embodiments, a patient does not have a history of sensitivity to heparin or heparin-induced thrombocytopenia. In some embodiments, a patient does not have a history of HIV, hepatitis B, hepatitis C, or syphilis; positive testing for HIV, hepatitis B virus surface antigen, hepatitis B virus core antibody, hepatitis C virus antibody, syphilis, or SARS-CoV-2 infection.

In some embodiments, a method of the present invention comprises orally administering a formulation as described herein. In some embodiments, a method of the present invention comprises administering a unit dosage form as described herein. In some embodiments, a method of the present invention comprises administering daily to a patient a formulation or a unit dosage form as described herein.

In some embodiments, a method of the present invention comprises administering daily to a patient up to about 1600 mg of Compound A, or a pharmaceutically acceptable salt thereof, for example up to about 25 mg, up to about 50 mg, up to about 75 mg, up to about 100 mg, up to about 150 mg, up to about 200 mg, up to about 300 mg, up to about 400 mg, up to about 500 mg, up to about 600 mg, up to about 800 mg, up to about 1000 mg, up to about 1200 mg, or up to about 1400 of Compound A, or a pharmaceutically acceptable salt thereof. In some embodiments, a method of the present invention comprises administering daily to a patient about 25-1400 mg (for example, about 50-1400 mg, about 75-1400 mg, about 100-1400 mg, about 150-1400 mg, about 300-1400 mg, about 600-1400 mg, about 25-1000 mg, about 50-1000 mg, about 75-1000 mg, about 100-1000 mg, about 150-1000 mg, or about 300-1000 mg) of compound A, or a pharmaceutically acceptable salt thereof. In some embodiments, a method of the present invention comprises administering daily to a patient about 25-500 mg (for example, about 50-500 mg, about 75-500 mg, about 100-500 mg, about 150-500 mg, about 300-500 mg, about 25-250 mg, about 50-250 mg, about 75-250 mg, about 100-250 mg, or about 150-250 mg) of compound A, or a pharmaceutically acceptable salt thereof. In some embodiments, a method of the present invention comprises administering daily to a patient about 25 mg of Compound A, or a pharmaceutically acceptable salt thereof, for example as a single 25 mg unit dosage form. In some embodiments, a method of the present invention comprises administering daily to a patient about 50 mg of Compound A, or a pharmaceutically acceptable salt thereof, for example as two 25 mg unit dosage form. In some embodiments, a method of the present invention comprises administering daily to a patient about 75 mg of Compound A, or a pharmaceutically acceptable salt thereof, for example as three 25 mg unit dosage forms. In some embodiments, a method of the present invention comprises administering daily to a patient about 100 mg of Compound A, or a pharmaceutically acceptable salt thereof, for example as a single 100 mg unit dosage form. In some embodiments, a method of the present invention comprises administering daily to a patient about 150 mg of Compound A, or a pharmaceutically acceptable salt thereof, for example as a single 100 mg and two 25 mg unit dosage forms. In some embodiments, a method of the present invention comprises administering daily to a patient about 200 mg of Compound A, or a pharmaceutically acceptable salt thereof, for example as two 100 mg unit dosage forms. In some embodiments, a method of the present invention comprises administering daily to a patient about 300 mg of Compound A, or a pharmaceutically acceptable salt thereof, for example as three 100 mg unit dosage forms. In some embodiments, a method of the present invention comprises administering daily to a patient about 600 mg of Compound A, or a pharmaceutically acceptable salt thereof, for example as six 100 mg unit dosage forms. In some embodiments, a method of the present invention comprises administering daily to a patient about 1000 mg of Compound A, or a pharmaceutically acceptable salt thereof, for example as ten 100 mg unit dosage forms. In some embodiments, a method of the present invention comprises administering daily to a patient about 1400 mg of Compound A, or a pharmaceutically acceptable salt thereof, for example as fourteen 100 mg unit dosage forms. In some embodiments, a method of the present invention comprises administering a formulation or a unit dosage form as described herein once daily. In some embodiments, a method of the present invention comprises administering a formulation or a unit dosage form as described herein twice daily. In some embodiments, a method of the present invention comprises administering a formulation or a unit dosage form as described herein three times daily. In some embodiments, a method of the present invention comprises administering a formulation or a unit dosage form as described herein four to fourteen times daily.

In some embodiments, where the patient is administered daily about 600 mg of Compound A, or a pharmaceutically acceptable salt thereof, the dosing is twice daily or BID, i.e., two separate about 300 mg doses. In some embodiments, where the patient is administered daily about 600 mg of Compound A, or a pharmaceutically acceptable salt thereof, the dosing is thrice daily or TID, i.e., three separate about 200 mg doses. In some embodiments, where the patient is administered daily about 600 mg of Compound A, or a pharmaceutically acceptable salt thereof, the dosing is four-times daily or QID, i.e., four separate about 150 mg doses.

In some embodiments, where the patient is administered daily about 800 mg of Compound A, or a pharmaceutically acceptable salt thereof, the dosing is twice daily or BID, i.e., two separate about 400 mg doses. In some embodiments, where the patient is administered daily about 800 mg of Compound A, or a pharmaceutically acceptable salt thereof, the dosing is thrice daily or TID, i.e., three separate about 267 mg doses. In some embodiments, where the patient is administered daily about 800 mg of Compound A, or a pharmaceutically acceptable salt thereof, the dosing is four-times daily or QID, i.e., four separate about 200 mg doses.

In some embodiments, where the patient is administered daily about 1000 mg of Compound A, or a pharmaceutically acceptable salt thereof, the dosing is twice daily or BID, i.e., two separate about 500 mg doses. In some embodiments, where the patient is administered daily about 1000 mg of Compound A, or a pharmaceutically acceptable salt thereof, the dosing is thrice daily or TID, i.e., three separate about 333 mg doses. In some embodiments, where the patient is administered daily about 1000 mg of Compound A, or a pharmaceutically acceptable salt thereof, the dosing is four-times daily or QID, i.e., four separate about 250 mg doses.

In some embodiments, where the patient is administered daily about 1200 mg of Compound A, or a pharmaceutically acceptable salt thereof, the dosing is twice daily or BID, i.e., two separate about 600 mg doses. In some embodiments, where the patient is administered daily about 1200 mg of Compound A, or a pharmaceutically acceptable salt thereof, the dosing is thrice daily or TID, i.e., three separate about 400 mg doses. In some embodiments, where the patient is administered daily about 1200 mg of Compound A, or a pharmaceutically acceptable salt thereof, the dosing is four-times daily or QID, i.e., four separate about 300 mg doses.

In some embodiments, where the patient is administered daily about 1400 mg of Compound A, or a pharmaceutically acceptable salt thereof, the dosing is twice daily or BID, i.e., two separate about 700 mg doses. In some embodiments, where the patient is administered daily about 1400 mg of Compound A, or a pharmaceutically acceptable salt thereof, the dosing is thrice daily or TID, i.e., three separate about 467 mg doses. In some embodiments, where the patient is administered daily about 1400 mg of Compound A, or a pharmaceutically acceptable salt thereof, the dosing is four-times daily or QID, i.e., four separate about 350 mg doses.

In some embodiments, where the patient is administered daily about 1600 mg of Compound A, or a pharmaceutically acceptable salt thereof, the dosing is twice daily or BID, i.e., two separate about 800 mg doses. In some embodiments, where the patient is administered daily about 1600 mg of Compound A, or a pharmaceutically acceptable salt thereof, the dosing is thrice daily or TID, i.e., three separate about 533 mg doses. In some embodiments, where the patient is administered daily about 1600 mg of Compound A, or a pharmaceutically acceptable salt thereof, the dosing is four-times daily or QID, i.e., four separate about 400 mg doses.

In some embodiments, a method of the present invention comprises orally administering about 25 mg, about 50 mg, about 75 mg, about 100 mg, about 150 mg, about 200 mg, about 300 mg, about 400 mg, about 500 mg, about 600 mg, about 800 mg, about 1000 mg, about 1200 mg, or about 1400 of Compound A, or a pharmaceutically acceptable salt thereof, once a day in a single dose.

In certain embodiments, a method of the present invention comprises daily administering up to about 200 mg of Compound A, or a pharmaceutically acceptable salt thereof. In certain embodiments, a method of the present invention comprises daily administering up to about 200 mg of Compound A, or a pharmaceutically acceptable salt thereof. In certain embodiments, a method of the present invention comprises daily administering up to about 200 mg of Compound A, or a pharmaceutically acceptable salt thereof.

In some embodiments, a method of the present invention comprises administering a formulation or a unit dosage form as described herein, wherein there is about 4-24 hours between two consecutive administrations. In some embodiments, there is about 4, about 6, about 8, about 12, about 18, or about 24 hours between two consecutive administrations.

In some embodiments, a method of the present invention comprises administering a formulation or a unit dosage form as described herein, wherein there are about 1-7 days between two consecutive administrations. In some embodiments, there are about 1, about 2, about 3, about 4, about 5, about 6, or about 7 days between two consecutive administrations.

In some embodiments, a method of the present invention comprises administering a formulation or a unit dosage form as described herein, wherein there is about 1-4 weeks between two consecutive administrations. In some embodiments, there is about 1, about 2, about 3, or about 4 weeks between two consecutive administrations.

In some embodiments, the present disclosure provides a method of administering Compound A to a patient in need thereof, comprising administering to said patient a therapeutically effective amount of Compound A or a pharmaceutically acceptable salt thereof (e.g., in a formulation or a unit dose form as described herein), wherein a Cmax of up to about 50 ng/mL of Compound A in plasma is achieved. In some embodiments, the administration of Compound A or a pharmaceutically acceptable salt thereof (e.g., in a formulation or a unit dose form as described herein) achieves a Cmax of up to about 30 ng/mL of Compound A in plasma.

In some embodiments, a Cmax of Compound A in plasma includes about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, 40 ng/mL, 41 ng/mL, 42 ng/mL, 43 ng/mL, 44 ng/mL, 45 ng/mL, 46 ng/mL, 47 ng/mL, 48 ng/mL, 49 ng/mL, and 50 ng/mL, or any range of Cmax created by using two of the aforementioned concentrations as endpoints. In some embodiments, the method comprises administering Compound A or a pharmaceutically acceptable salt thereof (e.g., in a formulation or a unit dose form as described herein), wherein a Cmax of about 10 ng/mL to about 20 ng/mL, about 15 ng/mL to about 25 ng/mL, about 20 ng/mL to about 30 ng/mL, or about 25 ng/mL to about 35 ng/mL, of Compound A in plasma is achieved. In some embodiments, a Cmax of Compound A in plasma, as listed in Table 6 below, is achieved. In some embodiments, the method comprises daily administering Compound A or a pharmaceutically acceptable salt thereof (e.g., in a formulation or a unit dose form as described herein), wherein a Cmax of about 10 ng/mL to about 20 ng/mL, about 15 ng/mL to about 25 ng/mL, about 20 ng/mL to about 30 ng/mL, or about 25 ng/mL to about 35 ng/mL, of Compound A at Day 14 in plasma is achieved. In some embodiments, a Cmax of Compound A in plasma at Day 14, as listed in Table 9 below, is achieved.

In some embodiments, the present disclosure provides a method of administering Compound A to a patient in need thereof, comprising administering to said patient a therapeutically effective amount of Compound A or a pharmaceutically acceptable salt thereof (e.g., in a formulation or a unit dose form as described herein), wherein a tmax of Compound A in plasma is achieved in up to about 30 hours.

In some embodiments, a tmax of Compound A in plasma achieved includes about 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, 25 hrs, 26 hrs, 27 hrs, 28 hrs, 29 hrs, and 30 hrs, or any range of tmax created by using two of the aforementioned times as endpoints. In some embodiments, the method comprises administering Compound A or a pharmaceutically acceptable salt thereof (e.g., in a formulation or a unit dose form as described herein), wherein a tmax of Compound A in plasma is achieved in from about 5 hrs to about 15 hrs, about 10 hrs to about 20 hrs, or about 15 hrs to about 25 hrs. In some embodiments, a tmax of Compound A in plasma, as listed in Table 6 and Table 9 below, is achieved.

In some embodiments, the present disclosure provides a method of administering Compound A to a patient in need thereof, comprising administering to said patient a therapeutically effective amount of Compound A or a pharmaceutically acceptable salt thereof (e.g., in a formulation or a unit dose form as described herein), wherein an AUC of up to about 3000 ng*h/mL of Compound A in plasma is achieved.

In some embodiments, an AUC of Compound A in plasma includes about 100 ng*h/mL, 200 ng*h/mL, 300 ng*h/mL, 400 ng*h/mL, 500 ng*h/mL, 600 ng*h/mL, 700 ng*h/mL, 800 ng*h/mL, 900 ng*h/mL, 1000 ng*h/mL, 1100 ng*h/mL, 1200 ng*h/mL, 1300 ng*h/mL, 1400 ng*h/mL, 1500 ng*h/mL, 1600 ng*h/mL, 1700 ng*h/mL, 1800 ng*h/mL, 1900 ng*h/mL, 2000 ng*h/mL, 2100 ng*h/mL, 2200 ng*h/mL, 2300 ng*h/mL, 2400 ng*h/mL, 2500 ng*h/mL, 2600 ng*h/mL, 2700 ng*h/mL, 2800 ng*h/mL, 2900 ng*h/mL, and 3000 ng/mL, or any range of AUC created by using two of the aforementioned concentrations as endpoints. In some embodiments, the method comprises administering Compound A or a pharmaceutically acceptable salt thereof (e.g., in a formulation or a unit dose form as described herein), wherein an AUC of about 500 ng*h/mL to about 1000 ng*h/mL, about 1000 ng*h/mL to about 1500 ng*h/mL, about 1500 ng*h/mL to about 2000 ng*h/mL, or about 2000 ng*h/mL to about 2500 ng*h/mL, of Compound A in plasma is achieved. In some embodiments, the method comprises daily administering Compound A or a pharmaceutically acceptable salt thereof (e.g., in a formulation or a unit dose form as described herein), wherein an AUC of about 100 ng*h/mL to about 1000 ng*h/mL, about 150 ng*h/mL to about 800 ng*h/mL, about 200 ng*h/mL to about 600 ng*h/mL, or about 300 ng*h/mL to about 500 ng*h/mL, of Compound A in plasma is achieved. In some embodiments, an AUC of Compound A in plasma, as listed in Table 6 and Table 9 below, is achieved.

In some embodiments, the present disclosure provides a method of administering Compound A to a patient in need thereof, comprising administering to said patient a therapeutically effective amount of Compound A or a pharmaceutically acceptable salt thereof (e.g., in a formulation or a unit dose form as described herein), wherein a t1/2 of Compound A in plasma is from about 20 hrs to about 40 hours. In some embodiments, the t1/2 of Compound A in plasma is from about 20 hrs to about 30 hrs, about 25 hrs to about 35 hrs, or about 30 hrs to about 40 hrs. In some embodiments, a t1/2 of Compound A in plasma, as listed in Table 6 below, is achieved.

In some embodiments, the present disclosure provides a method of administering Compound A to a patient in need thereof, comprising administering to said patient a therapeutically effective amount of Compound A or a pharmaceutically acceptable salt thereof (e.g., in a formulation or a unit dose form as described herein), wherein greater than 80% of IRAK4 degradation in PBMCs is achieved (e.g., by measuring, at 48 hours post-administration, IRAK4 levels in PBMCs using mass spectrometry or lymphocytes and monocytes using flow cytometry). In some embodiments, administration of from about 150 mg to about 1600 mg of Compound A or a pharmaceutically acceptable salt thereof (e.g., in a formulation or a unit dose form as described herein) results in greater than 80% of IRAK4 degradation in PBMCs at 48 hours post-administration. In some embodiments, administration of from about 600 mg to about 1600 mg of Compound A or a pharmaceutically acceptable salt thereof (e.g., in a formulation or a unit dose form as described herein) results in greater than 90% of IRAK4 degradation in PBMCs at 48 hours post-administration. In some embodiments, an IRAK4 degradation in PBMCs, as listed in Table 4 or 7 below, is achieved.

Figure 11:
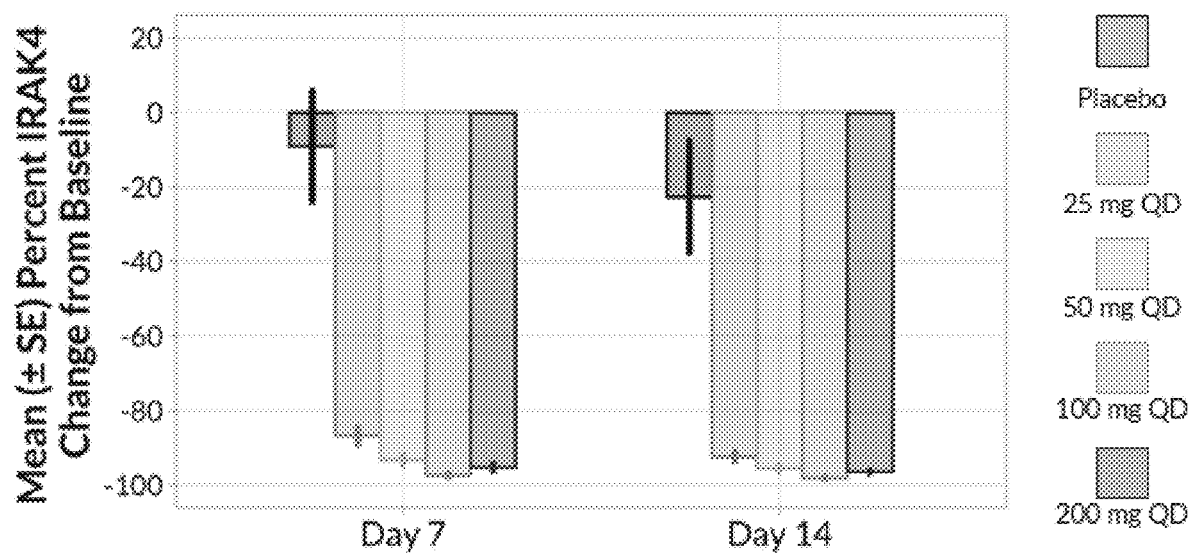
FIG. 11 shows that lower doses of Compound A achieve >98% IRAK4 degradation in PBMC in the MAD study.
Figure 12:
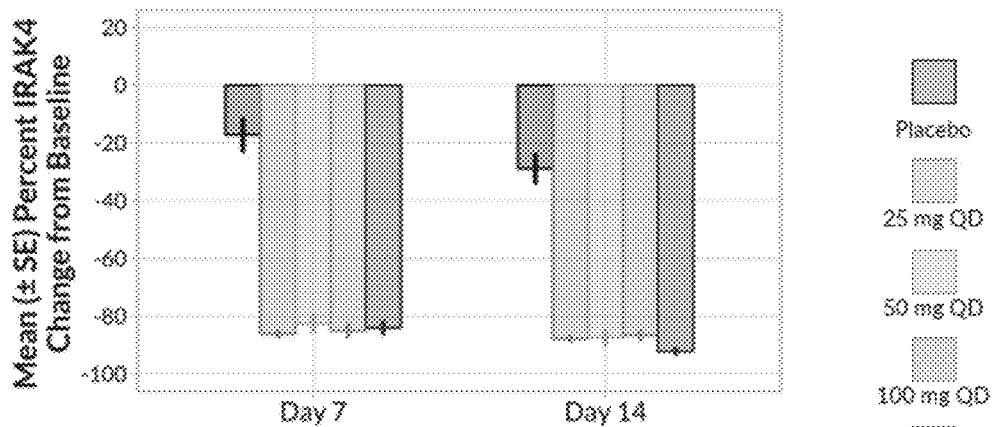
FIG. 12 shows that lower doses of Compound A achieved >90% IRAK4 degradation in lymphocytes and monocytes in the MAD study.
Figure 12:
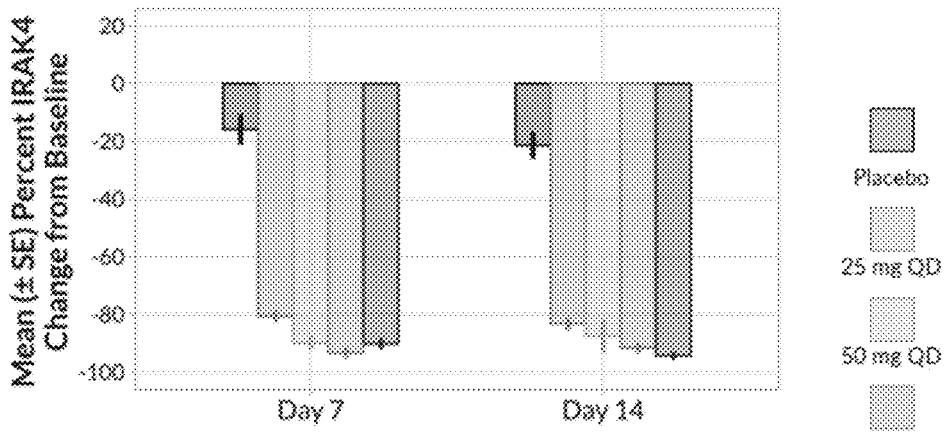

In some embodiments, the present disclosure provides a method of administering Compound A to a patient in need thereof, comprising daily administering to said patient a therapeutically effective amount of Compound A or a pharmaceutically acceptable salt thereof (e.g., in a formulation or a unit dose form as described herein), wherein greater than 81% of IRAK4 degradation in PBMCs is achieved (e.g., by measuring, at Day 7 or Day 14, IRAK4 levels in PBMCs using mass spectrometry or lymphocytes and monocytes using flow cytometry). In some embodiments, daily administration of from about 25 mg to about 200 mg of Compound A or a pharmaceutically acceptable salt thereof (e.g., in a formulation or a unit dose form as described herein) results in greater than 87% of IRAK4 degradation in PBMCs at Day 7 or Day 14. In some embodiments, daily administration of about 50 mg to about 200 mg of Compound A or a pharmaceutically acceptable salt thereof (e.g., in a formulation or a unit dose form as described herein) results in greater than 93% of IRAK4 degradation in PBMCs at Day 7 or Day 14. In some embodiments, an IRAK4 degradation in PBMCs, as listed in FIG. 11 or FIG. 12, is achieved.

In some embodiments, the present disclosure provides a method of administering Compound A to a patient in need thereof, comprising administering to said patient a therapeutically effective amount of Compound A or a pharmaceutically acceptable salt thereof (e.g., in a formulation or a unit dose form as described herein), wherein an inhibition of cytokines is achieved (e.g., by measuring percent change from baseline at about 24-48 hours post-administration in ex vivo proinflammatory cytokine induction by R848 and LPS in whole blood). In some embodiments, from about 50% to about 99%, about 65% to about 98%, or about 79% to about 97% inhibition of cytokines in whole blood at about 24-48 hours post-administration is achieved. In some embodiments, the cytokines include IFN-γ, IL-12, IL-1β, IL-10, IL-6, TNF-α, IL-8, IL-17, and IL-23. In some embodiments, an administration of up to about 1000 mg of Compound A or a pharmaceutically acceptable salt thereof (e.g., in a formulation or a unit dose form as described herein) results in the inhibition in whole blood at about 24-48 hours post-administration of up to about 97% IFN-γ, up to about 93% IL-12, up to about 92% IL-1β, up to about 89% IL-10, up to about 88% IL-6, up to about 88% TNF-α, up to about 81% IL-8, or up to about 79% IL-17. In some embodiments, a cytokine inhibition, as listed in Table 5 below, is achieved.

Figure 16:
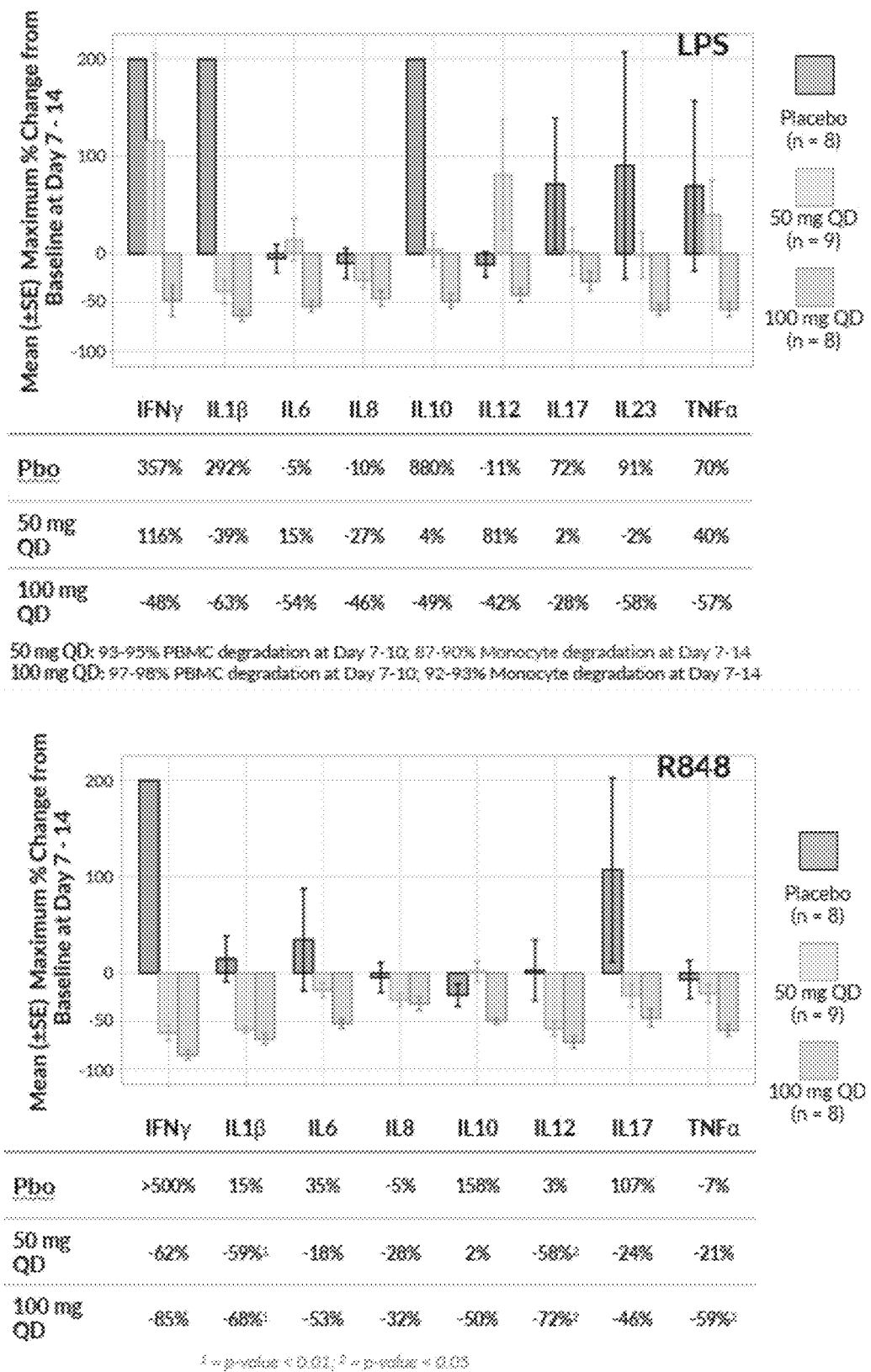
FIG. 16 shows ex vivo cytokine inhibition across nine disease relevant cytokines and chemokines.

In some embodiments, the present disclosure provides a method of administering Compound A to a patient in need thereof, comprising daily administering to said patient a therapeutically effective amount of Compound A or a pharmaceutically acceptable salt thereof (e.g., in a formulation or a unit dose form as described herein), wherein an inhibition of cytokines is achieved (e.g., by measuring percent change from baseline at Day 7-14 in ex vivo proinflammatory cytokine induction by R848 and LPS in whole blood). In some embodiments, from about 28% to about 85%, about 40% to about 85%, or about 50% to about 85% inhibition of cytokines in whole blood at Day 7-14 is achieved. In some embodiments, the cytokines include IFN-γ, IL-12, IL-1β, IL-10, IL-6, TNF-α, IL-8, IL-17, and IL-23. In some embodiments, daily administration of up to about 200 mg of Compound A or a pharmaceutically acceptable salt thereof (e.g., in a formulation or a unit dose form as described herein) results in the inhibition in whole blood at Day 7-14 of up to about 85% IFN-γ, up to about 72% IL-12, up to about 68% IL-1β, up to about 50% IL-10, up to about 54% IL-6, up to about 59% TNF-α, up to about 46% IL-8, or up to about 46% IL-17. In some embodiments, a cytokine inhibition, as listed in FIG. 16 is achieved.

4. Description of Exemplary Formulations and Dosage Forms

Compound A demonstrates low aqueous solubility of ≤3 mg/mL across the physiological pH range with medium permeability. Only slight increases of solubility were observed in bio-relevant fluid at pH 6.5 (FaSSIF <12 mg/mL) due to the presence of bile salt. Compound A can be classified tentatively as a BCS II compound. Challenges were encountered with oral administration of the standard formulation with crystalline Compound A HCl in preclinical species in early non-GLP studies. Thus, an enabling formulation approach was explored to improve the apparent solubility and potentially enhance the oral bioavailability of Compound A in the GLP toxicology program in rat and dog.

A range of enabling formulations were evaluated namely lipids, co-solvent with lipid combinations, amorphous solid dispersion (ASD) with different polymers and cyclodextrin solution to optimize the pharmacokinetic profile of Compound A. A 25% hydroxypropyl-beta-cyclodextrin (HPβCD) Compound A solution at 30 mg/mL was developed which offered 2-4-fold increased exposure in rat and dog versus all other formulations studied.

To improve the apparent solubility in aqueous vehicle, the ASD containing Compound A and HPβCD was prepared via the spray drying process, resulting in the spray dried dispersion (SDD). The 20% Compound A and 80% HPβCD SDD was used in the GLP toxicology program, in both rat and dog. The GLP test article was formulated as a solution by dissolving the SDD in 0.1 M acetate at pH 3.5 with the final concentration of 25% HPβCD (w/v).

The first-in-human (FIH) dosage form was built off the knowledge gained during the GLP toxicology formulation. The SDD using HPβCD was the initial base case with efforts to improve drug loading. Crystalline Compound A was also investigated to understand if a less complex dosage form could be developed as compared to the HPβCD based SDD tablet.

An initial FIH formulation screening PK study was performed in dog. The results indicated that the standard immediate release (IR) crystalline tablet resulted in significantly lower exposures compared to the HPMCAS-M based SDD tablet. The results also indicated that addition of HPβCD to the HPMCAS-M based SDD tablet provided further exposure enhancement as compare to the SDD tablet without HPβCD. Based on these results, an IR tablet dosage form containing Compound A: HPMCAS-M (25:75) SDD with HPβCD: Compound A (3:1) was selected for further development. In an effort to reduce the tablet weight, an additional formulation with reduced amounts of HPβCD was also developed, comprised of Compound A: HPMCAS-M (25:75) SDD with HPβCD: Compound A (1.6:1).

A second preclinical PK dog study was conducted to compare the GLP tox solution to two tablet formulations with 3.0:1 and 1.6:1 ratios of HPβCD: Compound A. The results of this study demonstrate that the GLP tox solution resulted in higher exposure than the tablet formulations potentially due to the differences in dosage form (solution vs solid tablet). The results also illustrated that the exposure of Compound A from the two tablet formulations are comparable and tablet hardness has no negative impact in terms of exposure for either formulations. However, the exposure variability of the 1.6:1 HPβCD: Compound A tablet is lower as compared to the 3.0:1 HPβCD: Compound A tablets. Furthermore, the core tablet weight of the 1.6:1 HPβCD: Compound A formulation is less than 3.0:1 HPβCD: Compound A (800 mg vs 1000 mg). Thus, the 1.6:1 HPβCD: Compound A HPMCAS-M based SDD IR tablet formulation was selected to support the FIH trial.

In some embodiments, the present invention provides a formulation and/or unit dosage form comprising Compound A, or a pharmaceutically acceptable salt thereof. In some embodiments, a Compound A formulation of the invention is a spray-dried formulation comprising Compound A, or a pharmaceutically acceptable salt thereof. In some embodiments, a Compound A unit dosage form of the invention is a tablet comprising Compound A, or a pharmaceutically acceptable salt thereof. In some embodiments, a tablet of the present invention is an immediate release (IR) tablet.

In some embodiments, a tablet of the present invention comprises Compound A free base. In some embodiments, a spray-dried formulation of the present invention comprises Compound A free base. In some embodiments, Compound A free base is amorphous. In some embodiments, Compound A free base is in crystal form.

In some embodiments, a tablet of the present invention comprises a pharmaceutically acceptable salt of Compound A. In some embodiments, a spray-dried formulation of the present invention comprises a pharmaceutically acceptable salt of Compound A. In some embodiments, a pharmaceutically acceptable salt of Compound A is amorphous. In some embodiments, a pharmaceutically acceptable salt of Compound A is in crystal form.

In some embodiments, a tablet of the present invention comprises Compound A hydrochloride (HCl) salt. In some embodiments, a spray-dried formulation of the present invention comprises Compound A HCl salt. In some embodiments, Compound A HCl salt is amorphous. In some embodiments, Compound A HCl salt is in crystal form.

In some embodiments, a tablet of the present invention comprises an amorphous solid dispersion of Compound A, or a pharmaceutically acceptable salt thereof, manufactured by spray drying. In some embodiments, a dispersion-containing tablet of the present invention provides enhanced oral bioavailability of Compound A.

In some embodiments, a tablet of the present invention comprises one or more pharmaceutically acceptable excipient or carrier, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide. In some embodiments, an IR tablet of the present invention comprises one or more pharmaceutically acceptable excipient or carrier including, but are not limited to, starches, sugars, micro-crystalline cellulose, diluents, granulating agents, lubricants, binders, and disintegrating agents. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

Suitable binders include, but are not limited to, starch (including potato starch, corn starch, and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone (PVP), cellulosic polymers (including hydroxypropyl cellulose (HPC), hydroxypropylmethylcellulose (HPMC), methyl cellulose, ethyl cellulose, hydroxyethyl cellulose (HEC), carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, carbomers, carrageenan, cellulose acetate phthalate, *ceratonia*, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein.

Suitable fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

In some embodiments, a tablet of the invention comprises a pharmaceutically acceptable polymer. In some embodiments, a spray-dried formulation of the invention comprises a pharmaceutically acceptable polymer. In some embodiment, a pharmaceutically acceptable polymer is polyvinylpyrrolidone/vinyl acetate copolymer (PVP-VA). In some embodiment, a pharmaceutically acceptable polymer is hypromellose (HPMC). In some embodiment, a pharmaceutically acceptable polymer is hypromellose phthalate (HPMCP-55). In some embodiment, a pharmaceutically acceptable polymer is hypromellose acetate succinate MG grade (HPMCAS-M). In some embodiment, a pharmaceutically acceptable polymer is hypromellose acetate succinate LG grade (HPMCAS-L). In some embodiment, a pharmaceutically acceptable polymer is vitamin E TPGS (TPGS). In some embodiment, a pharmaceutically acceptable polymer is microcrystalline Cellulose (MCC).

In some embodiments, a spray-dried formulation comprises about 5, about 10, about 15, about 20, about 25, about 30, about 35, about 40, about 45, about 50, about 55, about 60, about 65, about 70, about 75, about 80, about 85, about 90, or about 95% wt/wt Compound A, or a pharmaceutically acceptable salt thereof. In some embodiments, a spray-dried formulation comprises about 10-75% wt/wt Compound A, or a pharmaceutically acceptable salt thereof. In some embodiments, a spray-dried formulation comprises about 10-70, about 15-65, about 15-60, about 20-55, about 20-50, about 25-45, or about 25-40% wt Compound A, or a pharmaceutically acceptable salt thereof. In some embodiments, a spray-dried formulation comprises Compound A at about 25% wt/wt.

In some embodiments, a spray-dried formulation comprises a pharmaceutically acceptable polymer at about 5, about 10, about 15, about 20, about 25, about 30, about 35, about 40, about 45, about 50, about 55, about 60, about 65, about 70, about 75, about 80, about 85, about 90, or about 95% wt/wt. In some embodiments, a spray-dried formulation comprises a pharmaceutically acceptable polymer at about 5-95, about 10-95, about 15-90, about 20-90, about 25-90, about 30-85, about 35-85, about 40-85, about 45-80, about 50-80, about 55-80, or about 60-80% wt/wt. In some embodiments, a pharmaceutically acceptable polymer in a spray-dried formulation is selected from PVP-VA, HPMC, HPMCP-55, HPMCAS-M, TPGS, and HPMCAS-L. In some embodiments, a spray-dried formulation comprises a pharmaceutically acceptable polymer selected from PVP-VA, HPMC, HPMCP-55, HPMCAS-M, and HPMCAS-L at about 60-80% wt/wt. In some embodiments, a spray-dried formulation comprises HPMCAS-M at about 75% wt/wt.

In some embodiments, the present invention provides a spray-dried formulation comprising about 20-30:70-80 (% wt/wt) Compound A or a pharmaceutically acceptable salt thereof: HPMCAS-M. In some embodiments, the present invention provides a spray-dried formulation comprising about 25:75 (% wt/wt) Compound A or a pharmaceutically acceptable salt thereof: HPMCAS-M. In some embodiments, the present invention provides a spray-dried formulation comprising about 25:75 (% wt/wt) Compound A free base: HPMCAS-M.

In some embodiments, a spray-dried formulation of the present invention is selected from those described in Example 1 below. In some embodiments, the present invention provides a 25:75% wt/wt Compound A: HMPCAS-M amorphous solid dispersion (ASD). In some embodiments, the present invention provides a 25:75% wt/wt Compound A: HMPCAS-M spray dried dispersion (SDD).

In some embodiments, a tablet of the invention comprises a spray-dried formulation of the invention, and a pharmaceutically acceptable excipient or carrier. In some embodiments, a tablet of the invention comprises about 25-85% wt/wt of a spray-dried formulation of the invention. In some embodiments, a tablet of the invention comprises about 25, about 30, about 35, about 40, about 45, about 50, about 55, about 60, about 65, about 70, about 75, about 80, or about 85% wt/wt of a spray-dried formulation of the invention. In some embodiments, a tablet of the invention comprises about 20-80, about 25-75, about 30-70, about 35-70, about 40-65, or about 45-55% wt/wt of a spray-dried formulation of the invention.

In some embodiments, a tablet of the invention comprises Compound A at about 5-20% wt/wt. In some embodiments, a tablet of the invention comprises Compound A at about 5, about 7.5, about 10, about 12.5, about 15, about 17.5, or about 20% wt/wt. In some embodiments, a tablet of the invention comprises Compound A at about 12.5% wt/wt.

In some embodiments, a tablet of the invention comprises HMPCAS-M at about 30-50% wt/wt. In some embodiments, a tablet of the invention comprises HMPCAS-M at about 30, about 32.5, about 35, about 37.5, or about 40% wt/wt. In some embodiments, a tablet of the invention comprises HMPCAS-M at about 37.5% wt/wt.

In some embodiments, a tablet of the invention comprises a filler. In some embodiments, a filler is selected from mannitol, microcrystalline cellulose, or a mixture thereof. In some embodiments, a tablet comprises a filler (e.g., mannitol, microcrystalline cellulose) at about 10-25% wt/wt. In some embodiments, a tablet comprises a filler at about 10, about 15, about 20, or about 25% wt/wt. In some embodiments, a tablet comprises 7.5% mannitol and 7.5% microcrystalline cellulose.

Suitable forms of microcrystalline cellulose include, but are not limited to, the materials sold as AVICEL-PH-101, AVICEL-PH-103 AVICEL RC-581, AVICEL-PH-105 (FMC Corporation, Marcus Hook, Pa.), and mixtures thereof. Suitable anhydrous or low moisture excipients or additives include AVICEL-PH-103.TM. and Starch 1500 LM.

In some embodiments, a tablet of the invention comprises a disintegrant. Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof.

In some embodiments, a disintegrant is croscarmellose sodium (Ac-Di-Sol). In some embodiments, a tablet comprises a disintegrant at about 5-15% wt/wt. In some embodiments, a tablet comprises a disintegrant at about 10, about 11, about 12, about 13, about 14, or about 15% wt/wt. In some embodiments, a tablet comprises a disintegrant at about 11-13% wt/wt. In some embodiments, a tablet comprises a disintegrant at about 12% wt/wt. In some embodiments, the disintegrant comprises intragranular and extragranular filler (e.g., Ac-Di-Sol). In some embodiments, the disintegrant (e.g., Ac-Di-Sol) is about 9.67% intragranular and about 2.33% extragranular.

In some embodiments, a tablet of the present invention comprises one or more glidants. Suitable glidants include, but are not limited to, colloidal silicon dioxide (CAB—O—SIL) and asbestos-free talc. In some embodiments, a glidant is colloidal silicon dioxide. In some embodiments, a tablet comprises a glidant at about 0.5-5% wt/wt. In some embodiments, a tablet comprises a glidant at about 0.5, about 1, about 1.5, about 2, about 3, about 4, or about 5% wt/wt. In some embodiments, a tablet comprises a glidant at about 1-3% wt/wt. In some embodiments, a tablet comprises a glidant at about 1.5% wt/wt. In some embodiments, the glidant comprises intragranular and extragranular granular glidant (e.g., colloidal silicon dioxide). In some embodiments, the glidant (e.g., colloidal silicon dioxide) is about 1.00% intragranular and about 0.50% extragranular.

In some embodiments, a tablet of the present invention comprises one or more lubricants. Suitable lubricants include, but are not limited to, sodium stearyl fumarate, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB—O—SIL (a pyrogenic silicon dioxide product sold by Cabot Co. of Boston, Mass.), and mixtures thereof.

In some embodiment, the lubricant is sodium stearyl fumarate. In some embodiments, a tablet comprises glidant at about 0.5-5% wt/wt. In some embodiments, a tablet comprises glidant at about 0.5, about 1, about 1.5, about 2, about 3, about 4, or about 5% wt/wt. In some embodiments, a tablet comprises glidant at about 0.5-1.5% wt/wt. In some embodiments, a tablet comprises glidant at about 1% wt/wt. In some embodiments, the glidant comprises intragranular and extragranular glidant (e.g., sodium stearyl fumarate). In some embodiments, the lubricant (e.g., sodium stearyl fumarate) is about 1.00% intragranular and about 0.50% extragranular.

In some embodiments, a tablet of the invention comprises a solubility enhancer. In some embodiments, a solubility enhancer is hydroxypropyl-beta-cyclodextrin (HPβCD). In some embodiments, a tablet comprises a solubility enhancer at about 10-30% wt/wt. In some embodiments, a tablet comprises a solubility enhancer at about 10, about 11, about 12, about 13, about 14, about 15, about 16, about 17, about 18, about 19, or about 20% wt/wt. In some embodiments, a tablet comprises a solubility enhancer at about 15-25% wt/wt. In some embodiments, a tablet comprises a solubility enhancer (e.g., HPβCD) at about 20% wt/wt.

In some embodiments, the present invention provides an IR tablet which has a full release in about 10 minutes in a sink dissolution test. In some embodiments, an IR tablet of the present invention has a full release in about 9, about 8, about 7, about 6, or about 5 minutes in a sink dissolution test. In some embodiments, an IR tablet of the present invention has a full release in about 4 minutes in a sink dissolution test. In some embodiments, an IR tablet of the present invention has a full release in about 3 minutes in a sink dissolution test. In some embodiments, an IR tablet of the present invention has a full release in about 2 minutes in a sink dissolution test.

In some embodiments, an IR tablet of the present invention has a full release in about 1 minute in a sink dissolution test.

In certain embodiments, a tablet of the present invention is manufactured using standard, art-recognized tablet processing procedures and equipment. In certain embodiments, the method for forming the tablets is direct compression of a powdered, crystalline and/or granular composition comprising a solid form provided herein, alone or in combination with one or more excipients or carriers, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used. In some embodiments, a tablet of the present invention is manufactured using the process described in Example 2 below (FIG. 1).

In certain embodiments, a tablet of the present invention comprises one or more diluents. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-.beta.-cyclodextrin, talc, tragacanth, trehalose, and xylitol.

In some embodiments, a tablet of the present invention comprises one or more coloring agents. Suitable coloring agents include, but are not limited to, any of the approved, certified, water soluble FD&C dyes, and water insoluble FD&C dyes suspended on alumina hydrate, and color lakes and mixtures thereof, e.g., Opadry® coloring agents. A color lake is the combination by adsorption of a water-soluble dye to a hydrous oxide of a heavy metal, resulting in an insoluble form of the dye.

In some embodiments, a tablet of the present invention comprises one or more flavoring agents. Suitable flavoring agents include, but are not limited to, natural flavors extracted from plants, such as fruits, and synthetic blends of compounds which produce a pleasant taste sensation, such as peppermint and methyl salicylate.

In certain embodiments, a tablet of the present invention comprises one or more sweetening agents. Suitable sweetening agents include, but are not limited to, sucrose, lactose, mannitol, syrups, glycerin, and artificial sweeteners, such as saccharin and aspartame.

In certain embodiments, a tablet of the present invention comprises one or more emulsifying agents. Suitable emulsifying agents include, but are not limited to, gelatin, acacia, tragacanth, bentonite, and surfactants, such as polyoxyethylene sorbitan monooleate (TWEEN®20), polyoxyethylene sorbitan monooleate 80 (TWEEN® 80), and triethanolamine oleate.

In certain embodiments, a tablet of the present invention comprises one or more suspending and dispersing agents. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

In certain embodiments, a tablet of the present invention comprises one or more preservatives. Suitable preservatives include, but are not limited to, glycerin, methyl and propylparaben, benzoic add, sodium benzoate and alcohol.

In certain embodiments, a tablet of the present invention comprises one or more wetting agents. Suitable wetting agents include, but are not limited to, propylene glycol monostearate, sorbitan monooleate, diethylene glycol monolaurate, and polyoxyethylene lauryl ether.

In certain embodiments, a tablet of the present invention comprises one or more solvents. Suitable solvents include, but are not limited to, glycerin, sorbitol, ethyl alcohol, and syrup.

In certain embodiments, a tablet of the present invention comprises one or more non-aqueous liquids. Suitable non-aqueous liquids utilized in emulsions include, but are not limited to, mineral oil and cottonseed oil.

In certain embodiments, a tablet of the present invention comprises one or more organic acids. Suitable organic acids include, but are not limited to, citric and tartaric acid.

In certain embodiments, a tablet of the present invention comprises one or more sources of carbon dioxide. Suitable sources of carbon dioxide include, but are not limited to, sodium bicarbonate and sodium carbonate.

In certain embodiments, a tablet of the present invention can be a multiple compressed tablet, an enteric-coating tablet, or a sugar-coated or film-coated tablet. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets. In some embodiments, a tablet of the present invention comprises an Opadry® II Brown film coating. In some embodiments, an Opadry® II Brown film coating on a tablet of the present invention comprises the components at the weight percentages as described in Table 3. In some embodiments, a tablet of the present invention comprises a Opadry® II Yellow film coating. In some embodiments, an Opadry® II Yellow film coating on a tablet of the present invention comprises the components at the weight percentages as described in Table 3.

A tablet of the present invention can be prepared from the active ingredient in powdered, crystalline, or granular forms, alone or in combination with one or more carriers or excipients described herein, including binders, disintegrants, controlled-release polymers, lubricants, diluents, and/or colorants.

Components of a tablet of the present invention can be intragranular or extragranular. In some embodiments, a tablet comprises intragranularly Compound A, HPMCAS-M, mannitol, microcrystalline cellulose, hydroxypropyl-beta-cyclodextrin (HPβCD), colloidal silicon dioxide, croscarmellose sodium, and stearyl fumarate sodium. In some embodiments, a tablet comprises extragranularly colloidal silicon dioxide, croscarmellose sodium, and stearyl fumarate sodium. In some embodiments, the present invention provides a tablet of Table 2.

In some embodiments, a tablet of the present invention comprises about 10-250 mg of Compound A. In some embodiments, a tablet of the present invention comprises about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250 mg of Compound A. In some embodiments, a tablet of the present invention comprises about 25-100 mg of compound A. In some embodiments, a tablet of the present invention comprises about 25 or 100 mg of Compound A.

In some embodiments, the present invention provides a tablet of about 208 mg, comprising:
  i) a tablet core of about 200 mg, comprising intragranularly: about 25 mg Compound A free base, about 75 mg HPMCAS-M, about 15 mg mannitol, about 15 mg microcrystalline cellulose, about 40 mg hydroxypropyl-beta-cyclodextrin, about 19.34 mg croscarmellose sodium, about 2 mg stearyl fumarate sodium, and about 2 mg colloidal silicon dioxide; and extragranularly: about 4.66 mg croscarmellose sodium, about 1 mg stearyl fumarate sodium, and about 1 mg colloidal silicon dioxide; and
  ii) Opadry® II Yellow Film Coating of about 8 mg, comprising about 3.2 mg Polyvinyl Alcohol, 1.616 mg Macrogol/PEG, 1.872 mg Titanium Dioxide, 0.128 mg Iron Oxide, and 1.184 mg Talc.

In some embodiments, the present invention provides a tablet of about 824 mg, comprising:
  i) a tablet core of about 800 mg, comprising intragranularly: about 100 mg Compound A free base, about 300 mg HPMCAS-M, about 45 mg mannitol, about 45 mg microcrystalline cellulose, about 160 mg hydroxypropyl-beta-cyclodextrin, about 77.36 mg croscarmellose sodium, about 8 mg stearyl fumarate sodium, and about 8 mg colloidal silicon dioxide; and extragranularly: about 18.64 mg croscarmellose sodium, about 4 mg stearyl fumarate sodium, and about 4 mg colloidal silicon dioxide; and
  ii) Opadry® II Yellow Film Coating of about 24 mg, comprising about 9.6 mg Polyvinyl Alcohol, 4.848 mg Macrogol/PEG, 5.616 mg Titanium Dioxide, 0.384 mg Iron Oxide, and 3.552 mg Talc.

5. Methods and Uses for Treating Disease

In some embodiments, the present invention provides a method for treating an autoimmune/autoinflammatory disease or a hematological malignancy in a patient, comprising administering to the patient a therapeutically effective amount of Compound A, or a pharmaceutically acceptable salt thereof. In some embodiments, the autoimmune/autoinflammatory disease is a cutaneous autoimmune/autoinflammatory disease.

In some embodiments, the autoimmune/autoinflammatory disease includes inflammatory or allergic conditions of the skin, for example psoriasis, generalized pustular psoriasis (GPP), psoriasis vulgaris, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, hidradenitis suppurativa, Sweet Syndrome, pyoderma gangrenosum, and other inflammatory or allergic conditions of the skin. In some embodiments, the inflammatory disease of the skin is selected from contact dermatitits, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, or hidradenitis suppurativa.

In some embodiments, Compound A may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, juvenile rheumatoid arthritis, systemic juvenile idiopathic arthritis (SJIA), cryopyrin associated periodic syndrome (CAPS), adult onset Still's disease, macrophage activation syndrome (MAS), primary and secondary hemophagocytic lymphohistiocytosis (HLH), familial Mediterranean fever, NLRP12 autoinflammatory syndrome, and osteoarthritis.

In some embodiments the inflammatory disease which can be treated is a TH17 mediated disease. In some embodiments the TH17 mediated disease is selected from systemic lupus erythematosus, multiple sclerosis, psoriasis vulgaris, hidradenitis suppurativa, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis or chronic rhinosinusitis with nasal polyps (CRSwNP).

In some embodiments, the present disclosure provides a method for treating a cutaneous autoimmune/autoinflammatory disease in a patient, such as atopic dermatitis (AD) and hidradenitis suppurativa (HS), comprising administering to the patient a therapeutically effective amount of Compound A, or a pharmaceutically acceptable salt thereof.

In some embodiments, the present disclosure provides a method for treating AD in a patient, comprising administering to the patient a therapeutically effective amount of Compound A, or a pharmaceutically acceptable salt thereof.

In some embodiments, the present disclosure provides a method for treating HS in a patient, comprising administering to the patient a therapeutically effective amount of Compound A, or a pharmaceutically acceptable salt thereof.

In some embodiments, the present disclosure provides a method for treating rheumatoid arthritis (RA) in a patient, comprising administering to the patient a therapeutically effective amount of Compound A, or a pharmaceutically acceptable salt thereof.

In some embodiments, the present disclosure provides a method for treating hematological malignancy in a patient, comprising administering to the patient a therapeutically effective amount of Compound A, or a pharmaceutically acceptable salt thereof. In some embodiments, the hematological malignancy is leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma, AML, or MDS.

The following examples are provided for illustrative purposes only and are not to be construed as limiting this invention in any manner.

EXEMPLIFICATION

Compound A can be prepared by methods known to one of ordinary skill in the art, for example, as described in WO 2019/133531 and WO 2020/010227, the contents of which are incorporated herein by reference in their entireties.

List of Abbreviations

AD Atopic dermatitis
AE Adverse event
ALT Alanine aminotransferase
BCRP Breast cancer resistance protein
BMI Body mass index
BP Blood pressure
CRBN Cereblon
DDI Drug-drug interaction
ECG Electrocardiogram
eCRF Electronic case report form
FIH First in human
FE Food effect
FFPE Formalin-fixed paraffin-embedded
FSH Follicle-stimulating hormone
GEP Gene expression profiling
GI Gastrointestinal
GLP Good Laboratory Practices
HDPE High density polyethylene
HED Human equivalent dose
HIV Human immunodeficiency virus
HR Heart Rate
HRT Hormonal replacement therapy
HS Hidradenitis suppurativa
HV Healthy volunteer
IC50 Half-maximal inhibition concentrations
ICF Informed consent form
ICH GCP International Council for Harmonization Guidelines for Good Clinical Practices
IEC Independent Ethics Committees
IF Immunofluorescence
IL Interleukin
IRAK4 Interleukin-1 receptor-associated kinase 4
IRB Institutional Review Boards
MAD Multiple ascending dose
MIST Metabolites in safety testing
MS Mass Spectrometry
MyD88 Myeloid differentiation factor 88
NOAEL No-observed-adverse-effect level
PBMC Peripheral blood mononuclear cells
PD Pharmacodynamics
P-gp P-glycoprotein
PK Pharmacokinetics
RA Rheumatoid arthritis
SAD Single ascending dose
SARS-CoV-2 Severe acute respiratory syndrome coronavirus 2
SDD Spray-dried dispersion
SAE Serious adverse event SAP Statistical analysis plan
SD Standard deviation
SoA Schedule of assessments
SOP Standard Operating Procedures
SRC Safety Review Committee
TEAE Treatment-emergent adverse events
TLR Toll-like receptors
TNF Tumor necrosis factor
ULN Upper limit of normal
UV Ultraviolet
WOCBP Woman of Childbearing Potential Definitions Ae(t1-t2) By-interval amount excreted in urine during each collection interval.
Ae(0-t) Cumulative amount excreted in urine during the pooled collection intervals
AUC(0-∞) Area under the plasma concentration-time curve from time zero to infinity.
AUC(0-last) Area under the plasma concentration-time curve from time zero to last measurable concentration.
AUC(0-tau) Area under the plasma concentration-time curve during a dosing interval.
Cavg Average concentration over the dosing interval.
CL/F Apparent clearance.
Cmax Maximum observed concentration.
Ctrough Concentration at the end of dose interval.
F Relative bioavailability fed/fasted.
fe(t1-t2) By-interval fraction of dose excreted in urine during each collection interval.
fe(0-t) Cumulative fraction of dose excreted in urine during the pooled collection intervals
MRT Mean residence time.
t1/2 Terminal half-life.
tmax Time to Cmax.
RAUC Accumulation ratio for AUC.
RCmax Accumulation ratio for Cmax.
Vz/F Apparent volume of distribution.

Example 1. Drug Product

Description: Compound A tablets, also referred to as "drug product", are supplied as 25 mg dose strength standard round convex tablets and 100 mg dose strength modified oval-shaped tablets. Both dose strengths use a common granulation and are compressed into tablets of different sizes and film coated. The film coating is added for taste masking and ease of swallowing.

The active Compound A is contained within the tablet formulation as an amorphous solid dispersion (ASD). The ASD is manufactured by spray drying and will be referred to as a spray-dried dispersion (SDD). The SDD, also referred to as "drug product intermediate" is 25% active Compound A by weight with HPMCAS-M (25% Compound A:75% HPMCAS-M).

The composition of the drug product intermediate, including the amount and function of the component and the quality standard are provided in Table 1. The composition of the Compound A drug product, including the amount per unit, function of the component and the quality standard are provided in Table 2. The composition of the film coatings used for the pilot and cGMP manufactured tablets is provided in Table 3. The composition of the pilot tablet film coating contains all combinations of globally acceptable colorants. The cGMP manufactured tablets utilize a subset of these pigments at equivalent, lower or zero levels except titanium dioxide.

TABLE 1

Composition of Drug Product Intermediate (SDD): 25% Compound A: 75% HPMCAS-M

| Component | Function | Composition (%) |
|---|---|---|
| Compound A[a] | Active Ingredient | 25.0 |
| Hypromellose acetyl succinate (HPMCAS-M), NF | Stabilizer | 75.0 |
| Methanol[b], USP/NF | Spray drying solvent | NA |
| Dichloromethane[b], USP/NF | Spray drying solvent | NA |
| Water for Injection[b], USP | Spray drying solvent | NA |

[a]The drug substance is supplied as the Compound A HCl. The Active Pharmaceutical Ingredient (API), Compound A freebase, is combined in a 25%:75% ratio with HPMCAS-M to provide a spray-dried dispersion, also referred to as "drug product intermediate".
[b]These ingredient are a manufacturing aids and not found in the drug product in significant quantities.

TABLE 2

Drug Product Unit Composition for Compound A 25 mg and 100 mg Tablets

| | | Weight | Amount per Unit | |
|---|---|---|---|---|
| Component: Quality Standard | Function | % per Unit | 25 mg Strength | 100 mg Strength |
| Tablet Core | | | | |
| SDD, drug product intermediate (25% Compound A:75% HPMCAS-M) | Active Ingredient | 50.00 | 100.00 mg | 400.00 mg |
| Mannitol[a] NF, EP | Filler | 7.50 | 15.00 mg | 60.00 mg |
| Microcrystalline cellulose; USP/NF, EP | Filler | 7.50 | 15.00 mg | 60.00 mg |
| Hydroxypropyl-beta-cyclodextrin (HPβCD) | Solubility Enhancer | 20.00 | 40.00 mg | 160.00 mg |

TABLE 2-continued

Drug Product Unit Composition for Compound A 25 mg and 100 mg Tablets

| Component: Quality Standard | Function | Weight % per Unit | Amount per Unit 25 mg Strength | Amount per Unit 100 mg Strength |
|---|---|---|---|---|
| Croscarmellose sodium; USP/NF, EP | Disintegrant | 9.67 | 19.34 mg | 77.36 mg |
| Stearyl fumarate sodium; USP/NF/EP | Lubricant | 1.00 | 2.00 mg | 8.00 mg |
| Colloidal silicon dioxide; USP/NF, EP | Glidant | 1.00 | 2.00 mg | 8.00 mg |
| Croscarmellose sodium; USP/NF, EP (extra granular) | Disintegrant | 2.33 | 4.66 mg | 18.64 mg |
| Stearyl fumarate sodium; USP/NF, EP (extra granular) | Lubricant | 0.50 | 1.00 mg | 4.00 mg |
| Colloidal silicon dioxide ; USP/NF, EP (extra granular) | Glidant | 0.50 | 1.00 mg | 4.00 mg |
| Total | | 100.00 | 200.00 mg | 800.00 mg |
| | Film Coating | | | |
| Opadry ® II Yellow | Film Coating | 4.0% | 8.00 mg[c] | — |
| | | 3.0% | — | 24.00 mg[c] |
| Purified Water[b]; USP | Processing Aid | | | |
| Total Tablet % Composition and Weight | | | 208.00 mg | 824.00 mg |

USP = United States Pharmacopeia,
NF = National Formulary,
EP = European Pharmacopoeia
[a]The amount of mannitol used is adjusted to compensate for the measured potency of the spray dried dispersion.
[b]Water is removed during manufacturing. It is a processing aid and not present in significant amounts in the finished drug product.
[c]Target weight gain of tablet cores during film coating.

TABLE 3

Opadry ® II Film Coating Compositions Used in the Manufacturing of the Compound A 25 mg and 100 mg Pilot and cGMP Tablets

| Component; Quality Standard | Function | Opadry ® II Brown Weight Percent per Unit | Opadry ® II Brown Amount per Unit 25 mg Strength | Opadry ® II Brown Amount per Unit 100 mg Strength | Opadry ® II Yellow Weight Percent per Unit | Opadry ® II Yellow Amount per Unit 25 mg Strength | Opadry ® II Yellow Amount per Unit 100 mg Strength |
|---|---|---|---|---|---|---|---|
| Polyvinyl Alcohol; USP, EP, JP | Film Former | 40.0% | 3.200 mg | 9.600 mg | 40.00% | 3.200 mg | 9.600 mg |
| Macrogol/PEG, USP, EP, JP | Film Former | 20.2% | 1.616 mg | 4.848 mg | 20.20% | 1.616 mg | 4.848 mg |
| Titanium Dioxide; USP, EP, JP | Opacifier | 12.9% | 1.032 mg | 3.096 mg | 23.40% | 1.872 mg | 5.616 mg |
| Iron Oxide, Yellow, NF, JPE | Pigment | 4.0% | 0.320 mg | 0.960 mg | 1.60% | 0.128 mg | 0.384 mg |
| Iron Oxide, Red; NF, JPE | Pigment | 4.0% | 0.320 mg | 0.960 mg | — | — | — |
| Talc; USP, EP, JP | Detackifier | 14.8% | 1.184 mg | 3.552 mg | 14.80% | 1.184 mg | 3.552 mg |
| Black Iron Oxide; NF, JPE | Pigment | 2.0% | 0.168 mg | 0.504 mg | — | — | — |
| FD&C Blue #2; JECFA, JP | Pigment | 2.0% | 0.160 mg | 0.480 mg | — | — | — |
| Total Tablet % Composition and Weight | | 100.0% | 8.000 mg | 24.000 mg | 100.00% | 8.000 mg | 24.000 mg |

USP = United States Pharmacopeia;
NF = National Formulary;
EP = European Pharmacopoeia;
JECFA = Joint Evaluation Committee on Food Additives;
JP = Japanese Pharmacopoeia;
JPE = Japanese Pharmaceutical Excipients Example 2. Drug Product Manufacturing Process Description: The drug product is manufactured using processes and equipment commonly employed to produce SDDs and immediate-release tablets that are commonly available in the pharmaceutical industry. A description of the manufacturing process and steps is provided in Table 4. A manufacturing process flow diagram describing the operations involved in the manufacture of 25% Compound A:75% HPMCAS-M SDD and the Compound A 25 mg and 100 mg film coated tablets is shown below in FIG. 1.

The process may reasonably be adjusted while maintaining the same basic production steps to compensate for different batch sizes or equipment characteristics, or on the basis of experience gained from previous production batches.

TABLE 4

Drug Product Manufacturing Process

| Step | Process Description |
|---|---|
| 1 | Dissolve the Compound A and HPMCAS-M into a solvent mixture containing di chloromethane, methanol, and water mixture at approximately 74:24:2 ratios with agitation at room temperature until both ingredients dissolved. |
| 2 | Set and monitor the drying gas rate inlet (between 70-110° C) & outlet temperatures (about 40° C.), solution flow rate (between 220 - 270 g/min), and solution feed pressure (between 400-800 psig) during the process. Spray dry the solution from step 1 and collect the 25% Compound A:75% HPMCAS-M SDD. |
| 3 | Transfer the SDD to a dryer and perform secondary drying at a pre-set temperature (about 50° C.) until the residual solvent content in the SDD meets the in-process specification. Determine the assay and purity of the SDD prior to next step as in-process control. |
| 4 | Add the microcrystalline cellulose, mannitol, secondary dried SDD from step 3, sodium stearyl fumarate, croscarmellose sodium, hydroxypropyl-beta-cyclodextrin and colloidal silicon dioxide to a blender and mix to form an intra-granular powder blend. |
| 5 | Dry granulate the blend from step 4 with a roller compactor and mill the ribbons into granules. Measure the particle size distribution, bulk, and tap densities of milled granules. |
| 6 | Transfer the milled granules from step 5 into the blender. Add sodium stearyl fumarate, croscarmellose sodium, and colloidal silicon dioxide into the blender and mix to form an extragranular blend for compression. |
| 7 | Compress the final powder blend from step 6 into tablets containing either 25 mg 100 mg of Compound A. Determine and monitor the tablet weight, hardness, thickness, and friability as in-process control at a specific time interval. Adjust the compression parameters if needed to maintain the target tablet weight, hardness and thickness during the compression run. |
| 8 | Add the coating material in water with agitation to form the well dispersed coating suspension. Transfer the core tablets from step 7 in the coating pan. Set the inlet temperature (between 50-60° C.), air flow (about 95 cfm), pan speed (between 7 and 13 rpm), atomization pressure, spray gun distance to tablet bed surface, and solution spray rate (between 6-15 g/min). Film coat the tablets. Monitor the outlet temperature and amount of suspension applied during the coating process. Complete the film coating when the coated tablet weight gain reaches to the target range. |
| 9 | Package the tablets into the container closure system which can be either in an induction sealed HDPE bottles with desiccant, polyester coils and child resistant cap or in bulk for pharmacist to dispense based on the instruction listed in pharmacy manual. |

Example 3. A Phase 1 Randomized, Placebo-Controlled, Single and Multiple Ascending Dose Trial to Evaluate the Safety, Tolerability, Pharmacokinetics, and Pharmacodynamics of Orally Administered Compound a in Healthy Adult Volunteers and Patients with Atopic Dermatitis (AD) or Hidradenitis Suppurativa (HS)

Objectives: To assess the safety, tolerability, pharmacokinetics (PK), and pharmacodynamics (PD) of Compound A after administering single and multiple oral doses at escalating dose levels in healthy volunteers (HVs) and following multiple doses in patients with AD or HS.

Overview of Study Design: This is a first in human (FIH), Phase 1 study of Compound A that will characterize the safety, PK, and PD of Compound A after a single dose and after repeated dosing in adult HVs and in patients with HS or AD. Initially, a dose range of Compound A in single ascending dose (SAD) escalation cohorts will be explored in adult HVs (Part A). To understand food effects (FE) on the PK and PD of Compound A in HVs, up to 2 SAD cohorts will be designated in Part A where HVs will return for a second treatment period and will receive the same treatment which was originally allocated, but in the fed state. Safety and PK data from at least 3 completed SAD cohorts will determine initiation of and appropriate doses for the 14-day multiple ascending dose (MAD) portion of the study (Part B). A single cohort of up to 20 patients with AD or HS (at least 10 patients with AD) will be subsequently enrolled (Part C) and Compound A will be administered to these patients for 14 days, at a dose and schedule selected by the Safety Review Committee (SRC) following review of the safety, PK, and PD data after completion of the dose escalation in Part B.

Part A: Part A is a double-blind, randomized, placebo-controlled, SAD, sequential group study in 56 adult HVs, divided in 7 cohorts of eight HVs each. Seven ascending single doses (1 dose level per cohort) will be investigated. One or more additional cohorts may be added, as needed. Within each cohort, 6 HVs will be randomized to receive Compound A and 2 HVs will be randomized to receive placebo.

In the SAD part, the planned Compound A doses are 25, 75, 150, 300, 600, 1000, and 1400 mg. Pharmacokinetic parameters at the no-observed-adverse-effect level (NOAELs) from the 28-day Compound A toxicokinetic studies in rats and dogs were used to calculate exposure ratios relative to predicted human AUC and Cmax for Compound A. These data indicate 79- to 159-fold exposure safety margin for the starting dose of 25 mg based on the AUCs of rat and dog NOAELs, respectively. The safety margin decreases as the dose increases. Following review of safety and PK data from HVs in the 25 mg dose cohort, dose levels of subsequent SAD cohorts may be adjusted from those proposed but will not exceed the designated fold increase of exposure indicated for each dose level.

At each dose level, 2 sentinel HVs (1 receiving Compound A and 1 receiving placebo) will be administered the investigational product first. The safety data up to 24-hours post-dose for these sentinel HVs will be reviewed by the Investigator to ensure acceptable tolerability before commencing administration of the investigational product to the remaining HVs in the cohort. Sequential dosing of HVs within a cohort will be staggered so that there will be at least a gap of 10 minutes between dosing of individual HVs. After the completion of each dose level, the blinded interim PK data through Day 5 and safety data through Day 14 will be reviewed by the SRC before proceeding to the next dose level. Each subsequent dose administration will be performed, if in the judgment of the Investigator and Safety Physician, the results of the safety analyses of the preceding dose administration are satisfactory.

In addition, the effect of food intake on the PK of Compound A will also be explored by selecting up to 2 SAD cohorts who will return for a second treatment period and will receive the same treatment allocation, in the fed state (within 30 minutes of completion of the FDA standard high-fat breakfast). The washout period between the first treatment and second treatment will be 14 days or 5 times of Compound A half-life, whichever is longer. Selection of cohorts will be based on the emerging safety and PK data from previous cohorts in Part A. The anticipated exposures in the FE study will not exceed the highest anticipated exposures in the next planned SAD study cohort where safety and tolerability of Compound A was established (e.g., SAD 5 exposures in a fed state will not exceed SAD 6 projected exposures in the fasted state).

The HVs will be screened for eligibility to participate in the study up to 26 days (Day −28) prior to admission to the study center on Day −2. Eligible HVs will be admitted to the study center on Day −2 and will be discharged on Day 5 after all scheduled assessments have been completed. Following discharge, HVs will return to the study center for follow-up visits on Days 7, 10, and 14.

Part B: Part B is a double-blind, randomized, placebo-controlled, MAD, sequential group study in 48 adult HVs, divided in 4 cohorts of 12 adult HVs in each cohort. One or more additional cohorts may be added, as needed.

The MAD portion of the study will evaluate 4 dose levels of Compound A continuous daily dosing for 14 days. The selection of Compound A doses will be guided by the safety, tolerability, and PK data in humans from the SAD portion of the study. The initial dose level of the first MAD cohort will be identified based on the PK observed in at least the first 3 SAD cohorts and will be a dose where the predicted ssAUCτ and ssCmax are below the exposure levels observed in the highest dose SAD cohort completed where Compound A was confirmed to be safe and tolerable. Increasing dose levels in subsequent MAD cohorts will be identified based on the safety and PK observed in the previous SAD and MAD cohorts. Dose escalation between each MAD cohort will not exceed 100%. The proposed maximum daily exposure at the highest dose MAD cohort will not exceed the highest exposure in the SAD study where safety and tolerability of Compound A was established.

Within each cohort, 9 HVs will be randomized to receive Compound A and 3 HVs will be randomized to receive placebo.

It is planned that Compound A or placebo will be administered orally once a day following an overnight fast for 10 hours, from Day 1 to Day 14, inclusive. However, the dosing interval and the duration of dosing may change following review of the safety, PK, and PD data from Part A.

As a precaution, Part A of the study will utilize a sentinel dosing strategy. This strategy will not be utilized in Part B, unless the safety and PK data from Part A indicates otherwise (eg, safety issue). After the completion of each MAD dose level, PK/PD data through Day 15 and safety data through Day 28 will be reviewed by the SRC before proceeding to the next dose level. Following review of the emerging safety, PK, and PD data from the first 2 MAD cohorts, this period for review may change either way, subject to a protocol amendment.

The HVs will be screened for eligibility to participate in the study up to 26 days (Day −28) prior to admission to the study center on Day −2. Eligible HVs will be admitted to the study center on Day −2 and will be discharged on Day 21 after all scheduled assessments have been completed. Following discharge on Day 21, HVs will return to the study center for a follow-up visit on Day 28. Additional visits may be planned following review of the emerging safety, PK, and PD data.

Part C: Part C is an open-label, multiple dose study in a single cohort of up to 20 patients with AD or HS (at least 10 patients with AD) and will commence after the completion of Part B. Part C will be conducted on both an inpatient and outpatient basis and patients will continue to be followed for safety through Day 28. The dose regimen and the requirement for patient confinement to the clinical units will be selected by the SRC from review of the safety, PK, and PD data after completion of Part B.

It is currently planned that the patients will be screened for eligibility from Day −42 and those eligible to participate will be admitted to the clinical unit on Day −2. Patients will be confined to the clinical unit as in Part B from Day −2 to Day 2 and from Day 13 to Day 15 and all other visits will occur as outpatient; however, this is subject to a satisfactory review of the emerging safety, PK, and PD data from Parts A and B, and following an agreement with the Investigator and the Sponsor. Patients may be asked to be confined as listed in Part B.

Stopping rules based primarily on safety with considerations of emerging PK and PD findings are defined for individual study participants, individual dose cohorts, and the entire study.

Number of Investigators and Study Centers: Approximately 2 Investigators and study centers are expected to participate in this study. The second study center will participate to support enrollment, as needed.

Study Population and Number of Study Participants: The total number of study participants is dependent on the number of cohorts required to determine the minimum and maximum effective doses.

Part A: Approximately 110 HVs will be screened to achieve 56 HVs assigned to the investigational product.

Part B: Approximately 100 HVs will be screened to achieve 48 HVs assigned to the investigational product.

Part C: Approximately 40 patients with AD or HS will be screened to achieve up to 20 patients assigned to the investigational product.

Inclusion Criteria

For Healthy Volunteers (Parts A and B)
1. Male HVs or female HVs aged 18 to 55 years (inclusive), at the time of consent with weight at least 50 kg and a body mass index (BMI) between 18.0 and 30.0 kg/m2 (inclusive), at Screening.
2. Healthy volunteers must be confirmed as negative in severe acute respiratory syndrome coronavirus 2 (SARS-CoV-2) infection test at Screening and on Day −2.
3. Evidence of a personally signed and dated informed consent document indicating that the HV has been informed of all pertinent aspects of the study.
4. Male HVs and their partners of childbearing potential must agree to use a highly effective method of contraception or 2 acceptable methods of contraception until 90 days after the investigational product administration. A man or woman is of childbearing potential if he or she is biologically capable of having children in the opinion of the Investigator and is sexually active. The HVs and their partners who have been surgically sterilized for less than 6 months prior to the date of informed consent must agree to use any medically acceptable methods of contraception.
5. Female HVs of nonchildbearing potential must meet at least 1 of the following criteria: a) Achieved postmenopausal status, defined as follows: cessation of regular menses for at least 12 consecutive months with no alternative pathological or physiological cause; and have a serum follicle-stimulating hormone (FSH) level confirming the postmenopausal state; b) Have undergone a documented hysterectomy and/or bilateral oophorectomy; and c) Have medically confirmed ovarian failure.
6. Female HVs of childbearing potential must agree to a combination of TWO of the following until 90 days after the investigational product administration: a) Barrier method of contraception: condoms (male or female) with or without a spermicidal agent, diaphragm or cervical cap with spermicide; b) IUD; and c) Hormone-based contraceptive.
7. Female subjects may not be pregnant, lactating, or breast-feeding or plan to become pregnant (including ova donation) within 90 days of last study drug administration.
8. Female subjects must have a negative result for the serum pregnancy test at the Screening Visit and at follow-up visit.
9. HVs must be willing and able to comply with scheduled visits, treatment plan, laboratory tests, and other study procedures.

For Patients (Part C)

Patients must meet all of the following inclusion criteria to be eligible for enrollment in the study:
1. Male or female patients aged 18 years to 55 years (inclusive) at the time of Screening, and in generally good health, except for AD or HS. Good health is defined as no clinically relevant abnormalities identified by a detailed medical history, physical examination, including BP and PR measurement, 12-lead ECG, and clinical laboratory tests.
2. Patients must be confirmed as negative in SARS-CoV-2 infection test at Screening and on Day −2.
2. Male patients and their partners of childbearing potential must agree to use a highly effective method of contraception or 2 acceptable methods of contraception until 90 days after the investigational product administration. A man or woman is of childbearing potential if he or she is biologically capable of having children in the opinion of the Investigator and is sexually active. The patients and their partners who have been surgically sterilized for less than 6 months prior to the date of informed consent must agree to use any medically acceptable methods of contraception.
3. Female patients of nonchildbearing potential must meet at least 1 of the following criteria: a) Achieved postmenopausal status, defined as follows: cessation of regular menses for at least 12 consecutive months with no alternative pathological or physiological cause; and have a serum FSH level confirming the postmenopausal state; b) Have undergone a documented hysterectomy and/or bilateral oophorectomy; and c) Have medically confirmed ovarian failure.
4. Female patients of childbearing potential must agree to a combination of TWO of the following until 90 days after the investigational product administration: a) Barrier method of contraception: condoms (male or female) with or without a spermicidal agent, diaphragm or cervical cap with spermicide; b) IUD; and c) Hormone-based contraceptive.
5. Female patients may not be pregnant, lactating, or breast-feeding or plan to become pregnant (including ova donation) within 90 days of last study drug administration.
6. Female patients must have a negative result for the serum pregnancy test at the Screening Visit and at the follow-up visit.
7. Diagnosis of AD or HS for at least 6 months prior to Day 1.
8. Patients with AD: having at least 25% treatable percentage body surface area at Screening or on Admission (excluding the scalp and designated venous access areas).
9. Has an Investigator's static global assessment score of moderate (3) or severe (4) at Screening or on Day −1.
10. Has a BMI of 17.5 to 35.0 kg/m2; and a total body weight >50 kg (110 lb).
11. Evidence of a personally signed and dated informed consent document indicating that the patient has been informed of all pertinent aspects of the study.
12. Patients who are willing and able to comply with scheduled visits, treatment plan, laboratory tests, and other study procedures.
13. Has adequate venous access with venous access sites having AD-unaffected, non-infected skin to permit repeated PK sampling.

Exclusion Criteria

For Healthy Volunteers (Parts A and B)

Healthy volunteers meeting any of the following criteria will be excluded from the study:
1. Healthy volunteers who do not conform to the above inclusion criteria.
2. Healthy volunteers with a predisposition to keloid scarring (excluded in Part B only).
3. Female HVs who are pregnant, trying to become pregnant or lactating.
4. Healthy volunteers who have a clinically relevant history or presence of respiratory, GI, renal, hepatic, hematological, lymphatic, neurological, cardiovascular, psychiatric, musculoskeletal, genitourinary, immunological, dermatological, or connective tissue diseases or disorders.
5. Healthy volunteers who have a clinically relevant surgical history.
6. Healthy volunteers who have a clinically relevant family history.
7. Healthy volunteers who have a history of relevant atopy including any confirmed significant allergic reactions (urticaria or anaphylaxis) against any drug, or multiple drug allergies (non-active hay fever is acceptable).
8. Healthy volunteers who have a history of relevant drug hypersensitivity.
9. Healthy volunteers who have a history of alcoholism.
10. Healthy volunteers who have a history of drug abuse.
11. Healthy volunteers who have any known factor, condition, or disease that might interfere with treatment compliance, study conduct or interpretation of the results such as drug or alcohol dependence or psychiatric disease.
12. Healthy volunteers who test positive for alcohol and drugs of abuse at Screening and on each admission. Note Alcohol will not be allowed from at least 48 hours before Screening and prior to every return visit;
13. Healthy volunteers who consume more than 14 units of alcohol a week. (unit=1 glass of wine (125 mL)=1 measure of spirits=½ pint of beer).
14. Healthy volunteers who smoke, or have smoked cigarettes (or equivalent) and/or using or have used nicotine-based products within 6 months prior to admission.
15. Healthy volunteers who demonstrate excess in xanthine consumption (more than 8 cups of coffee or equivalent per day).
16. Healthy volunteers who have a significant infection or known inflammatory process on Screening.
17. Healthy volunteers who have acute GI symptoms at the time of Screening or admission (e.g., nausea, vomiting, diarrhea, heartburn).
18. Healthy volunteers who have an acute infection such as influenza at the time of Screening or admission.
19. Healthy volunteers who do not agree to use highly effective medically acceptable methods of contraception.
20. Healthy volunteers whose results from clinical laboratory safety tests are outside the local reference range at Screening and on admission
21. Healthy volunteers who have a positive hepatitis B surface antigen, hepatitis C antibody, hepatitis B core antibody, hepatitis C antibody, or human immunodeficiency virus (HIV) antibody, SARS-CoV-2 infection at any time or other known infection requiring antibiotic therapy within the last 3 months prior to the study.
22. Healthy volunteers who have a positive QuantiFERON gold test and/or a tuberculosis history.
23. Healthy volunteers whose Screening supine BP ≥140 mm Hg (systolic) or ≥90 mm Hg (diastolic), following at least 5 minutes of supine rest. If BP is ≥140 mm Hg (systolic) or ≥90 mm Hg (diastolic), the BP should be repeated 2 more times and the average of the 3 BP values should be used to determine the HVs eligibility.
24. Healthy volunteers whose Screening supine 12-lead ECG demonstrating a QTc interval >450 msec or a QRS interval >120 msec. If QTc exceeds 450 msec, or QRS exceeds 120 msec, the ECG should be repeated 2 more times and the average of the 3 QTc or QRS values should be used to determine the HV's eligibility.
25. Healthy volunteers who have used any prescribed medications within 30 days of investigational product administration, or less than 5 half-lives (whichever is longer).
26. Healthy volunteers who have taken non-steroidal anti-inflammatory drugs within 30 days of investigational product administration, or less than 5 half-lives (whichever is longer).
27. Healthy volunteers who have used over the counter medication excluding routine vitamins and acetaminophen but including megadose (intake of 20 to 600 times the recommended daily dose) vitamin therapy within 7 days of first dosing.
28. Healthy volunteers who have participated in any investigational drug or device clinical study within 3 months prior to first dosing on this study.
29. Healthy volunteers who have previously participated in a study with an investigational product or device involving the dosing of a biological targeted at any immune pathway within 1 year prior to Screening.
30. Healthy volunteers who have received the last dose of investigational product greater than 3 months ago but who are on extended follow-up.
31. Healthy volunteers who have previously received KT-474 in either another study or another cohort in this study.
32. Healthy volunteers who have lost or donated of blood over 500 mL within 3 months prior to Screening or intention to donate blood or blood products during the study.
33. Healthy volunteers who have consumed grapefruit, grapefruit juice, Seville oranges, Seville orange marmalade, and Seville orange juice or other products containing grapefruit or Seville oranges from 7 days prior to admission to the study center and for the duration of the residential period.
34. Healthy volunteers who are Investigator site staff members directly involved in the conduct of the study and their family members, site staff members otherwise supervised by the Investigator, or study participants who are employees, including their family members, directly involved in the conduct of the study.
35. Healthy volunteers who are vegans or have medical dietary restrictions.
36. Healthy volunteers who cannot communicate reliably with the Investigator.
37. Healthy volunteers who are unlikely to co-operate with the requirements of the study.

For Patients (Part C)

Patients meeting any of the following criteria will be excluded from the study—
1. Has any clinically significant medical disorder, condition, disease (including active or potentially recurrent dermatological conditions other than AD or HS), significant physical examination or laboratory findings that may interfere with study objectives, in the Investigator's opinion (eg, conditions or findings that may expose a patient to unacceptable risk by study participation, confound the evaluation of treatment response or adverse events, or otherwise interfere with a patient's ability to complete the study).
2. Has unstable AD or HS or a consistent requirement for strong to strongest potency topical corticosteroids to manage AD or HS signs and symptoms.

3. Has an active systemic or localized infection, including known actively-infected AD or HS.
4. Has a history or evidence of clinically significant or severe allergies (eg, seasonal, pet-dander, environmental, food) requiring acute or chronic treatment (patients with allergic rhinitis who do not require treatment, or for whom an ongoing allergy treatment meets the definition of a stable regimen under Concomitant Treatment(s) section, may be eligible to participate in the study).
5. Has a history of recent (within 4-weeks of Day 1) sunbathing, tanning bed use, or ultraviolet (UV) light B therapy or psoralen plus UV A (sunbathing, tanning bed use, and UV light therapy are prohibited during the study).
6. Has any planned surgical or medical procedure that would overlap with study participation from Screening through the end of study.
7. Has any cancer or have a history of cancers within the last 5 years (except curatively treated with surgical excised squamous cell carcinoma, basal cell carcinoma, or carcinoma in situ of the skin or cervix).
8. Has a known sensitivity to any of the components of the investigational product.
9. A positive urine drug test.
10. History of regular alcohol consumption exceeding 7 drinks/week for female patients or 14 drinks/week for male patients (1 drink=5 ounces [150 mL] of wine or 12 ounces [360 mL] of beer or 1.5 ounces [45 mL] of hard liquor) within 6 months before Screening.
11. Treatment with an investigational product within 30 days or 5 half-lives preceding the first dose of investigational product (whichever is longer).
12. Treatment with CYP3A4 and P-gp inhibitors within 30 days or 5 half-lives preceding the first dose of investigational product (whichever is longer).
13. Screening supine BP ≥140 mm Hg (systolic) or ≥90 mm Hg (diastolic), following at least 5 minutes of supine rest. If BP is ≥140 mm Hg (systolic) or ≥90 mm Hg (diastolic), the BP should be repeated 2 more times and the average of the 3 BP values should be used to determine the patient's eligibility.
14. Screening supine 12-lead ECG demonstrating a QTc interval >450 msec or a QRS interval >120 msec. If QTc exceeds 450 msec, or QRS exceeds 120 msec, the ECG should be repeated 2 more times and the average of the 3 QTc or QRS values should be used to determine the patient's eligibility.
15. Patients with any of the following abnormalities in clinical laboratory tests at Screening, as assessed by the study-specific laboratory and confirmed by a single repeat test, if deemed necessary: a) Aspartate aminotransferase or ALT level ≥1.5×ULN; b) Total bilirubin level ≥1.5×ULN; patients with a history of Gilbert's syndrome may have direct bilirubin measured and would be eligible for this study provided the direct bilirubin level is ≤ULN.
16. Use of prescription or nonprescription drugs including topical corticosteroids, vitaminic and dietary supplements within 14-days or 5 half-lives (whichever is longer) prior to the first dose of investigational product. As an exception, acetaminophen/paracetamol may be used (only if necessary) at doses of ≤1 g/day. Limited use of nonprescription medications that are not believed to affect patient safety or the overall results of the study may be permitted on a case-by-case basis following approval by the Sponsor. Herbal supplements (including St. John's Wort) must have been discontinued at least 28-days prior to the first dose of investigational product.
17. Pregnant female patients; breastfeeding female patients; female patients of childbearing potential who are unwilling or unable to use a highly effective method of contraception as outlined in this protocol for the duration of the study and for at least 90 days after the last dose of investigational product.
18. Blood donation (excluding plasma donations and platelet donations) of approximately ≥400 mL within 3 months or ≥200 mL within a month prior to dosing.
19. History of sensitivity to heparin or heparin-induced thrombocytopenia.
20. History of HIV, hepatitis B, hepatitis C, or syphilis; positive testing for HIV, hepatitis B virus surface antigen, hepatitis B virus core antibody, hepatitis C virus antibody, syphilis, or SARS-CoV-2 infection.
21. Unwilling or unable to comply with the criteria in this protocol.
22. Patients who are Investigator site staff members directly involved in the conduct of the study and their family members, site staff members otherwise supervised by the Investigator, or patients who are employees, including their family members, directly involved in the conduct of the study.
23. Other acute or chronic medical or psychiatric condition including recent (within the past year) or active suicidal ideation or behavior or laboratory abnormality that may increase the risk associated with study participation or investigational product administration or may interfere with the interpretation of study results and, inNIV the judgment of the Investigator, would make the patient inappropriate for entry into this study.

Treatment Groups and Duration of Study: The 2 treatment groups were Compound A group and the placebo group.

Part A: Screening (26 days), Confinement before treatment (2 days), Treatment (1 day), Confinement after treatment (5 days), and follow-up (13 days).

Part B: Screening (26 days), Confinement before treatment (2 days), Treatment (14 days), Confinement after treatment (7 days) and follow-up (7 days).

Part C: Screening (40 days), Confinement before treatment (2 days), Treatment (14 days), and follow-up (14 days).

Study Objectives:

Primary Objective:
To determine the safety and tolerability of Compound A when administered as single and multiple oral doses at escalating dose levels in HVs and following multiple doses in patients with AD or HS Secondary Objective:
To characterize the PK profile of Compound A and its diastereomers Compound B and Compound C, following single and multiple doses of Compound A in HVs and following multiple doses in patients with AD or HS Exploratory Objectives:
To characterize the PD profile of Compound A following single and multiple doses in HVs and following multiple doses in patients with AD or HS.
To characterize the concentration of Compound A in skin following multiple doses in HVs and patients with AD or HS.
To evaluate the effect of food on the PK profile of Compound A and its diastereomers Compound B and Compound C following a single dose of Compound A in HVs.

To evaluate the metabolite profile of Compound A following multiple doses of Compound A in HVs.

To assess blood and skin for messenger ribonucleic acid (mRNA) for candidate biomarkers following multiple doses of Compound A in HVs and patients with AD or HS.

Study Endpoints:

Primary Endpoints:
- Treatment-emergent (serious) adverse events ([S]AEs)
- Concomitant medication
- Clinical laboratory tests
  - Hematology
  - Coagulation
  - Chemistry
  - Urinalysis and urine microscopy
- Vital signs
  - Pulse Rate (bpm)
  - Systolic blood pressure (BP) (mm Hg)
  - Diastolic BP (mm Hg)
  - Respiratory rate
  - Temperature
- Safety electrocardiogram and Holter monitoring
  - Heart Rate (bpm), PR, QRS, QT, QTcF Secondary Endpoints:
- Pharmacokinetic evaluations in HVs and patients with AD or HS The following (but not limited to) plasma PK parameters of Compound A, Compound B, and Compound C will be calculated as appropriate:
  - Area under the plasma concentration-time curve from time zero to infinity [AUC(0-∞)] (single dose only), area under the plasma concentration-time curve from time zero to last measurable concentration [AUC(0-last)], area under the concentration-time curve during a dosing interval [AUC(0-tau)], maximum observed concentration (Cmax), time to Cmax (tmax), apparent clearance (CL/F), apparent volume of distribution (Vz/F), terminal half-life (t1/2), mean residence time (MRT), and dose-normalized AUC and Cmax
  - Following repeat dosing only, accumulation ratios (RAUC, RCmax), average concentration over the dosing interval (Cavg), and concentration at the end of dose interval (Ctrough)
  - Diastereomer Ratio: ratios of the diastereomers Compound B versus Compound C (Cmax, AUC, and concentration for each sampling time) The following (but not limited to) urine PK parameters of Compound A, Compound B, and Compound C in SAD and MAD cohorts will be calculated as appropriate:
  - By-collection-interval and cumulative amount: of unchanged drug excreted in urine [Ae(t1-t2), Ae(0-t)], fraction of unchanged drug [fe(t1-t2), fe(0-t)]
  - Renal clearance (CLR)

Exploratory Endpoints:

Primary Endpoints:
- Pharmacodynamic Endpoints
  - IRAK4 levels in whole blood by FLOW (Parts A, B, and C)
  - IRAK4 levels in peripheral blood mononuclear cells by mass spectrometry (MS) (Parts A, B, and C)
  - IRAK4 levels in skin punch biopsies by MS and immunofluorescence (Parts B and C)
  - Proinflammatory cytokines and chemokines in skin punch biopsies by MS and gene expression profiling (GEP) (Part B and C)
  - Proinflammatory cytokine and chemokine production following ex vivo stimulation of whole blood by Luminex (Parts A and B)
  - Plasma high-sensitivity C-reactive protein levels by Luminex (Parts B and C)
  - Plasma serum amyloid A and proinflammatory cytokines which may include but are not limited to tumor necrosis factor-α, interleukin (IL)-6, IL-10, IL-4 and IL-5 by Luminex and enzyme-linked immunosorbent assay (Part C only)
  - Changes in mRNA levels by RNAseq in PBMCs (Parts B and C)
- Pharmacokinetic Endpoints
  - AUC(0-∞), AUC(0-last), Cmax, tmax, CL/F, Vz/F, t1/2, MRT, F (relative bioavailability fed/fasted), and dose-normalized AUC and Cmax, of Compound A, Compound B, and Compound C as appropriate for the FE study.
  - Metabolic profiling (metabolites in safety testing [MIST] analysis) will be conducted on the PK samples from 2 high dose HV MAD cohorts after the study is completed and will not be part of the clinical study report.
  - Compound A concentration in skin punch biopsies (Parts B and C)

Statistical Methods:

Safety and Tolerability

All data will be fully listed. The reporting of the safety data of all study participants receiving at least 1 dose of Compound A or placebo will include the incidence and type of AEs, plus absolute values and changes in BP, heart rate, oral temperature, clinical laboratory data, physical examination, neurological examination data, and 12-lead electrocardiogram data from pre-dose to post-dose time points.

Pharmacokinetics

Analysis of the PK data will be performed for all study participants receiving a dose of Compound A. Pharmacokinetic parameters of Compound A, Compound B, and Compound C will be summarized, and descriptive statistics (including mean, median, standard deviation and coefficient of variation) will be generated for each dose group. The graphical assessment of dose proportionality will be performed for AUC and Cmax. Relative bioavailability of food effect will be assessed based on AUC and Cmax.

Pharmacodynamics

Pharmacodynamic analyses will be performed for all study participants receiving at least one dose of Compound A or placebo. The analysis of IRAK4 levels and modulation of proinflammatory cytokine and chemokine assessments will be considered exploratory. A mixed effects Analysis of Variance model will be used to compare the on-treatment IRAK4 levels of active versus placebo. The baseline IRAK4 levels will be used as a covariate in the model. The placebo-treated study participants will be pooled across cohorts and used as a single treatment group for comparison to each active treatment group.

Phase 1 SAD Results:

Phase 1 SAD results included data from the seven Compound A single dose cohorts, comprising 57 healthy volunteer subjects randomized 6:2 to either a single oral dose of Compound A or placebo. The data demonstrated robust, dose-dependent IRAK4 reduction, maintained for up to 6 days, in PBMCs measured by mass spectrometry, resulting in median IRAK4 reduction from baseline of 94-96% achieved at 48 hours post-dose at the top three dose levels, achieving strong proof-of-mechanism (Table 4). Flow cytometry demonstrated that the effect of Compound A on IRAK4 levels was similar in lymphocytes and monocytes.

TABLE 4

Percent IRAK4 Change from Baseline in PBMCs at 48 Hours Post-Dose using Mass Spectrometry

| Cohort | Placebo (n = 13) | Cohort 1 (n = 6) | Cohort 2 (n = 6) | Cohort 3 (n = 6) | Cohort 4 (n = 6) | Cohort 5 (n = 7) | Cohort 6 (n = 5) | Cohort 7 (n = 6) |
|---|---|---|---|---|---|---|---|---|
| Compound A dose | — | 25 mg | 75 mg | 150 mg | 300 mg | 600 mg | 1000 mg | 1600 mg |
| Median IRAK4 Change | −2% | −39% (p = 0.1) | −75% (p < 0.0001) | −82% (p < 0.0001) | −89% (p < 0.0001) | −96% (p < 0.0001) | −94% (p < 0.0001) | −95% (p < 0.0001) |

Proof-of-biology was established with inhibition of ex vivo R848- or LPS-mediated induction of multiple proinflammatory cytokines in whole blood at doses and exposures associated with median IRAK4 reduction in PBMCs of ≥85% at 24-48 hours post-dose, with mean maximum cytokine inhibition of up to 97% (Table 5). Compound A demonstrated oral bioavailability, a half-life supportive of daily dosing, and dose-dependent plasma exposures that were less than dose-proportional at higher doses and plateaued after 1000 mg. Compound A was safe and well-tolerated; mild to moderate, self-limited headache and GI symptoms were the most common reported treatment-related adverse events, and there were no serious adverse events reported.

Consistent PK was observed after single dosing: Cmax achieved between 7-24 hours, half-life=25-40 hours. Increasing dose dependent exposure was observed plateauing after the 1000 mg dose with low to moderate inter-subject variability in exposure.

Figure 4:
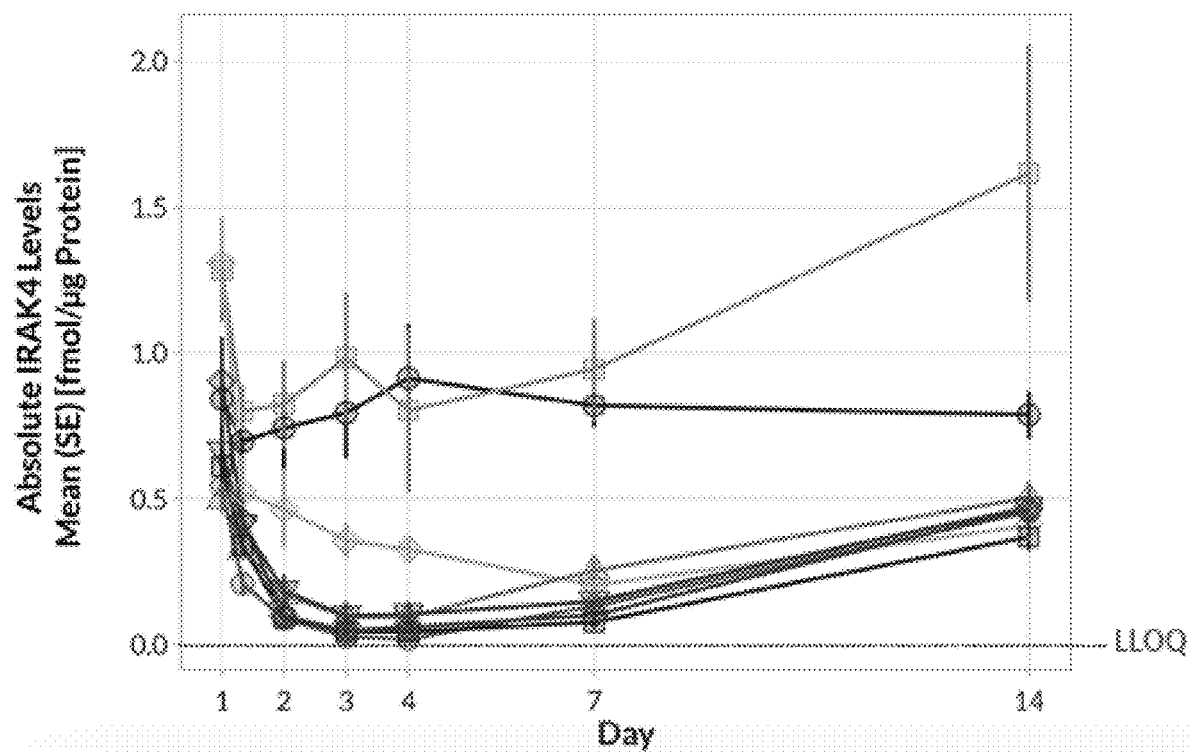
FIG. 4 shows that Compound A achieved deep and dose-dependent IRAK4 degradation after single oral dose that lasted for at least 6 days.
Figure 4:
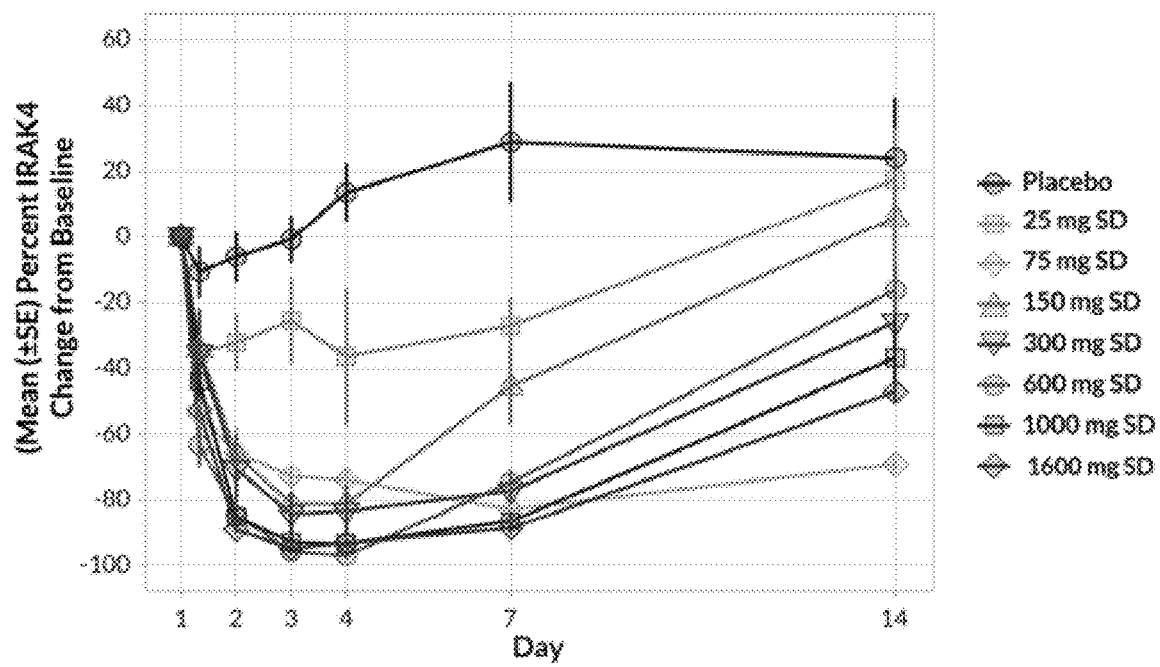
Figure 5:
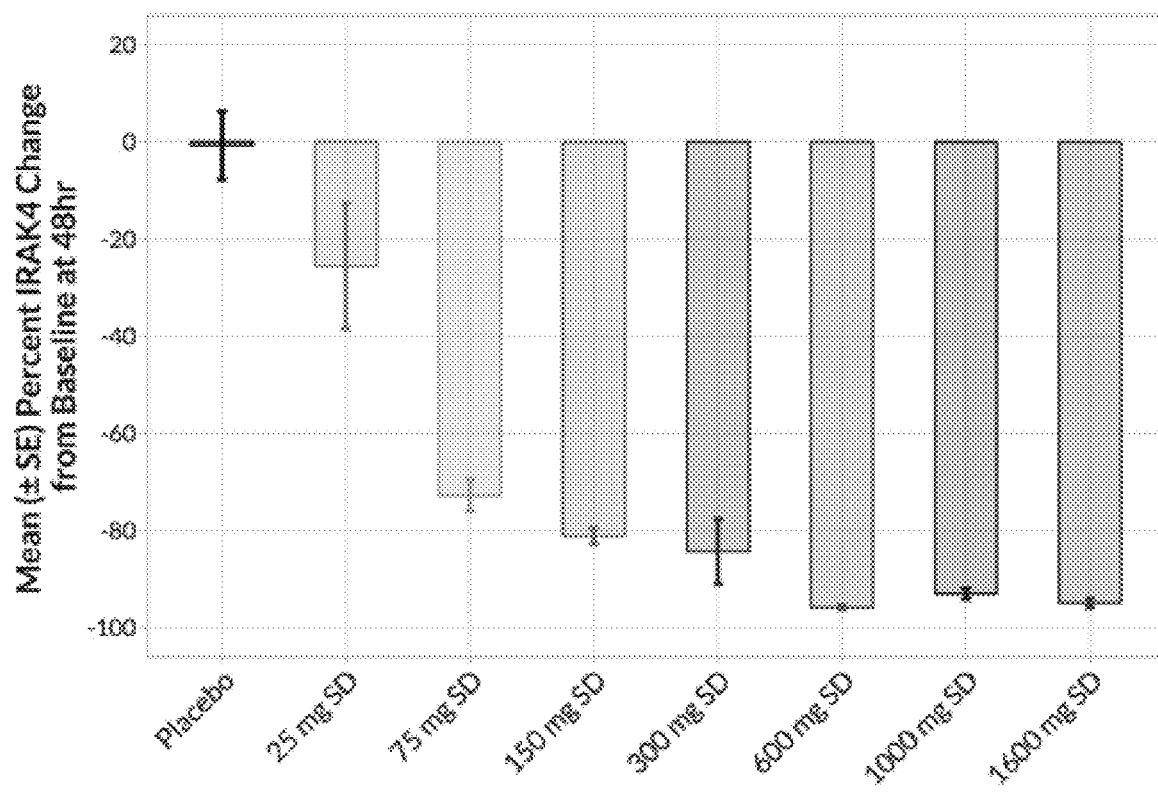
FIG. 5 shows that Compound A achieved >95% IRAK4 degradation after single dose.
Figure 6:
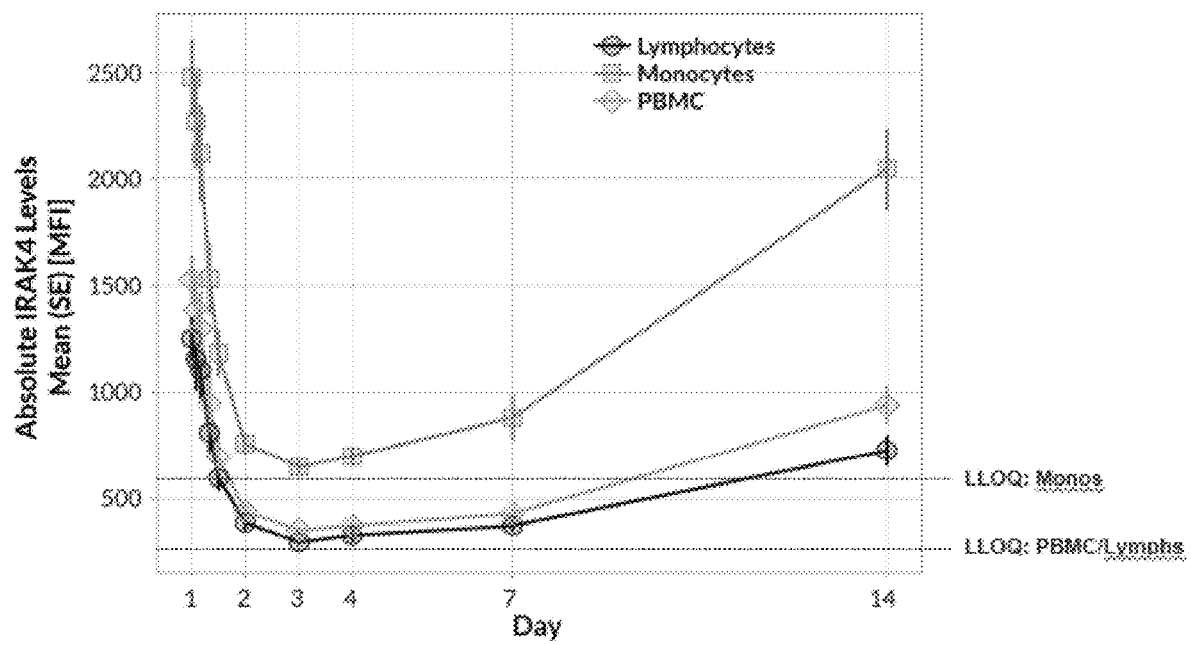
FIG. 6 shows robust IRAK4 degradation in lymphocytes and monocytes: flow cytometry results at SAD 7.
Figure 6:
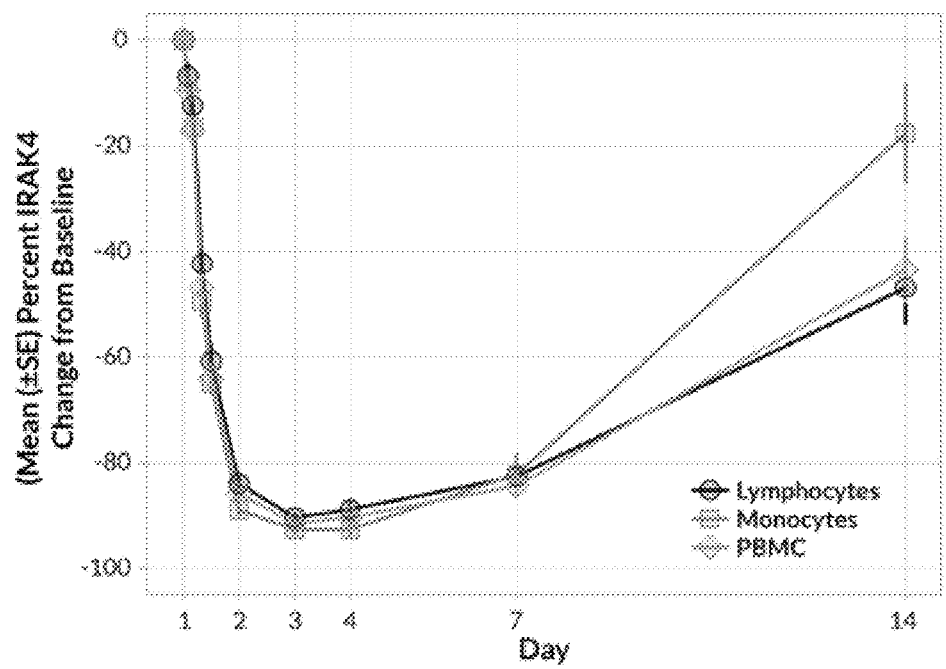
Figure 7:
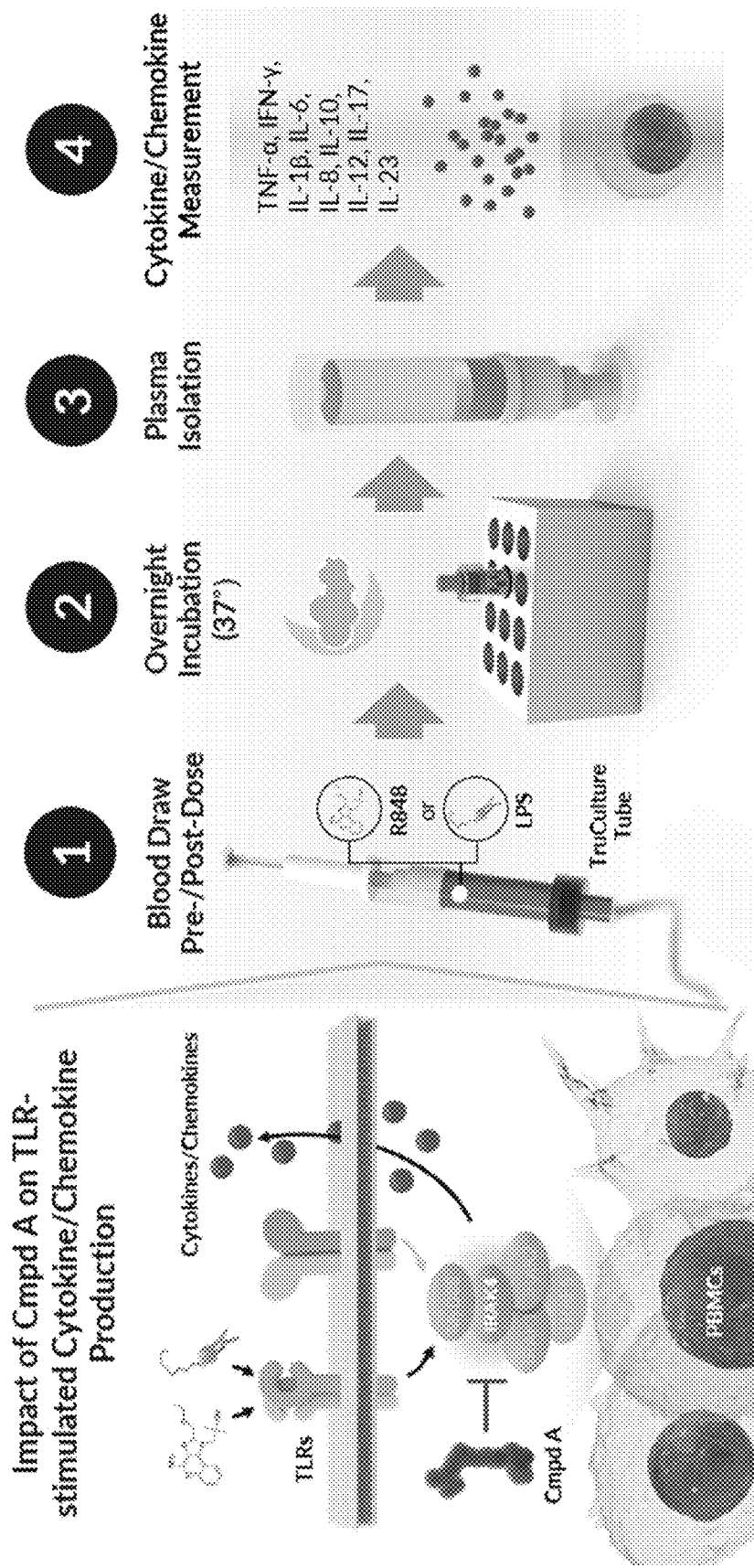
FIG. 7 depicts ex-vivo cytokine stimulation methodology used in the Compound A Phase 1 trial.
Figure 8:
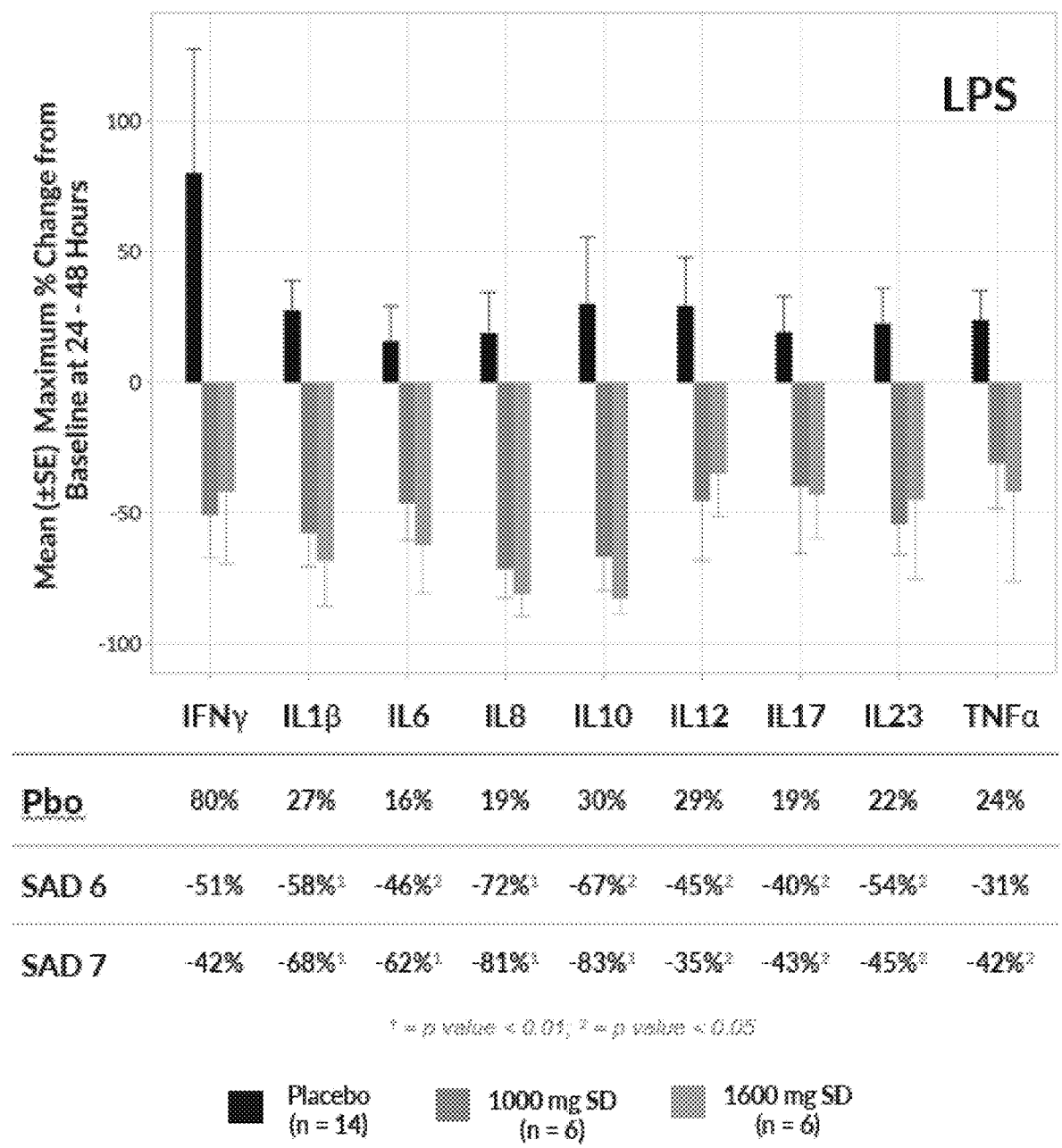
FIG. 8 shows up to 97% maximum ex vivo cytokine inhibition 24-48 h post-dose effect against LPS (TLR4)- or R848 (TLR7)-stimulated cytokine induction in whole blood.
Figure 8:
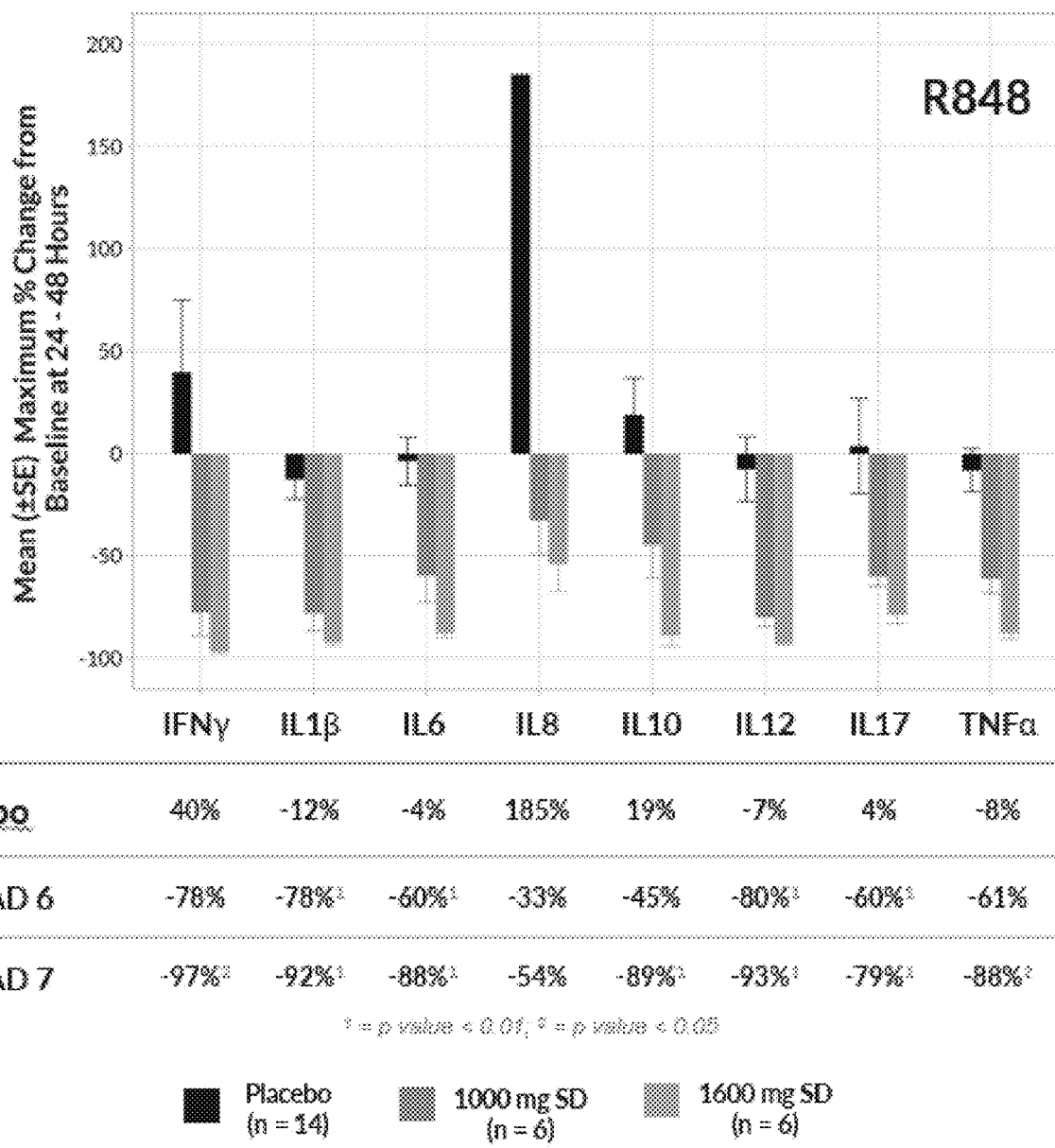

IRAK4 degradation results are shown in Table 7 and FIGS. 4-6. Degradation was detected by mass spectrometry in circulating PBMCs. IRAK4 levels nadired at 48-72 hours (Day 3-4) and IRAK4 reduction lasted for at least 6 days post-dose in all dose groups. SAD 5/6/7 reached the low limit of quantitation (LLOQ).

TABLE 5

Mean Maximum Percent Change from Baseline at 24-48 Hours in Ex Vivo Proinflammatory Cytokine Induction by R848 and LPS in Whole Blood at Cohort 7.

| Proinflammatory Cytokine | IFNγ | IL1β | IL6 | IL8 | IL10 | IL12 | IL17 | TNFα |
|---|---|---|---|---|---|---|---|---|
| R848 | −97%[2] | −92%[1] | −88%[1] | −54% | −89%[1] | −93%[1] | −79%[1] | −88%[2] |
| LPS | −42% | −68%[1] | −62%[1] | −81%[1] | −83%[1] | −35%[2] | −43%[2] | −42%[2] |

[1] = p value < 0.01;
[2] = p value < 0.05, for comparison to placebo

IRAK4 knockdown of ≥85% in vivo in circulating PBMCs leads to robust TLR/IL-1R pathway inhibition, as demonstrated by up to 97% suppression of ex vivo response of whole blood to TLR agonists. Daily dosing with Compound A is currently being evaluated in the multiple ascending dose (MAD) portion of the trial; based on the PK properties of the drug and the observed PK-PD relationship, similar levels of IRAK4 degradation and cytokine inhibition with substantially lower daily doses is possible. The potent, broad effect of IRAK4 knockdown on multiple different proinflammatory cytokines implicated in a variety of autoimmune inflammatory diseases highlights the potential for Compound A to be a first-in-class oral anti-inflammatory drug, especially in a shifting external landscape for safe, broadly active small molecule anti-inflammatory agents.

Figure 3:
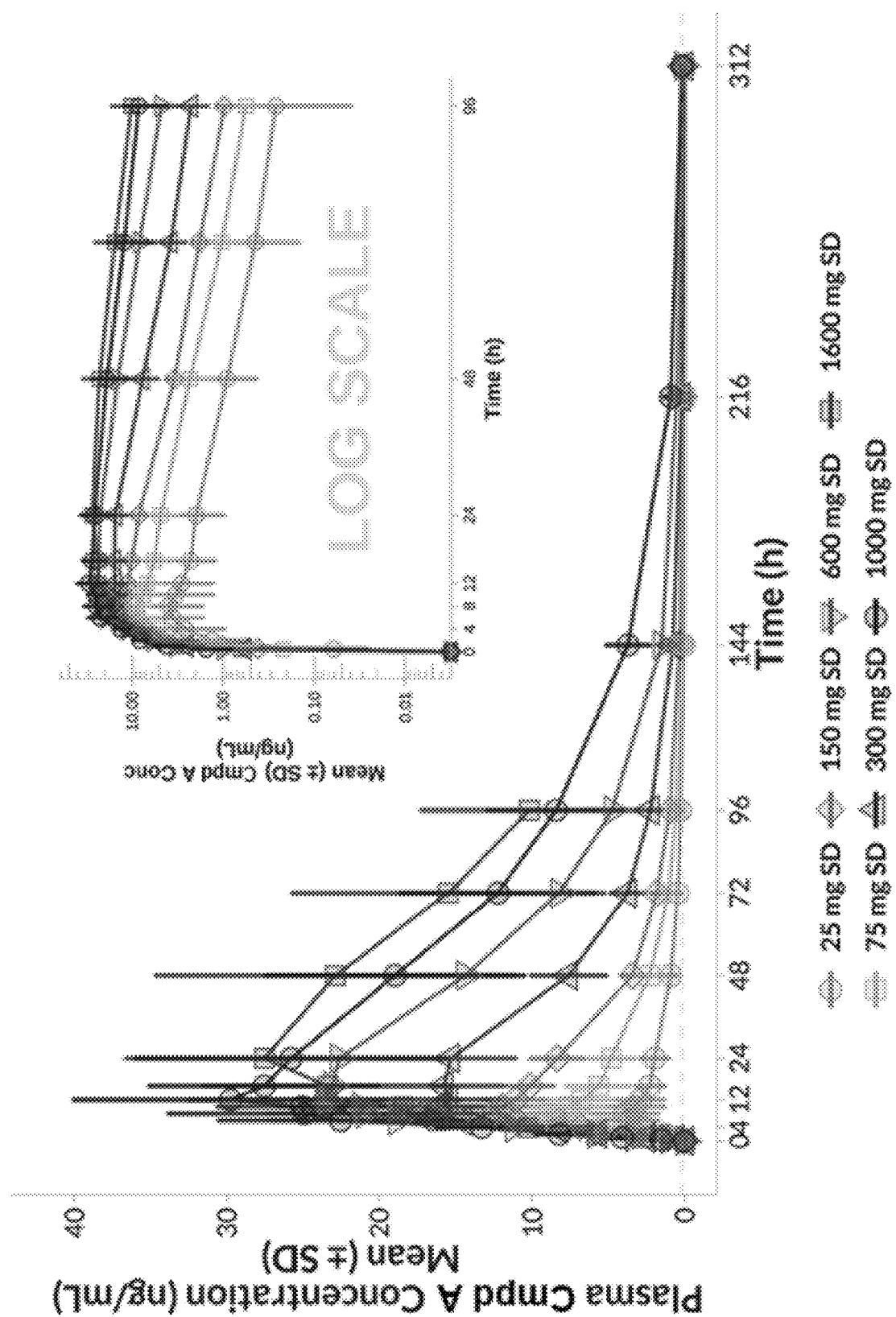
FIG. 3 depicts the Compound A pharmacodynamic (PK) results in the SAD study.

PK results are summarized in Table 6 and FIG. 3.

TABLE 7

Percent IRAK4 Reduction in PBMCs at 48 Hours Post-Dose using Mass Spectrometry

| | N | Mean IRAK4 Change | Median IRAK4 Change | p value |
|---|---|---|---|---|
| Placebo | 13 | −1% | −2% | — |
| 25 mg | 6 | −26% | −39% | 0.1 |
| 75 mg | 6 | −73% | −75% | <0.0001 |
| 150 mg | 6 | −81% | −82% | <0.0001 |
| 300 mg | 6 | −84% | −89% | <0.0001 |
| 600 mg | 7 | −96% | −96% | <0.0001 |

TABLE 6

PK Results

| SAD# | Dose | Cmax (ng/mL) | tmax (h) | AUC (ng · h/mL) | t½ (h) |
|---|---|---|---|---|---|
| 1 | 25 mg | 3.49 (61.2) | 8.0 (6.0-8.0) | 112 (65.4) | 25.2 (27.0) |
| 2 | 75 mg | 9.08 (36.6) | 7.0 (6.0-8.0) | 288 (36.7) | 28.7 (10.1) |
| 3 | 150 mg | 12.7 (25.7) | 9.0 (8.0-10.0) | 483 (21.9) | 31.6 (22.1) |
| 4 | 300 mg | 17.4 (29.6) | 8.0 (8.0-24.0) | 848 (30.4) | 26.6 (13.1) |
| 5 | 600 mg | 24.2 (27.5) | 12.0 (6.00-24.0) | 1520 (17.4) | 30.1 (47.2) |
| 6 | 1000 mg | 27.8 (34.4) | 20.0 (6.0-24.0) | 1950 (63.5) | 40.2 (25.9) |
| 7 | 1600 mg | 27.3 (36.2) | 24.0 (12.0-48.0) | 1920 (43.0) | 36.4 (46.9) |

TABLE 7-continued

Percent IRAK4 Reduction in PBMCs at 48
Hours Post-Dose using Mass Spectrometry

|  | N | Mean IRAK4 Change | Median IRAK4 Change | p value |
|---|---|---|---|---|
| 1000 mg | 5 | −93% | −94% | <0.0001 |
| 1600 mg | 6 | −95% | −95% | <0.0001 | p-values relative to placebo

Blinded SAD safety: No SAEs. All treatment-related AEs (Table 8) recovered or resolved. No study treatment-related AEs in any other cohorts.

Clinically relevant laboratory abnormalities: SAD 5: n=1; ALT elevation (2.5× ULN)-slow resolution to baseline and AST elevation (3.8× ULN) with resolution ~Day 21.

ECG results: No significant ECG changes and no clinically significant QTcF prolongation.

TABLE 8

Study Treatment Related AEs*

| AE Term | #AEs (subjects) | Severity | Cohort |
|---|---|---|---|
| Headache | 5 (4) | Moderate (x3) | SAD 5, SAD 5 FE, SAD 6 |
|  |  | Mild (x2) | SAD 5 |
| Nausea | 3 (3) | Mild | SAD 5 FE |
|  |  | Mild (x2) | SAD 6 |
| Diarrhea | 2 (2) | Mild | SAD 5 |
|  |  | Mild | SAD 5 FE |
| Vomiting | 2 (1) | Mild (x2) | SAD 5 FE |
| Abdominal pain | 1 | Mild | SAD 5 |
| Palpitations | 1 | Mild | SAD 5 |
| Muscle weakness | 1 | Mild | SAD 6 |
| Myalgia | 1 | Mild | SAD 6 |

*per Investigator assessment

SAD Summary:

Single doses were well-tolerated in the SAD Phase 1 study, with mild-moderate self-limiting headache and GI symptoms the most common treatment-related AEs seen at doses ≥600 mg. Administration of Compound A was robust, dose-dependent and maintained (up to 6 days) IRAK4 reduction in PBMCs, with median 94-96% KD (reaching limit of quantification) at 48 hours plateauing after 600 mg. Proof-of-biology was established with demonstration of broad and potent ex vivo cytokine inhibition in whole blood. Up to 79-97% inhibition of R848 or LPS induction of 8 different pro-inflammatory cytokines, including: IFN-g (97%), IL-12 (93%), IL-1b (92%), IL-10 (89%), IL-6 (88%), TNF-α (88%), IL-8 (81%) and IL-17 (79%) was observed. Maximum cytokine effects were seen with Compound A exposures corresponding to >85% degradation in PBMCs. The Compound A SAD Phase 1 results demonstrate degrader proof-of-mechanism and proof-of-biology for target protein degradation in a placebo-controlled study.

Figure 9:
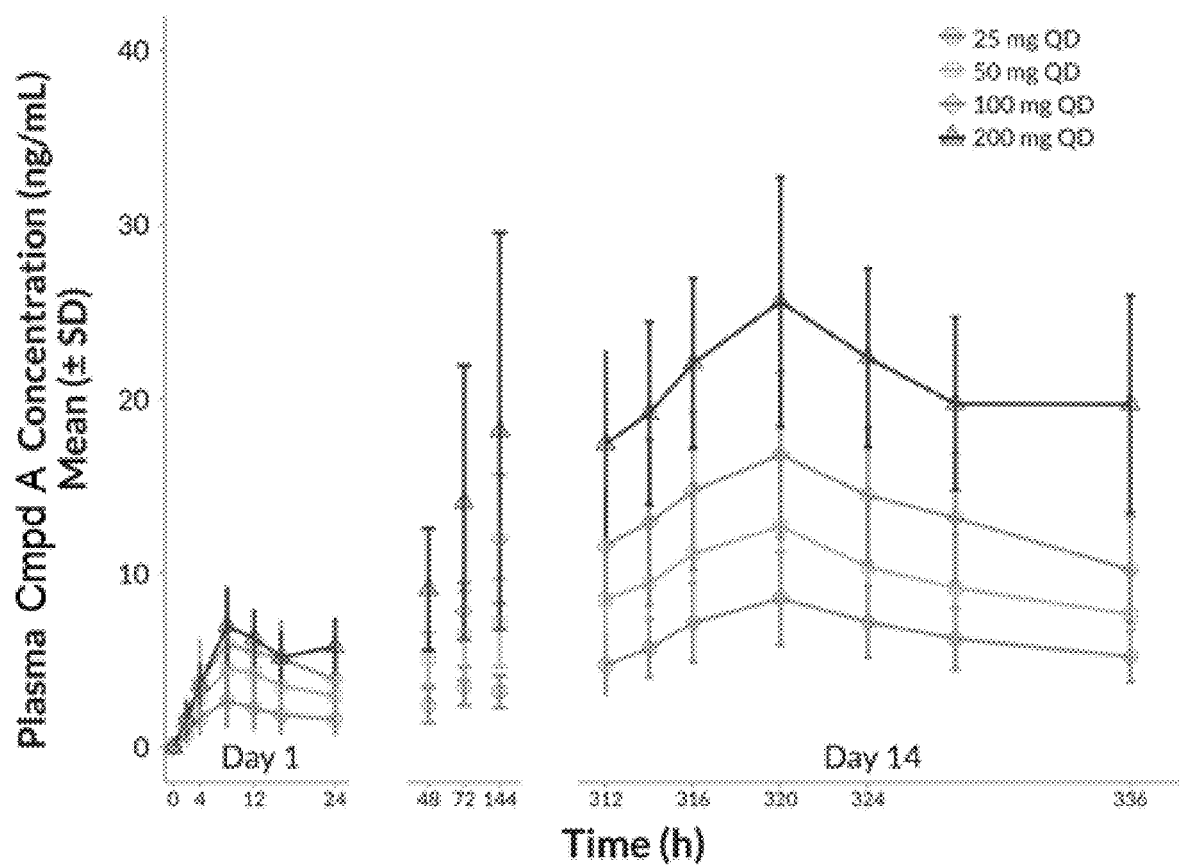
FIG. 9 shows Compound A plasma concentration in the MAD study.

Phase 1 MAD Results:

Phase 1 MAD results included data from four Compound A multiple dose cohorts MAD 1-4 (25 mg, 50 mg, 100 mg, and 200 mg QD). The MAD portion of study showed that once daily dosing of Compound A resulted in high steady-state exposures (FIG. 9).

TABLE 9

Steady-State (Day 14) PK Parameters

| PK Parameter | 25 mg QD (n = 9) | 50 mg QD (n = 9) | 100 mg QD (n = 9) | 200 mg QD (n = 9) |
|---|---|---|---|---|
| Cmax (ng/mL) | 8.20 (34.5) | 12.0 (39.1) | 16.1 (32.0) | 25.2 (26.7) |
| $t_{max}$ (h) | 8.00 (4.0-8.0) | 8.00 (8.0-8.0) | 8.00 (8.0-12) | 8.00 (8.0-12) |
| AUC24 (ng*h/mL) | 153 (30.8) | 224 (39.4) | 314 (29.9) | 498 (24.0) |
| $C_{trough}$ (ng/mL) | 5.03 (30.3) | 7.28 (35.1) | 9.81 (30.1) | 18.8 (32.6) |
| Day 14/1 Ratio$_{Cmax}$ | 3.73 (47.1) | 2.64 (26.3) | 2.92 (37.7) | 3.51 (34.7) |
| Day 14/1 Ratio$_{AUC}$ | 4.01 (41.2) | 2.97 (23.2) | 3.29 (38.9) | 4.22 (28.8) |

Geometric Mean (% CV) reported for all parameters, except tmax where median (range) are presented. Accumulation Ratio represents fold change in exposure from Day 1 to Day 14.

Compound A showed a 3- to 4-fold increase in exposure on Day 14 and Day 14 $C_{trough}$ occurred in range where >90% IRAK4 degradation was expected. Steady-state was reached by Day 7 of dosing.

Figure 10:
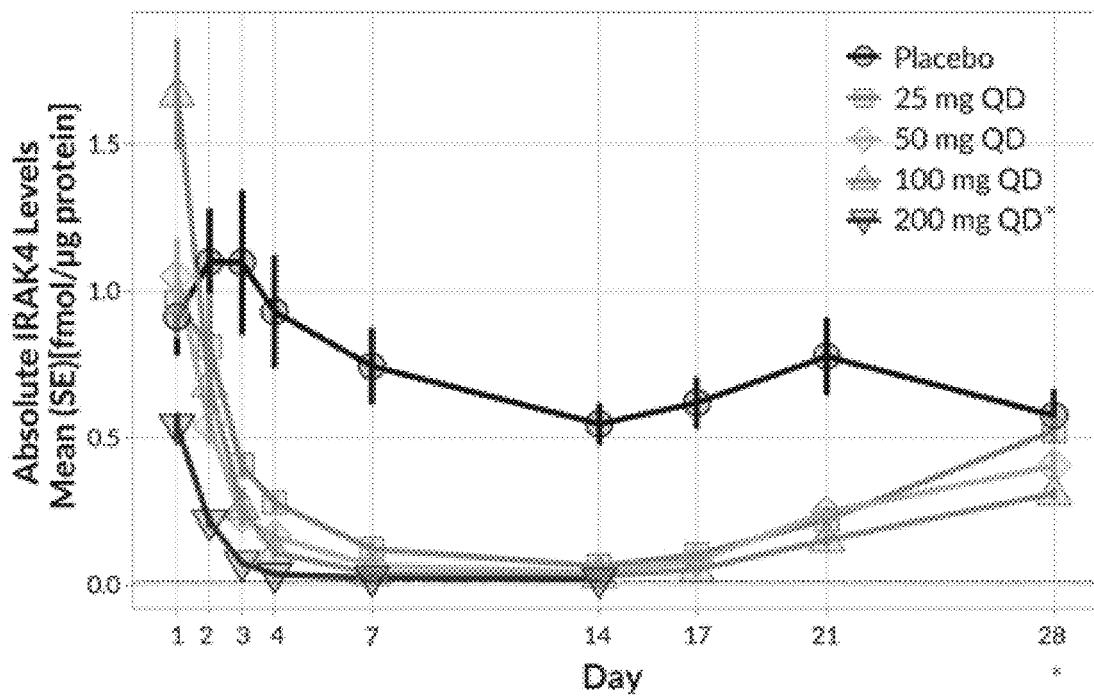
FIG. 10 shows robust IRAK4 degradation in lymphocytes and monocytes in the MAD study. *Data for 200 mg QD only to Day 14.
Figure 10:
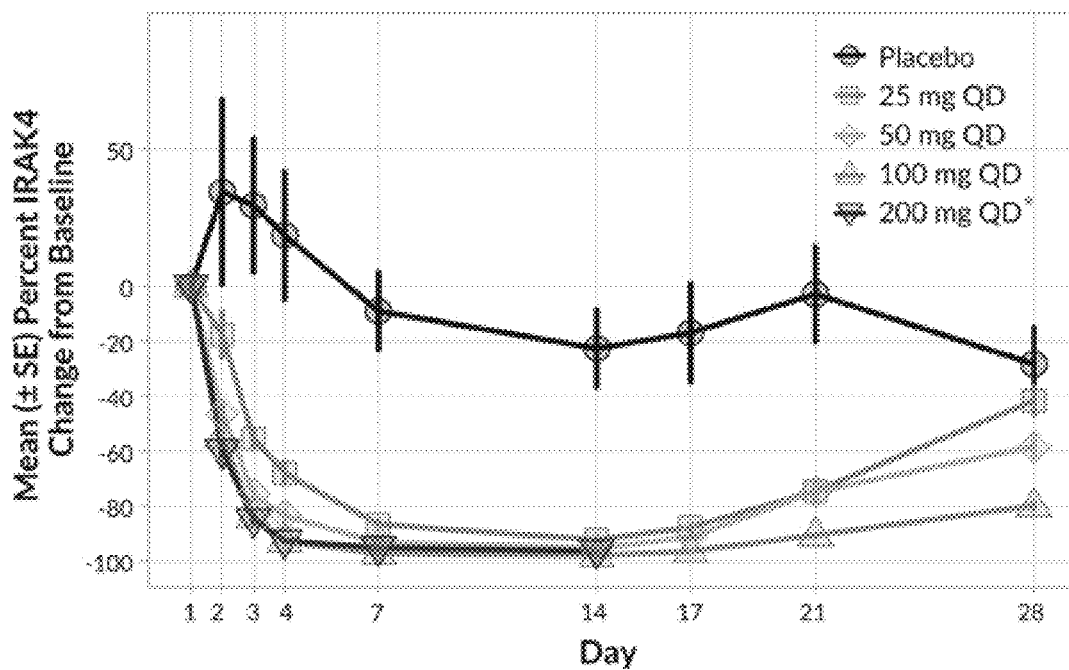

FIG. 10 shows that Compound A achieved complete and sustained IRAK4 degradation with multiple daily oral doses (14 Days). IRAK 4 degradation was detected by mass spectrometry in circulating PBMC. Steady state IRAK4 reduction achieved between Days 7 and 14 and recovery towards baseline by Day 28 (2 weeks after last dose). 3 of the MAD cohorts (MAD 2 through 4) approached or exceeded Lower Limit of Quantitation (LLOQ).

FIG. 11 shows that lower doses of Compound A achieve >98% IRAK4 degradation by mass spectroscopy and a plateau in IRAK4 reduction in PBMC after 100 mg dosing.

FIG. 12 shows that Compound A achieved >90% degradation in monocytes at ≥100 mg detected by flow cytometry and maximal degradation in monocytes was observed in 200 mg dosing at Day 14.

Figure 13:
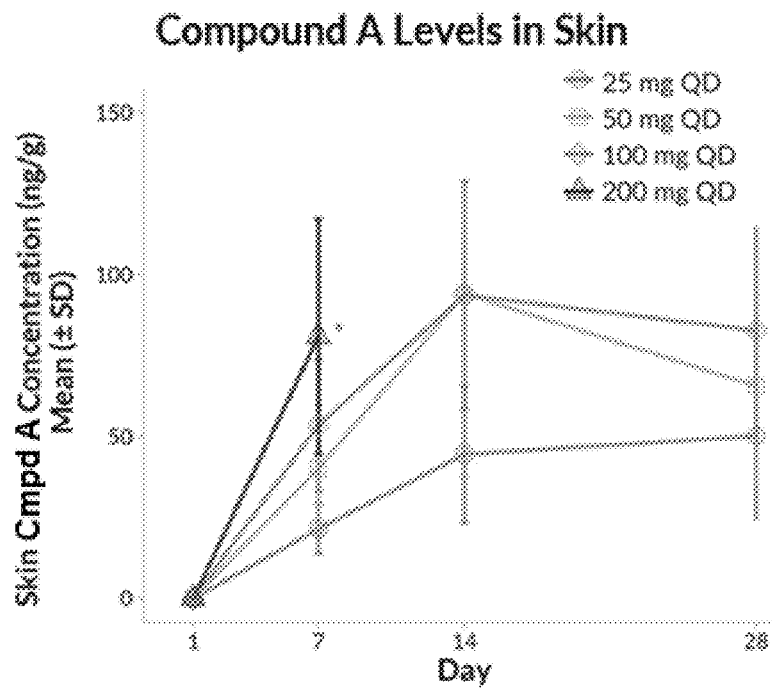
FIG. 13 shows that once daily dosing of Compound A resulted in high skin exposures.
Figure 13:
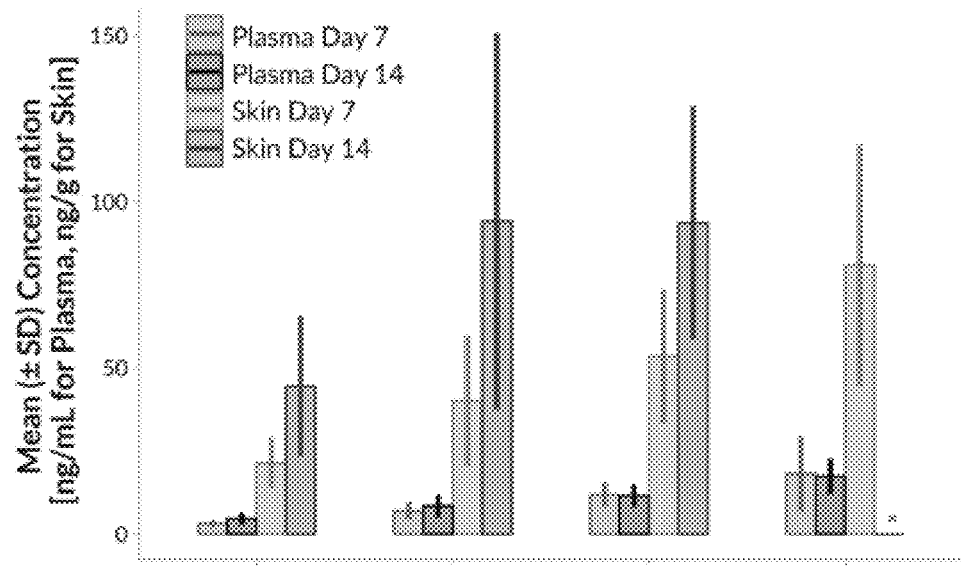

FIG. 13 shows that once daily dosing resulted in high skin exposures exceeding plasma. Results show increasing exposures through Day 14 with $C_{trough}$ levels in skin ~10-fold higher than plasma on Day 14.

Figure 14:
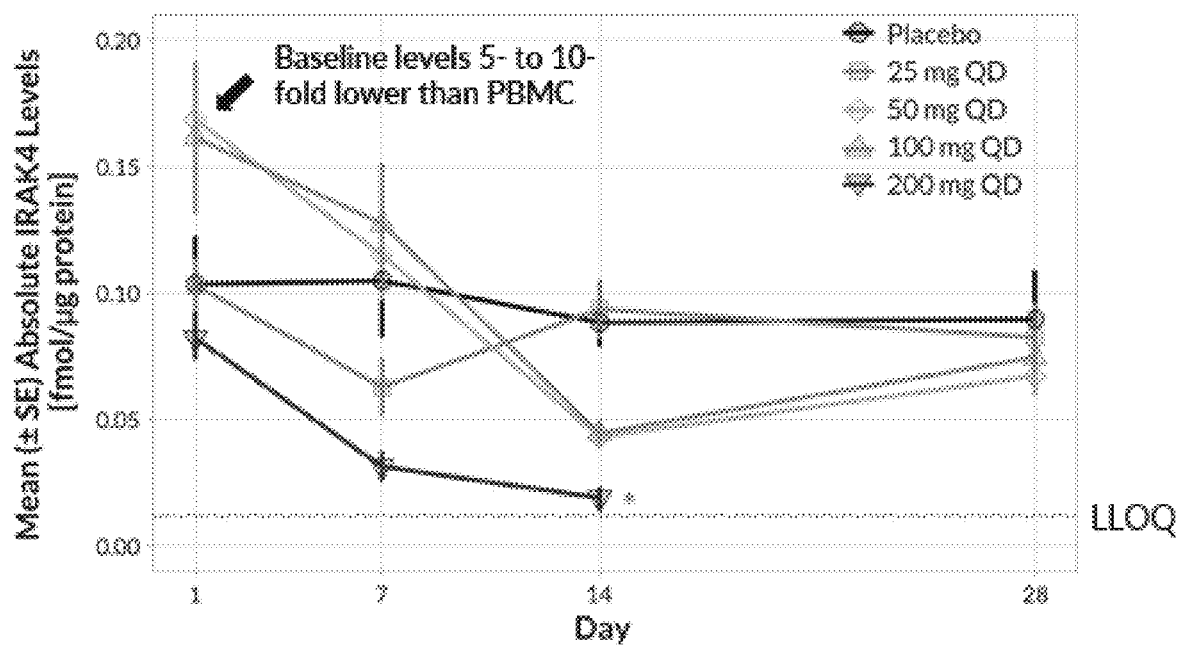
FIG. 14 shows that once daily dosing of Compound A resulted reduced IRAK4 levels in skin.
Figure 14:
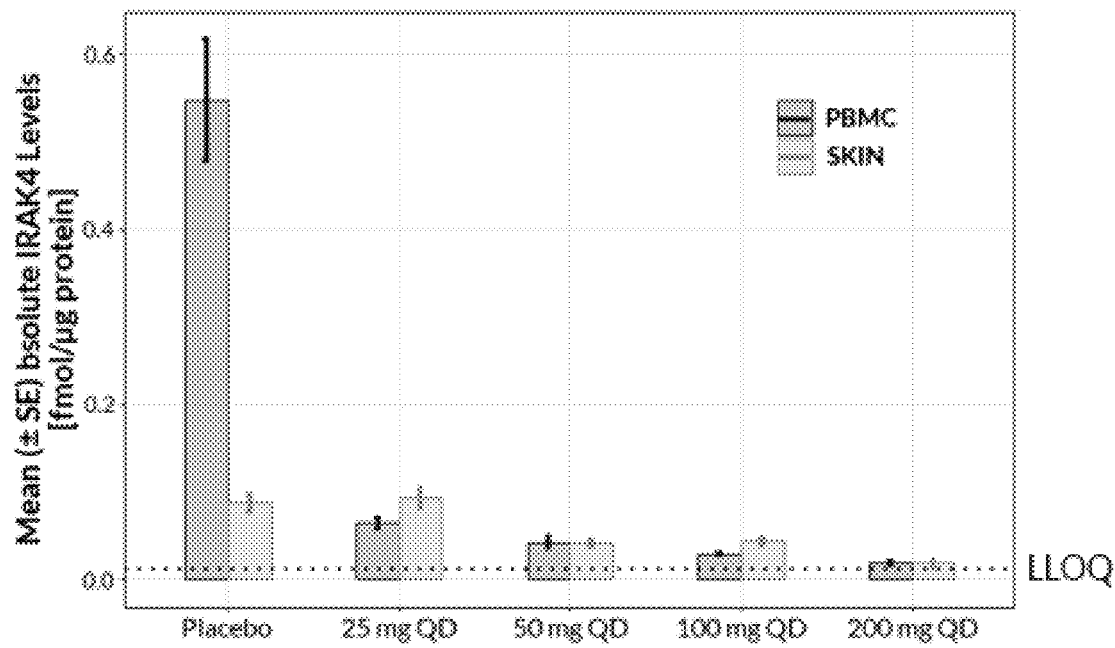

FIG. 14 shows that Compound A at 200 mg dosing reduced IRAK4 near LLOQ by Day 14 in skin determined by mass spectroscopy, with knockdown up to 90% at 200 mg. The baseline IRAK4 levels in skin were substantially lower compared to PBMC. Comparable degradation in PBMC shows the effect of Compound A is independent of baseline expression level.

Figure 15:
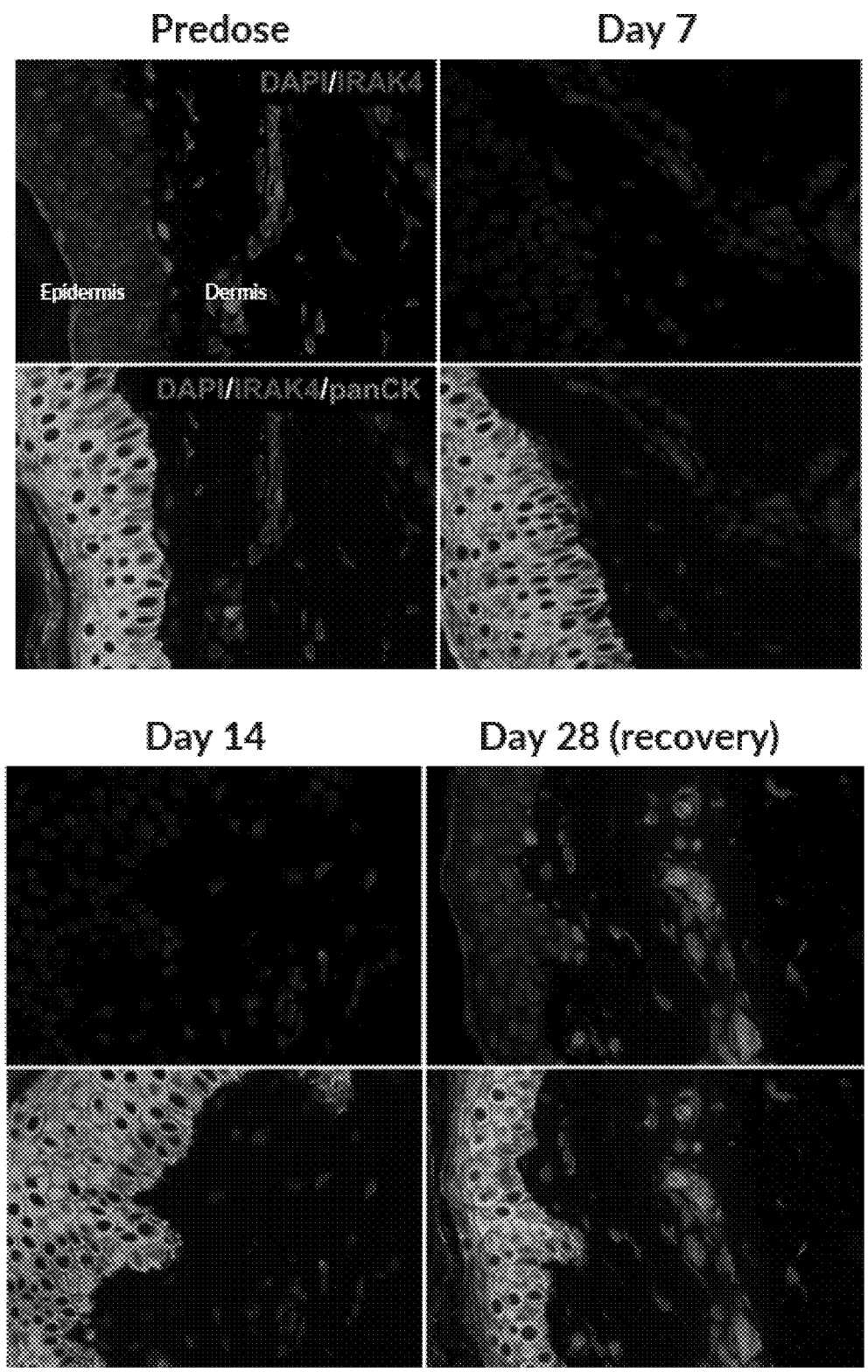
FIG. 15 shows images of substantial IRAK4 degradation in skin dermis and epidermis.

FIG. 15 shows substantial IRAK4 degradation in skin dermis and epidermis.

FIG. 16 shows ex vivo cytokine inhibition across nine disease relevant cytokines and chemokines at Day 7-14.

MAD Summary:

Multiple daily doses over 14 days up to 200 mg (MAD 4) were safe and well-tolerated. Steady-state plasma levels were reached by Day 7, with approximately 3-fold increase in exposure on Day 14 compared to Day 1. Complete IRAK4 knockdown in PBMC was comparable to SAD achieved at substantially lower doses: >95% reduction at steady state between Days 7 and 14, at 50-200 mg. The MAD results showed the strongest inhibition of ex vivo cytokine induction at 100 mg corresponding to >90% degradation in monocytes, which was comparable to 1000-1600 mg SAD dosing. Drug accumulation was observed in skin through Day 14, resulting in pre-dose levels ~10-fold higher compared to plasma. Dose-dependent IRAK4 degradation >65% achieved in skin by Day 14, correlating with skin Compound A levels; higher exposures appear to be required in skin for IRAK4 KD compared to blood.

While we have described a number of embodiments of this invention, it is apparent that our basic examples may be altered to provide other embodiments that utilize the compounds and methods of this invention. Therefore, it will be appreciated that the scope of this invention is to be defined by the application and claims rather than by the specific embodiments that have been represented by way of example.

The invention claimed is:

1. A unit dosage form comprising a spray-dried formulation, the spray-dried formulation comprising Compound A or a pharmaceutically acceptable salt thereof, and a pharmaceutically acceptable polymer;
   wherein Compound A is 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl) prop-2-yn-1-yl) oxy) piperidin-1-yl)methyl)cyclohexyl)-1H-pyrazol-4-yl) pyrazolo[1,5-a]pyrimidine-3-carboxamide; and
   wherein the unit dosage form is a tablet of about 208 mg, comprising:
   a tablet core of about 200 mg, comprising
   intragranularly: about 25 mg Compound A free base, about 75 mg hydroxypropylmethylcellulose acetate succinate MG grade (HPMCAS-M), about 15 mg mannitol, about 15 mg microcrystalline cellulose, about 40 mg hydroxypropyl-beta-cyclodextrin, about 19.34 mg croscarmellose sodium, about 2 mg stearyl fumarate sodium, and about 2 mg colloidal silicon dioxide; and
   extragranularly: about 4.66 mg croscarmellose sodium, about 1 mg stearyl fumarate sodium, and about 1 mg colloidal silicon dioxide.

2. The unit dosage form of claim 1, which is a tablet of about 208 mg, comprising:
   i) a tablet core of about 200 mg, comprising
   intragranularly: about 25 mg Compound A free base, about 75 mg hydroxypropylmethylcellulose acetate succinate MG grade (HPMCAS-M), about 15 mg mannitol, about 15 mg microcrystalline cellulose, about 40 mg hydroxypropyl-beta-cyclodextrin, about 19.34 mg croscarmellose sodium, about 2 mg stearyl fumarate sodium, and about 2 mg colloidal silicon dioxide; and
   extragranularly: about 4.66 mg croscarmellose sodium, about 1 mg stearyl fumarate sodium, and about 1 mg colloidal silicon dioxide; and
   ii) a yellow film coating of about 8 mg, comprising about 3.2 mg Polyvinyl Alcohol, 1.616 mg Macrogol/PEG, 1.872 mg Titanium Dioxide, 0.128 mg Iron Oxide, and 1.184 mg Talc.

3. A unit dosage form comprising a spray-dried formulation, the spray-dried formulation comprising Compound A or a pharmaceutically acceptable salt thereof, and a pharmaceutically acceptable polymer;
   wherein Compound A is 5-((1R,4R)-2-oxa-5-azabicyclo[2.2.1]heptan-5-yl)-N-(3-(difluoromethyl)-1-((1r,4R)-4-((4-((3-(1-(2,6-dioxopiperidin-3-yl)-3-methyl-2-oxo-2,3-dihydro-1H-benzo[d]imidazol-4-yl) prop-2-yn-1-yl) oxy) piperidin-1-yl)methyl)cyclohexyl)-1H-pyrazol-4-yl) pyrazolo[1,5-a]pyrimidine-3-carboxamide; and
   wherein the unit dosage form is a tablet of about 824 mg, comprising:
   a tablet core of about 800 mg, comprising
   intragranularly: about 100 mg Compound A free base, about 300 mg hydroxypropylmethylcellulose acetate succinate MG grade (HPMCAS-M), about 45 mg mannitol, about 45 mg microcrystalline cellulose, about 160 mg hydroxypropyl-beta-cyclodextrin, about 77.36 mg croscarmellose sodium, about 8 mg stearyl fumarate sodium, and about 8 mg colloidal silicon dioxide; and
   extragranularly: about 18.64 mg croscarmellose sodium, about 4 mg stearyl fumarate sodium, and about 4 mg colloidal silicon dioxide.

4. The unit dosage form of claim 3, which is a tablet of about 824 mg, comprising:
   i) a tablet core of about 800 mg, comprising
   intragranularly: about 100 mg Compound A free base, about 300 mg hydroxypropylmethylcellulose acetate succinate MG grade (HPMCAS-M), about 45 mg mannitol, about 45 mg microcrystalline cellulose, about 160 mg hydroxypropyl-beta-cyclodextrin, about 77.36 mg croscarmellose sodium, about 8 mg stearyl fumarate sodium, and about 8 mg colloidal silicon dioxide; and
   extragranularly: about 18.64 mg croscarmellose sodium, about 4 mg stearyl fumarate sodium, and about 4 mg colloidal silicon dioxide; and
   ii) a yellow film coating of about 24 mg, comprising about 9.6 mg Polyvinyl Alcohol, 4.848 mg Macrogol/PEG, 5.616 mg Titanium Dioxide, 0.384 mg Iron Oxide, and 3.552 mg Talc.

* * * * *